US008168181B2

(12) United States Patent
Sooknanan et al.

(10) Patent No.: US 8,168,181 B2
(45) Date of Patent: May 1, 2012

(54) METHODS OF IMPAIRING OSTEOCLAST DIFFERENTIATION USING ANTIBODIES THAT BIND SIGLEC-15

(75) Inventors: Roy Rabindranauth Sooknanan, Beaconsfield (CA); Gilles Bernard Tremblay, La Prairie (CA); Mario Filion, Longueuil (CA)

(73) Assignee: Alethia Biotherapeutics, Inc., Montreal (CA)

( * ) Notice: Subject to any disclaimer, the term of this patent is extended or adjusted under 35 U.S.C. 154(b) by 0 days.

(21) Appl. No.: 12/580,943

(22) Filed: Oct. 16, 2009

(65) Prior Publication Data

US 2010/0104575 A1 Apr. 29, 2010

Related U.S. Application Data

(63) Continuation-in-part of application No. 12/279,054, filed as application No. PCT/CA2007/000210 on Feb. 13, 2007, now Pat. No. 7,989,160.

(60) Provisional application No. 60/772,585, filed on Feb. 13, 2006, provisional application No. 60/816,858, filed on Jun. 28, 2006, provisional application No. 61/248,960, filed on Oct. 6, 2009.

(51) Int. Cl.
*A61K 39/00* (2006.01)
*A61K 39/395* (2006.01)

(52) U.S. Cl. ............... 424/130.1; 424/133.1; 424/134.1; 424/135.1; 424/139.1; 424/141.1; 424/142.1; 424/152.1; 514/16.7; 514/16.8; 514/16.9; 514/17.1

(58) Field of Classification Search ........................ None
See application file for complete search history.

(56) References Cited

U.S. PATENT DOCUMENTS

| | | | |
|---|---|---|---|
| 5,712,127 A | 1/1998 | Malek | |
| 6,451,555 B1 | 9/2002 | Duffy et al. | |
| 6,498,024 B1 | 12/2002 | Malek et al. | |
| 6,617,434 B1 | 9/2003 | Duffy et al. | |
| 7,357,929 B2 | 4/2008 | Carmeliet et al. | |
| 7,402,664 B2 | 7/2008 | Wolfgang | |
| 7,407,940 B2 | 8/2008 | Falla | |
| 7,411,051 B2 | 8/2008 | Rosen | |
| 7,417,112 B2 | 8/2008 | Rathore | |
| 7,425,612 B2 | 9/2008 | Nakamura | |
| 7,432,065 B2 | 10/2008 | Lu | |
| 7,449,320 B2 | 11/2008 | Miller | |
| 7,459,539 B2 | 12/2008 | Challita-Eid | |
| 7,485,327 B2 | 2/2009 | Kim | |
| 7,488,590 B2 | 2/2009 | Feige | |
| 7,501,391 B2 | 3/2009 | Khan | |
| 7,501,557 B1 | 3/2009 | Wagner | |
| 7,510,840 B1 | 3/2009 | Challita-Eid | |
| 7,514,224 B2 | 4/2009 | Lu | |
| 7,514,407 B2 | 4/2009 | Averback | |
| 7,517,529 B2 | 4/2009 | Khan | |
| 7,524,513 B2 | 4/2009 | Hai-Quan | |
| 7,528,232 B2 | 5/2009 | Wagner | |
| 7,528,242 B2 | 5/2009 | Anderson | |
| 7,534,579 B2 | 5/2009 | Glucksmann | |
| 7,541,450 B2 | 6/2009 | Liu | |
| 7,547,512 B2 | 6/2009 | Peiris | |
| 7,560,433 B2 | 7/2009 | Khan | |
| 7,566,685 B2 | 7/2009 | Kinsella | |
| 7,569,547 B2 | 8/2009 | Lindberg | |
| 7,572,894 B2 | 8/2009 | Jin | |
| 7,575,876 B2 | 8/2009 | Zhang | |
| 7,585,839 B2 | 9/2009 | Larsen | |
| 7,585,849 B2 | 9/2009 | Liu | |
| 7,585,937 B2 | 9/2009 | Kungl | |
| 7,601,807 B2 | 10/2009 | Kanayama | |
| 7,608,704 B2 | 10/2009 | Yue | |
| 7,625,996 B2 | 12/2009 | Fischer | |
| 7,628,989 B2 | 12/2009 | Jakobovits | |
| 7,635,681 B2 | 12/2009 | Bonny | |
| 7,635,755 B2 | 12/2009 | Kaplan | |
| 7,641,905 B2 | 1/2010 | Jakobovits | |
| 7,662,409 B2 | 2/2010 | Masters | |
| 7,662,776 B2 | 2/2010 | Khan | |
| 7,671,011 B2 | 3/2010 | Shai | |
| 7,691,977 B2 | 4/2010 | Fuh | |
| 7,989,160 B2 | 8/2011 | Sooknanan et al. | |
| 2004/0076992 A1 | 4/2004 | Nakamura | |
| 2004/0082508 A1 | 4/2004 | Yue | |
| 2005/0107588 A1 | 5/2005 | Duggan | |
| 2005/0118625 A1 | 6/2005 | Mounts | |

(Continued)

FOREIGN PATENT DOCUMENTS

EP 1369479 12/2003

(Continued)

OTHER PUBLICATIONS

Agrawal et al., "RNA interference: biology, mechanism, and applications," *Microbiol Mol Biol Rev* 67(4):657-685 (2003). Baron, "Anatomy and Biology of Bone Matrix and Cellular Elements," *Primer on the Metabolic Bone Diseases and Disorders of Mineral Metabolism*, Fifth Ed., American Society for Bone and Mineral Research, Washington, D.C., pp. 1-8 (2003).

Biskobing, "Acid pH increases carbonic anhydrase II and calcitonin receptor mRNA expression in mature osteoclasts," *Calcif Tissue Int* 67(2):178-183 (2000).

Boyle et al., "Osteoclast differentiation and activation," *Nature* 423(6937):337-342 (2003).

(Continued)

*Primary Examiner* — Elizabeth C Kemmerer
(74) *Attorney, Agent, or Firm* — Choate, Hall & Stewart, LLP; Fangli Chen; Robert N. Sahr

(57) ABSTRACT

This invention relates, in part, to unique and newly identified genetic polynucleotides involved in the process of bone remodeling; variants and derivatives of the polynucleotides and corresponding polypeptides; uses of the polynucleotides, polypeptides, variants and derivatives; and methods and compositions for the amelioration of symptoms caused by bone remodeling disorders. Disclosed in particular are, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes.

25 Claims, 11 Drawing Sheets

U.S. PATENT DOCUMENTS

| | | |
|---|---|---|
| 2005/0153333 A1 | 7/2005 | Sooknanan |
| 2006/0153867 A1 | 7/2006 | Li |
| 2006/0240516 A1 | 10/2006 | Jalinot |
| 2008/0171094 A1 | 7/2008 | Benner |
| 2008/0176243 A1 | 7/2008 | Khan |
| 2008/0176790 A1 | 7/2008 | DeFrees |
| 2008/0178308 A1 | 7/2008 | Afar |
| 2008/0194489 A1 | 8/2008 | Khan |
| 2008/0199939 A1 | 8/2008 | Havenga |
| 2008/0206239 A1 | 8/2008 | Jones |
| 2008/0207502 A1 | 8/2008 | Rastelli |
| 2008/0207522 A1 | 8/2008 | Hancock |
| 2008/0213268 A1 | 9/2008 | Watts |
| 2008/0242618 A1 | 10/2008 | Khan |
| 2008/0242837 A1 | 10/2008 | Khan |
| 2008/0242847 A1 | 10/2008 | Liu |
| 2008/0248527 A1 | 10/2008 | Wolfgang |
| 2008/0254020 A1 | 10/2008 | Walker |
| 2008/0261819 A1 | 10/2008 | Lorens |
| 2008/0274979 A1 | 11/2008 | Ellis-Behnke |
| 2008/0275547 A1 | 11/2008 | Kanamaru |
| 2008/0279908 A1 | 11/2008 | Bertozzi |
| 2008/0286808 A1 | 11/2008 | Schellenberger |
| 2008/0287309 A1 | 11/2008 | Bowdish |
| 2008/0299111 A1 | 12/2008 | Delacourte |
| 2008/0299601 A1 | 12/2008 | Fike |
| 2008/0306001 A1 | 12/2008 | Liik |
| 2008/0306009 A1 | 12/2008 | Khan |
| 2008/0318871 A1 | 12/2008 | Khan |
| 2009/0004210 A1 | 1/2009 | Mattner |
| 2009/0005257 A1 | 1/2009 | Jespers |
| 2009/0005266 A1 | 1/2009 | Ostermeier |
| 2009/0005541 A1 | 1/2009 | Kungl |
| 2009/0010983 A1 | 1/2009 | Melvik |
| 2009/0012032 A1 | 1/2009 | Nakamura |
| 2009/0017460 A1 | 1/2009 | Anderson |
| 2009/0019605 A1 | 1/2009 | Takagi |
| 2009/0023648 A1 | 1/2009 | Stredonsky |
| 2009/0028813 A1 | 1/2009 | Stedronsky |
| 2009/0028856 A1 | 1/2009 | Chen |
| 2009/0041671 A1 | 2/2009 | Young |
| 2009/0042769 A1 | 2/2009 | MacLean |
| 2009/0047335 A1 | 2/2009 | Rastelli |
| 2009/0069259 A1 | 3/2009 | Collingwood |
| 2009/0075377 A1 | 3/2009 | Lu |
| 2009/0081178 A1 | 3/2009 | Murray |
| 2009/0081457 A1 | 3/2009 | Nagarajan |
| 2009/0082551 A1 | 3/2009 | Zuckerman |
| 2009/0088387 A1 | 4/2009 | Castillo |
| 2009/0092582 A1 | 4/2009 | Bogin |
| 2009/0093408 A1 | 4/2009 | Bridon |
| 2009/0093621 A1 | 4/2009 | Ferrari |
| 2009/0099031 A1 | 4/2009 | Stemmer |
| 2009/0099066 A1 | 4/2009 | Moulton |
| 2009/0117578 A1 | 5/2009 | Metz |
| 2009/0123412 A1 | 5/2009 | Healy |
| 2009/0130111 A1 | 5/2009 | Wu |
| 2009/0131265 A1 | 5/2009 | Zhang |
| 2009/0136595 A1 | 5/2009 | Shah |
| 2009/0136912 A1 | 5/2009 | Kurokawa |
| 2009/0142280 A1 | 6/2009 | Zhang |
| 2009/0142828 A1 | 6/2009 | Bucciarelli |
| 2009/0142839 A1 | 6/2009 | Primiano |
| 2009/0143567 A1 | 6/2009 | Rathore |
| 2009/0149339 A1 | 6/2009 | Lu |
| 2009/0169520 A1 | 7/2009 | Soreq |
| 2009/0170191 A1 | 7/2009 | Jakobovits |
| 2009/0175821 A1 | 7/2009 | Bridon |
| 2009/0176664 A1 | 7/2009 | Chu |
| 2009/0180958 A1 | 7/2009 | Koivistoinen |
| 2009/0197812 A1 | 8/2009 | Kim |
| 2009/0214570 A1 | 8/2009 | Mrsny |
| 2009/0214582 A1 | 8/2009 | Dean |
| 2009/0215667 A1 | 8/2009 | Wagner |
| 2009/0221505 A1 | 9/2009 | Kolonin |
| 2009/0226372 A1 | 9/2009 | Ruoslahti |
| 2009/0226374 A1 | 9/2009 | Hugli |
| 2009/0226433 A1 | 9/2009 | Grandea, III |
| 2009/0227505 A1 | 9/2009 | Khan |
| 2009/0234026 A1 | 9/2009 | Kaplan |
| 2009/0252728 A1 | 10/2009 | Jakobovits |
| 2009/0258017 A1 | 10/2009 | Callahan |
| 2009/0264372 A1 | 10/2009 | Dal Farra |
| 2009/0270320 A1 | 10/2009 | Panjwani |
| 2009/0275050 A1 | 11/2009 | Glucksmann |
| 2009/0275503 A1 | 11/2009 | Shai |
| 2009/0281038 A1 | 11/2009 | Wagner |
| 2009/0298707 A1 | 12/2009 | Yarbrough |
| 2009/0304746 A1 | 12/2009 | Sette |
| 2009/0317420 A1 | 12/2009 | Telford |
| 2010/0004172 A1 | 1/2010 | Khan |
| 2010/0015664 A1 | 1/2010 | Kanayama |
| 2010/0016215 A1 | 1/2010 | Moulton |
| 2010/0016220 A1 | 1/2010 | Nakamura |
| 2010/0016697 A1 | 1/2010 | Spinale |
| 2010/0029005 A1 | 2/2010 | Kamiie |
| 2010/0035817 A1 | 2/2010 | Fischer |
| 2010/0041614 A1 | 2/2010 | Bussolino |
| 2010/0047163 A1 | 2/2010 | Forte |
| 2010/0055438 A1 | 3/2010 | Kaplan |
| 2010/0056457 A1 | 3/2010 | Barbas, III |
| 2010/0056459 A1 | 3/2010 | Bonny |
| 2010/0076173 A1 | 3/2010 | Stephanopoulos |
| 2010/0080814 A1 | 4/2010 | Desjarlais |
| 2010/0080824 A1 | 4/2010 | Peiris |
| 2010/0086532 A1 | 4/2010 | Barbas, III |
| 2010/0209428 A1 | 8/2010 | Hiruma et al. |
| 2011/0268733 A1 | 11/2011 | Hiruma et al. |

FOREIGN PATENT DOCUMENTS

| | | |
|---|---|---|
| EP | 1544215 | 6/2005 |
| EP | 1580263 | 9/2005 |
| EP | 1751179 | 2/2007 |
| EP | 1874337 | 1/2008 |
| EP | 1931198 | 6/2008 |
| EP | 1934252 | 6/2008 |
| EP | 1950221 | 7/2008 |
| EP | 1953551 | 8/2008 |
| EP | 1963499 | 9/2008 |
| EP | 1970383 | 9/2008 |
| EP | 1996609 | 12/2008 |
| EP | 2002036 | 12/2008 |
| EP | 2021467 | 2/2009 |
| EP | 2032149 | 3/2009 |
| EP | 2041569 | 4/2009 |
| EP | 2046806 | 4/2009 |
| EP | 2053406 | 4/2009 |
| EP | 2057465 | 5/2009 |
| EP | 2097094 | 9/2009 |
| EP | 2105141 | 9/2009 |
| EP | 2130838 | 12/2009 |
| EP | 2129682 | 1/2010 |
| EP | 2140005 | 1/2010 |
| EP | 2168986 | 3/2010 |
| EP | 2170363 | 4/2010 |
| JP | 2003210166 | 7/2003 |
| JP | 2004107352 | 4/2004 |
| JP | 2004189848 | 7/2004 |
| JP | 2004533803 | 11/2004 |
| JP | 2004339189 | 12/2004 |
| JP | 2007020403 | 2/2007 |
| JP | 2008500267 | 1/2008 |
| JP | 2008504221 | 2/2008 |
| JP | 2008094822 | 4/2008 |
| JP | 2008111841 | 5/2008 |
| JP | 2008263955 | 11/2008 |
| JP | 2009072081 | 4/2009 |
| JP | 2009183293 | 8/2009 |
| JP | 2009528255 | 8/2009 |
| WO | WO9411014 | 5/1994 |
| WO | WO0220723 A2 | 3/2002 |
| WO | WO0220822 | 3/2002 |
| WO | WO-03048305 | 6/2003 |
| WO | WO03104275 | 12/2003 |
| WO | WO2004064972 | 8/2004 |
| WO | WO2005061546 A1 | 7/2005 |
| WO | WO2005081628 | 9/2005 |

| | | |
|---|---|---|
| WO | WO2006113311 | 10/2006 |
| WO | WO2007043059 | 4/2007 |
| WO | WO2007062422 | 5/2007 |
| WO | WO2007063300 | 7/2007 |
| WO | WO2007100524 | 9/2007 |
| WO | WO2007104062 | 9/2007 |
| WO | WO2007111952 | 10/2007 |
| WO | WO2007128121 | 11/2007 |
| WO | WO2007146319 | 12/2007 |
| WO | WO2008006028 | 1/2008 |
| WO | WO2008024105 | 2/2008 |
| WO | WO2008116468 | 2/2008 |
| WO | WO2008063369 | 5/2008 |
| WO | WO2008093982 | 8/2008 |
| WO | WO2008101160 | 8/2008 |
| WO | WO2008113185 | 9/2008 |
| WO | WO2008134544 | 11/2008 |
| WO | WO2008148545 | 12/2008 |
| WO | WO2009005793 | 1/2009 |
| WO | WO2009008727 | 1/2009 |
| WO | WO2009023125 | 2/2009 |
| WO | WO2009039854 | 2/2009 |
| WO | WO2009031835 | 3/2009 |
| WO | WO2009031836 | 3/2009 |
| WO | WO2009032158 | 3/2009 |
| WO | WO2009038756 | 3/2009 |
| WO | WO2009146179 | 3/2009 |
| WO | WO-2009048072 | 4/2009 |
| WO | WO2009050453 | 4/2009 |
| WO | WO2009059379 | 5/2009 |
| WO | WO2009059972 | 5/2009 |
| WO | WO2009061130 | 5/2009 |
| WO | WO2009061890 | 5/2009 |
| WO | WO2009132876 | 5/2009 |
| WO | WO2009090651 | 7/2009 |
| WO | WO2009106715 | 9/2009 |
| WO | WO2009108261 | 9/2009 |
| WO | WO2009112645 | 9/2009 |
| WO | WO2009139599 | 11/2009 |
| WO | WO2009020101 | 12/2009 |
| WO | WO2010035504 | 1/2010 |
| WO | WO2010033736 | 3/2010 |
| WO | WO2010037395 | 4/2010 |
| WO | WO2010000794 | 7/2010 |

OTHER PUBLICATIONS

Brage et al., "Different cysteine proteinases involved in bone resorption and osteoclast formation," *Calcif Tissue Int* 76(6):439-447 (2005).
Brandenberger et al., "Transcriptome characterization elucidates signaling networks that control human ES cell growth and differentiation," *Nat Biotechnol* 22(6):707-716 (2004).
Brummelkamp et al., "A system for stable expression of short interfering RNAs in mammalian cells," *Science* 296(5567):550-553 (2002).
Database Geneseq [Online] Derwent; May 3, 2007, "Human siglec 15, SEQ ID2." XP002531845, from JP-2007020403 (Nat. Inst. of Adv. Ind. & Technol.).
deVERNEJOUL, "Dynamics of Bone Remodeling: Biochemical and Pathophysiological Basis," *Eur J Clin Chem Clin Biochem* 34:729-734 (1996).
Elbashir et al., "Duplexes of 21-nucleotide RNAs mediate RNA interference in cultured mammalian cells," *Nature* 411(6836):494-8 (2001).
Frost, "Dynamics of Bone Remodeling," *Bone Biodynamics*, Little and Brown, Boston, MA p. 315 (1964).
Gee et al., "Potential Therapeutic Usefulness of Intermolecular Triplex DNA," Molecular and Immunologic Approaches, Futura Publishing Co., Mt. Kisco, NY, pp. 163-177 (1994).
GenBank Acc. No. AK172835.1, GI:47077862, 2004.
GenBank Acc. No. AL357873, GI:16972902, 2008.
GenBank Acc. No. AL645465, GI:18476850, 2008.
GenBank Acc. No. NM_000067, GI:157952216, first referenced 1976, updated 2008.
GenBank Acc. No. NM_000099, GI:19882253, first referenced 1990, updated 2008.
GenBank Acc. No. NM_000887, GI:34452172, first referenced 1987, updated 2008.
GenBank Acc. No. NM_001014433, GI:62526019, first referenced 2000, updated 2005.
GenBank Acc. No. NM_001102, GI:194097348, first referenced 1989, updated 2008.
GenBank Acc. No. NM_001690, GI:19913423, first referenced 1993, updated 2007.
GenBank Acc. No. NM_001935, GI:47078262, first referenced 1991, updated 2008.
GenBank Acc. No. NM_002994, GI:41872613, first referenced 1991, updated 2008.
GenBank Acc. No. NM_003341, GI:33359692, first referenced 1993, updated 2008.
GenBank Acc. No. NM_004414, GI:44680111, first referenced 1995, updated 2008.
GenBank Acc. No. NM_004763, GI:115527101, first referenced 1997, updated 2007.
GenBank Acc. No. NM_004794, GI:34485717, first referenced 1993, updated 2005.
GenBank Acc. No. NM_005410, GI:62530390, first referenced 1991, updated 2008.
GenBank Acc. No. NM_005765, GI:15011917, first referenced 1998, updated 2007.
GenBank Acc. No. NM_006357, GI:33359695, first referenced 1997, updated 2008.
GenBank Acc. No. NM_006555, GI:34304384, first referenced 1997, updated 2007.
GenBank Acc. No. NM_006660, GI:12597621, first referenced 1999, updated 2008.
GenBank Acc. No. NM_013322, GI:23111022, first referenced 2001, updated 2006.
GenBank Acc. No. NM_014358, GI:90577173, first referenced 1999, updated 2003.
GenBank Acc. No. NM_014656, GI:7657258, 2006.
GenBank Acc. No. NM_015973, GI:88853582, first referenced 1990, updated 2008.
GenBank Acc. No. NM_018252, GI:149158718, 2006.
GenBank Acc. No. NM_018482, GI:46094080, first referenced 1998, updated 2008.
GenBank Acc. No. NM_021181, GI:19923571, first referenced 2001, updated 2008.
GenBank Acc. No. NM_030794, GI:13540575, first referenced 2000, updated 2008.
GenBank Acc. No. NM_032565; GI:141802977, first referenced 2003, updated 2007.
GenBank Acc. No. NM_032569; GI:190358483, first referenced 2005, updated 2006.
GenBank Acc. No. NM_032731; GI:153791420, first referenced 2004, updated 2008.
GenBank Acc. No. NM_054027; GI:170671715, first referenced 1995, updated 2008.
GenBank Acc. No. NM_138461; GI:115511027, 2004.
GenBank Acc. No. NM_145280; GI:188528683, 2004.
GenBank Acc. No. NM_178833; GI:196259823, first referenced 2007, updated 2008.
GenBank Acc. No. NM_182488; GI:209954829, first referenced 1998, updated 2004.
GenBank Acc. No. NM_213602; GI:47106068, 2007.
GenBank Acc. No. XM_884636, GI:149270200, 2007.
GenBank accession No. AAY40743, Angata T. et al., J. Glycobiology 17 (8), pp. 838-846 (2007).
GenBank accession No. AAY40744, Angata, T. et al., J. Glycobiology 17 (8), 838-846 (2007).
GenBank accession No. BAD18800, Kawabata A. et al., Direct Submission, submitted (Apr. 22, 2004), Institute of Medical Science.
GenBank accession No. BAF83089, Wakamatsu A. et al., Direct submission, submitted (Oct. 9, 2007) Reverse Proteomics Researach Institute.
GenBank accession No. BAF83091, Wakamatsu A. et al., Direct submission, submitted (Oct. 9, 2007) Reverse Proteomics Researach Institute.
Hannon, "RNA interference," *Nature* 418(6894):244-251 (2002).

IPI No. IPI00568858.3, Apr. 20, 2010.
IPI No. IPI00647937.1, Sep. 4, 2005.
IPI No. IPI00796217.1, Oct. 31, 2006.
Ishida et al., "Large Scale Gene Expression Analysis of Osteoclastogenesis in Vitro and Elucidation of NFAT2 as a Key Regulator," *J Bio Chem* 277(43):41147-41156 (2002).
Ishida et al., "Large scale gene expression analysis of osteoclastogenesis in vitro and elucidation of NFAT2 as a key regulator," *J. Biol. Chem.* 277:41147-41156 (2002).
Janssen et al., "LAB: A new membrane-associated adaptor molecule in B cell activation," *Nat Immunol* 4(2):117-123 (2003).
Jilka et al., "Increased Osteoclast Development After Estrogen Loss: Mediation by Interleukin-6," *Science* 257:88-91 (1992).
Kawai et al., "Functional annotation of a full-length mouse cDNA collection," *Nature* 409(6821):685-690 (2001).
Kawaida et al., "Jun Dimerization Protein 2 (JDP2), a Member of the AP-1 Family of Transcription Factor, Mediates Osteoclast Differentiation Induced by RANKL,"*J Exp Med* 197(8):1029-1035 (2003).
Malkin et al., "Association of ANKH gene polymorphisms with radiographic hand bone size and geometry in a Chuvasha population," *Bone* 36(2):365-373 (2005).
McMahon et al., "Bone marrow transplantation corrects osteoporosis in the carbonic anhydrase II deficiency syndrome," *Blood* 97(7):1947-1950 (2001).
Morello et al., "cDNA cloning, characterization and chromosome mapping of *Crtap* encoding the mouse Cartilage Associated Protein," *Matrix Biol* 18(3):319-324 (1999).
NCBI Reference sequence: XP_001056537, Apr. 2, 2010.
NCBI Reference sequence: NP_001094508, May 28, 2010.
NCBI Reference sequence: NP_998767, Angata T. et al., J. Glycobiology 17 (8), pp. 838-846 (2007).
NCBI Reference sequence: XP_001089000, Jun. 1, 2010.
NCBI Reference sequence: XP_512109, Sep. 16, 2006.
NCBI Reference sequence: XP_574176, Apr. 2, 2010.
NCBI Reference sequence: XP_601064, Jun. 3, 2010.
NCBI Reference sequence: XP_855238, Aug. 30, 2005.
Netzel-Arnett et al., "Membrane anchored serine proteases: A rapidly expanding group of cell surface proteolytic enzymes with potential roles in cancer," *Cancer Metastasis Rev* 22(2-3):237-258 (2003).
Nishi et al., "Expression and Function of the Mouse V-ATPase d Subunit Isoforms," *J Biol Chem* 278(47):46396-46402 (2003).
Nishi et al., "The Vacuolar ($H^+$)-ATPases—Nature's Most Versatile Protein Pumps," *Nat Rev Mol Cell Biol* 3(2):94-103 (2002).
Poli et al., "Interleukin-6 deficient mice are protected from bone loss caused by estrogen depletion," *EMBO J* 13:1189-1196 (1994).
Rubinson et al., "A lentivirus-based system to functionally silence genes in primary mammalian cells, stem cells and transgenic mice by RNA interference," *Nat Genet* 33(3):401-406 (2003).
Shan et al., "TSP50, A Possible Protease in Human Testes, Is Activated in Breast Cancer Epithelial Cells," *Cancer Res* 62(1):290-294 (2002).
Smith et al., "Mutations in *ATP6N1B*, encoding a new kidney vacuolar proton pump 116-kD subunit, cause recessive distal renal tubular acidosis with preserved hearing," *Nat Genet* 26(1)71-75 (2000).
Smith et al., "Vacuolar $H^+$-ATPase d2 Subunit: Molecular Characterization, Developmental Regulation, and Localization to Specialized Proton Pumps in Kidney and Bone," *J Am Soc Nephrol* 16(5):1245-1256 (2005).
Srivastava et al., "Estrogen Blocks M-CSF Gene Expression and Osteoclast Formation by Regulating Phosphorylation of Egr-1 and Its Interaction with Sp-1," *J Clin Invest* 102:1850-1859 (1998).
Stehberger et al., "Localization and regulation of the ATP6V0A4 (a4) Vacuolar $H^+$-ATPase Subunit Defective in an Inherited Form of Distal Renal Tubular Acidosis," *J Am Soc Nephrol* 14(12):3027-3038 (2003).
Strausberg et al., "Generation and initial analysis of more than 15,000 full-length human and mouse cDNA sequences," *Proc Natl Acad Sci USA* 99(26):16899-16903 (2002).
Supplementary European Search Report, EP07710624, date of mailing Jul. 10, 2009.
Tonachini et al., "cDNA cloning, characterization and chromosome mapping of the gene encoding human cartilage associated protein (CRTAP)," *Cytogenet Cell Genet* 87(3-4):191-194 (1999).
UniProtKB/TrEMBL A7E1W8_Mouse, Sep. 11, 2007.
Yuan et al., "Isolation of a Novel Gene, *TSP50*, by a Hypomethylated DNA Fragment in Human Breast Cancer," *Cancer Res* 59(13):3215-3221 (1999).
Ngo et al., 1994, The Protein Folding Problem and Tertiary Structure Prediction, Merz et al., eds. Birkhauser, Boston, pp. 492-495.
Sordillo et al., (2003) RANK-Fc: A Therapeutic Antagonist for RANK-L in Myeloma: Skeletal Complications of Malignancy, Cancer Supp. 97(3):802-812.
Stuible, M. et al., Sep. 2011, abstract of oral presentation No. 1187, The American Society for Bone and Mineral Research.
Wells et al., 1990, Biochemistry 29:8509-8517.
GeneBank Acc. No. NM_00104433, first referenced 2000, updated 2009.
Angata, T. et al., (2007) "Siglec-15: An immune system Siglec conserved throughout vertebrate evolution", Glycobiology, vol. 17(8):838-846.
Hiruma, Y, et al., (2011) "Siglec-15, a member of the sialic acid-binding lectin, is a novel regulator for osteoclst diffrerentiation" Biochem Biophys Commun 409(3):424-429.
ENSEMBL Protein ID: ENSBTAP00000016659; Jul. 19, 2010.
ENSEMBL Protein ID: ENSBTAP00000022107; Jul. 19, 2010.
ENSEMBL Protein ID: ENSCAFP00000026052; Jul. 19, 2010.
ENSEMBL Protein ID: ENSDNOP00000011608; Jul. 19, 2010.
ENSEMBL Protein ID: ENSECAP00000015632; Jul. 19, 2010.
ENSEMBL Protein ID: ENSFCAP00000009910; Jul. 19, 2010.
ENSEMBL Protein ID: ENSMICP00000015938; Jul. 19, 2010.
ENSEMBL Protein ID: ENSMLUP00000004457; Jul. 19, 2010.
ENSEMBL Protein ID: ENSMMUP00000004742; Jul. 19, 2010.
ENSEMBL Protein ID: ENSMUSP00000112309; Jul. 19, 2010.
ENSEMBL Protein ID: ENSOPRP00000004369; Jul. 19, 2010.
ENSEMBL Protein ID: ENSPPYP00000010254; Jul. 19, 2010.
ENSEMBL Protein ID: ENSPTRP00000042370; Jul. 19, 2010.
ENSEMBL Protein ID: ENSPTRP00000049394; Jul. 19, 2010.
ENSEMBL Protein ID: ENSRNOP00000041280; Jul. 19, 2010.
ENSEMBL Protein ID: ENSSARP00000011800; Jul. 19, 2010.
ENSEMBL Protein ID: ENSSTOP00000002285; Jul. 19, 2010.
ENSEMBL Protein ID: ENSP00000374125; Jul. 6, 2010.
IPI No. IPI00663527.4; sequence update Sep. 10, 2007.
IPI No. IPI00711850.4; sequence update Jun. 9, 2010.
UniProtKB/Swiss-Prot A8K2Y5_Human; last modified Jul. 13, 2010.
UniProtKB/TrEMBL A7E1W7_Human; last modified Mar. 2, 2010.
UniProtKB/Swiss-Prot Q6ZMC9 (SIG15_HUMAN); last modified Jun. 15, 2010.
IPI No. IPI00716135.2, 2007.
Lee, J. et al. "Stable gene silencing in human monocytic cell lines using lentiviral-delivered small interference RNA . . . " (2004) J Biol Chem 279(10): 9379-9388.
Sooknanan et al., (2004) "Identification of osteoclast-specific gene using subtractive transcription amplification of mRNA (STAR)" J. Bone Min. Res. 19:S415.
Tremblay et al., (2004) "Functional validation of osteoclast-specific genes in RAW264.7 cells by RNA interference" J. Bone Min. Res. 19:S414.
Bird RE et al., Single-Chain antigen binding proteins Science. 242 (4877):423-426, 1988.

The knockdown effects on osteoclastogenesis of the mouse orthologue for AB0326 (SEQ. ID. NO. 35) in the RAW 264.7 model A functional complementation assay for SEQ. ID. NO. 1 (AB0326) in RAW-0326.2 cells to screen for inhibitors of osteoclastogenesis

ELISA with biotinylated Fc-SIGLEC-15₂₀₋₂₅₉

|   | 1 | 2 | 3 | 4 | 5 | 6 | 7 | 8 | 9 | 10 | 11 | 12 |
|---|---|---|---|---|---|---|---|---|---|---|---|---|
| A | 0.793 | 0.828 | 1.079 | 0.151 | 0.98 | 0.125 | 0.133 | 0.133 | 0.136 | 0.15 | 0.782 | 0.384 |
| B | 0.603 | 0.158 | 0.147 | 1.001 | 0.143 | 0.313 | 0.141 | 0.613 | 0.716 | 0.156 | 0.457 | 1.052 |
| C | 0.473 | 0.155 | 0.443 | 0.134 | 0.118 | 1.005 | 0.163 | 0.517 | 0.966 | 0.93 | 1.059 | 0.151 |
| D | 0.152 | 0.17 | 1.319 | 1.118 | 1.07 | 1.04 | 0.161 | 0.909 | 0.155 | 0.979 | 0.158 | 0.148 |
| E | 0.354 | 0.167 | 0.952 | 0.169 | 0.312 | 0.436 | 0.518 | 0.968 | 0.491 | 0.13 | 0.169 | 1.018 |
| F | 0.142 | 1.131 | 1.111 | 1.027 | 0.573 | 0.751 | 0.818 | 0.15 | 0.845 | 0.512 | 0.888 | 0.997 |
| G | 0.153 | 0.162 | 1.106 | 0.854 | 0.509 | 0.246 | 0.732 | 0.869 | 0.39 | 0.847 | 0.356 | 0.221 |
| H | 0.916 | 1.254 | 0.18 | 0.931 | 1.192 | 1.219 | 0.905 | 0.868 | 0.24 | 0.518 | 0.479 | 1.115 |

B

ELISA with biotinylated Fc

|   | 1 | 2 | 3 | 4 | 5 | 6 | 7 | 8 | 9 | 10 | 11 | 12 |
|---|---|---|---|---|---|---|---|---|---|---|---|---|
| A | 0.118 | 1.879 | 0.112 | 0.119 | 0.119 | 0.113 | 0.102 | 1.002 | 0.123 | 0.101 | 0.133 | 1.603 |
| B | 1.811 | 0.129 | 0.123 | 0.12 | 0.124 | 0.134 | 0.231 | 0.151 | 1.872 | 0.185 | 0.124 | 0.152 |
| C | 0.168 | 0.185 | 1.585 | 0.13 | 0.161 | 0.122 | 0.138 | 1.771 | 0.167 | 0.16 | 1.946 | 0.261 |
| D | 0.117 | 0.173 | 0.134 | 0.12 | 0.133 | 0.128 | 0.133 | 0.137 | 0.152 | 0.209 | 0.219 | 0.255 |
| E | 1.284 | 0.126 | 1.883 | 0.138 | 0.132 | 0.135 | 0.135 | 0.12 | 0.143 | 0.151 | 0.139 | 0.148 |
| F | 0.116 | 0.146 | 0.14 | 1.805 | 0.197 | 0.145 | 0.144 | 0.132 | 0.158 | 0.152 | 0.13 | 0.14 |
| G | 0.128 | 0.13 | 0.138 | 0.128 | 0.137 | 0.134 | 0.126 | 0.125 | 0.135 | 0.134 | 0.132 | 0.146 |
| H | 0.128 | 0.139 | 0.13 | 0.124 | 0.141 | 0.147 | 0.136 | 0.138 | 0.131 | 0.127 | 0.134 | 1.982 |

METHODS OF IMPAIRING OSTEOCLAST DIFFERENTIATION USING ANTIBODIES THAT BIND SIGLEC-15

This application is a continuation-in-part of U.S. Ser. No. 12/279,054, filed Jan. 13, 2009, now U.S. Pat. No. 7,989,160, which is a national stage application of PCT/CA2007/000210 filed on Feb. 13, 2007, the entire content of which is incorporated herein by reference, which application claims the benefit of U.S. Provisional Application Ser. No. 60/772,585 filed on Feb. 13, 2006 and U.S. Provisional Application Ser. No. 60/816,858 filed on Jun. 28, 2006 the entire content of which is incorporated herein by reference. This application claims the benefit of U.S. Provisional Application Ser. No. 61/248,960 filed Oct. 6, 2009.

In accordance with 37 CFR 1.52(e)(5), a Sequence Listing in the form of a text file (entitled "Sequence listing.txt," created on Dec. 28, 2009, and 160 kilobytes) is incorporated herein by reference in its entirety.

FIELD OF THE INVENTION

This invention relates, in part, to unique and newly identified genetic polynucleotides involved in the process of bone remodeling; variants and derivatives of the polynucleotides and corresponding polypeptides; uses of the polynucleotides, polypeptides, variants and derivatives; methods and compositions for the amelioration of symptoms caused by bone remodeling disorders, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In particular, this invention relates to antibodies and antigen binding fragments, polynucleotide expression profiles of active osteoclasts, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes, as well as in diagnosis of disease states or in the predisposition to develop same.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodeling. The development and proliferation of these cells from their progenitors is governed by networks of growth factors and cytokines produced in the bone microenvironment as well as by systemic hormones. Bone remodeling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodeling genes.

Any interference or imbalance arising in the bone remodeling process can produce skeletal disease, with the most common skeletal disorders characterized by a net decrease in bone mass. A primary cause of this reduction in bone mass is an increase in osteoclast number and/or activity. The most common of such disease, and perhaps the best known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodeling is a locally controlled process being that it takes place in discrete packets throughout the skeleton as first described by Frost over forty years ago (Frost H. M. 1964).

Since bone remodeling takes place in discrete packets, locally produced hormones and enzymes may be more important than systemic hormones for the initiation of bone resorption and the normal remodeling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (M-CSF) receptor, both of which are responsible for osteoclast differentiation, as well as the calcitonin receptor capable of rapidly inactivating the osteoclast (Baron, R. 2003).

In a complex pattern of inhibition and stimulation, growth hormone, insulin-like growth factor-1, the sex steroids, thyroid hormone, calciotrophic hormones such as PTH and prostaglandin E2, various cytokines, such as interleukin-1 beta, interleukin-6, and tumour necrosis factor-alpha, and 1,25-dihydroxyvitamin D (calcitriol) act co-ordinately in the bone remodeling process (Jilka et al. 1992; Poli et al. 1994; Srivastava et al. 1998; de Vernejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity will permit a clearer understanding of the remodeling process and offer tissue specific therapeutic targets for the treatment of disease states related to bone remodeling.

Many diseases linked to bone remodeling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bisphosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminum can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other anti-resorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodeling is that of the use of etidronate (Didronel) first approved by the FDA to treat Paget's disease. Paget's disease is a bone disease characterized by a disorderly and accelerated remodeling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

There thus remains a need to better understand the bone remodeling process and to provide new compositions that are useful for the diagnosis, prognosis, treatment, prevention and evaluation of therapies for bone remodeling and associated disorders. A method for analysing polynucleotide expression patterns has been developed and applied to identify polynucleotides, polypeptides, variants and derivatives specifically involved in bone remodeling. Methods of identifying compounds for modulating osteoclast differentiation were developed and therapeutic antibodies and antigen binding fragments against SIGLEC-15 (SEQ ID NO.:2) and against SIGLEC-15 variants were obtained.

Sialic-acid-binding immunoglobulin-like lectins (Siglecs) are members of the immunoglobulin (Ig) superfamily that have the ability to interact with sialic acids (McMillan and Crocker, 2008; Crocker et al., 2007). There are several Siglec family members that all share specific structural features, in particular, displaying an amino-terminal V-set Ig domain that binds to sialic acid and a variable number of C2-set Ig domains. These membrane receptors are generally expressed in highly specific manners and many of the family members are expressed in hematopoietic cells (McMillan and Crocker, 2008). These proteins are thought to promote cell-cell interactions, mediate signaling, and regulate immune functions through the recognition of glycans (Crocker et al., 2007). Sialic acids are nine-carbon sugars typically located at the ends of complex glycoconjugates on the surface of cells. They can be attached to a wide variety of proteins and lipids (McMillan and Crocker, 2008).

Siglec-15 is one of the most recently described Siglec family members that has a high homology to Siglec-14 (Angata et al., 2007). These authors reported that it preferentially binds to sialyl Tn structure and that it interacts with DAP12 and DAP10. The functional significance of these interactions is not known but it was proposed that Siglec-15 probably harbors an activating function (Angata et al., 2007). A recent publication showed that the presence of sialic acid at the end of surface glycoconjugates was required for proper osteoclast differentiation and were probably important for the fusion of osteoclast precursor cells (Takahata et al., 2007). This last observation creates a direct functional link between sialic acid binding and the expression of Siglec-15 in differentiating osteoclasts and strongly suggested that Siglec-15 plays a role in the early differentiation program of osteoclast precursors.

Thus, the expression profile of Siglec-15, its strong inducibility during osteoclast differentiation, its localization at the surface of the membrane, and its structural features all contribute to the feasibility of targeting this protein at the cell surface with monoclonal antibodies. The only other example of monoclonal antibody-based therapy that target osteoclasts is denosumab, a human monoclonal antibody that is specific for RANKL (Ellis et al. 2008). The present invention relates to the use of anti-Siglec-15 antibodies or antigen binding fragments as blockers of osteoclast differentiation and which may be used for impairing bone loss or bone resorption in bone-related diseases, such as cancer-induced severe bone loss.

The present description refers to a number of documents, the content of which is herein incorporated by reference in their entirety.

SUMMARY OF THE INVENTION

The present invention relates in one aspect to a therapeutic antibody and antigen binding fragments thereof which targets SIGLEC-15 or SIGLEC-15 analogues. These antibodies or antigen binding fragments may be advantageously recombinantly expressed in a mammalian cell system.

The present invention relates in another aspect thereof to an isolated antibody or antigen binding fragment capable of binding to a polypeptide able to promote osteoclast differentiation and of interfering with (e.g., inhibiting) an osteoclast differentiation activity of the polypeptide. One such particular polypeptide may be, for example, SEQ ID NO.:2 or a variant having at least 80% sequence identity with SEQ ID NO.:2. The antibody or antigen binding fragment may particularly bind to the extracellular region of SEQ ID NO.:2 or of the SEQ ID NO.:2 variant. The antibody or antigen binding fragment may thus modulate the differentiation of osteoclast precursor cells into differentiated osteoclasts that occurs through the SEQ ID NO.:2 or its variant.

Antibodies or antigen binding fragments that are encompassed by the present invention include, for example, those that may interfere with (e.g., inhibit) the differentiation of a human osteoclast precursor cell or more specifically, those that may interfere with (e.g., inhibit) the differentiation of a primary human osteoclast precursor cell.

Therefore, in accordance with the present invention, the antibody or antigen binding fragment may be capable of inhibiting differentiation of osteoclast precursor cells into differentiated osteoclasts.

In an embodiment of the invention, the antibody may be, for example, a polyclonal antibody. In another embodiment of the invention, the antibody or antigen binding fragment may be, for example, a monoclonal antibody or a fragment thereof. In yet another embodiment, the antibody or antigen binding fragment may be, for example, a chimeric antibody or a fragment thereof. In a further embodiment, the antibody or antigen binding fragment may be, for example, an isolated human antibody or a fragment thereof.

The antibody or antigen binding fragment of the present invention may be produced from an isolated mammalian cell or by a hybridoma cell. Although hybridoma cells are encompassed by the present invention, the antibody or antigen binding fragment may preferably be produced in a cell other than an hybridoma cell. The isolated mammalian cell may be, for instance, a human cell.

An exemplary embodiment of an antibody or antigen binding fragment of the present invention is one that may comprise (amino acids of) a constant region of a human antibody or a fragment thereof.

Another exemplary embodiment of an antibody or antigen binding fragment of the present invention is one that may comprise (amino acids of) a framework region of a human antibody.

Antibodies or antigen binding fragments that are especially encompassed by the present invention include those that comprises (amino acids of) a constant region of a human antibody or a fragment thereof and/or those that comprises (amino acids of) a framework region of a human antibody and that are produced in mammalian cells, or more particularly in human cells.

Yet other antibodies or antigen binding fragments that are especially encompassed by the present invention include monoclonal antibodies or those that comprises (amino acids of) a constant region of a human antibody or a fragment thereof and/or those that comprises (amino acids of) a framework region of a human antibody and that may interfere with (e.g., inhibit) the differentiation of human osteoclast precursor cells into differentiated human osteoclast, or more particularly those that may interfere with (e.g., inhibit) the differentiation of primary human osteoclast precursor cells into differentiated human osteoclast.

Yet further antibodies or antigen binding fragments that are especially encompassed by the present invention include monoclonal antibodies or those that comprises (amino acids of) a constant region of a human antibody or a fragment thereof and/or those that comprises (amino acids of) a framework region of a human antibody and that may interfere with (e.g., inhibit) the differentiation of human osteoclast precursor cells into differentiated human osteoclast, or more particularly those that may interfere with (e.g., inhibit) the differentiation of primary human osteoclast precursor cells into differentiated human osteoclast and that are produced in mammalian cells, or more particularly in human cells.

Exemplary embodiments of antigen binding fragments include, for example, a FV (e.g., scFv), a Fab, a Fab' or a (Fab')$_2$.

In accordance with the present invention, the antibody or antigen binding fragment may comprise (amino acids of) constant region from an IgG1, IgG2, IgG3, or IgG4. More particularly, the (amino acids of) the constant region may be from an IgG2.

The present invention also provides in a further aspect, a pharmaceutical composition which may comprise an antibody or antigen binding fragment of the present invention and a pharmaceutically acceptable carrier.

More specifically, the present invention provides a pharmaceutical composition which may comprise:
  a. an isolated antibody or antigen binding fragment that may be capable of binding to a polypeptide able to promote osteoclast differentiation and of interfering with (e.g., inhibiting, impairing) an osteoclast differentiation activity of the polypeptide such as a polypeptide which may be selected from the group consisting of SEQ ID NO.:2 and a variant having at least 80% sequence identity with SEQ ID NO.:2, and;
  b. a pharmaceutically acceptable carrier.

The pharmaceutical composition may thus comprise an antibody or antigen binding fragment that may impair (interfere with) the differentiation of osteoclast precursor cells into differentiated osteoclasts promoted by SEQ ID NO.:2 or its variant.

Exemplary embodiments of antibodies or antigen binding fragments that are encompassed by the present invention, include for example, a polyclonal antibody, a monoclonal antibody, a chimeric antibody, a human antibody or a fragment thereof.

Exemplary embodiments of pharmaceutical compositions are those which comprises an antibody or antigen binding fragment that is produced from an isolated mammalian cell such as a human cell.

Exemplary embodiments of pharmaceutical compositions are those which comprises an antibody or antigen binding fragment that may interfere with the differentiation of human osteoclast precursor cells into differentiated osteoclasts.

Other exemplary embodiments of pharmaceutical compositions are those which comprises an antibody or antigen binding fragment that may interfere with the differentiation of primary human osteoclast precursor cells into differentiated osteoclasts.

Yet other exemplary embodiments of pharmaceutical compositions are those which comprises an antibody or antigen binding fragment that interfere with the differentiation of human osteoclast precursor cells (e.g., primary human osteoclast precursors cells) into differentiated osteoclasts and that are produced in mammalian cells (e.g., human cells).

In an additional aspect, the present invention provides an isolated cell which may comprise (e.g., that has been injected or transformed or else), that is capable of expressing or that may express an antibody or antigen binding fragment of the present invention. In accordance with the present invention, the isolated cell may be, for instance a mammalian cell. In a more specific embodiment, the isolated cell may be, for example, a human cell.

In yet an additional aspect, the present invention relates to a method of modulating (i.e., inhibiting, lowering, impairing) osteoclast differentiation in a mammal in need, the method may comprise administering the antibody or antigen binding fragment of the present invention.

In an exemplary embodiment, the invention provides a method of modulating (i.e., inhibiting, lowering, impairing) osteoclast differentiation in a mammal in need, the method may comprise administering an antibody or antigen binding fragment that may be capable of modulating the differentiation of an osteoclast precursor cell (e.g., human osteoclast precursor cell, human primary osteoclast precursor cell) into a differentiated osteoclast.

In another exemplary embodiment, the invention provides a method of modulating (i.e., inhibiting, lowering, impairing) osteoclast differentiation in a mammal in need, the method may comprise administering an antibody or antigen binding fragment that may be capable of modulating the differentiation of an osteoclast precursor cell (e.g., human osteoclast precursor cell, human primary osteoclast precursor cell) into a differentiated osteoclast and that is produced in mammalian cells (e.g., human cell).

In yet another exemplary embodiment, the invention provides a method of modulating (i.e., inhibiting, lowering, impairing) osteoclast differentiation in a mammal in need, the method may comprise administering an antibody or antigen binding fragment that is capable of modulating (i.e., inhibiting, lowering, impairing) the differentiation of an osteoclast precursor cell (e.g., human osteoclast precursor cell, human primary osteoclast precursor cell) into a differentiated osteoclast, where the antibody or antigen binding fragment may comprise, for example, a monoclonal antibody or a fragment thereof or that may comprise (amino acids) of a human constant region or a fragment thereof, and/or amino acids of a framework region of a human antibody. Such antibodies or antigen binding fragments include those that are produced in mammalian cells (e.g., human cell).

The antibody or antigen binding fragment of the present invention may thus be administered to a mammal (e.g., human) which may suffer from undesirable (e.g., excessive) bone loss or bone resorption. The antibody or antigen binding fragment may thus be particularly useful to treat bone loss or bone resorption in patients suffering or susceptible of suffering from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets) or other form of vitamin D deficiency such as vitamin D deficiency associated with chronic kidney disease or kidney failure, fibrogenesis imperfecta ossium, osteosclerotic disorders such as pycnodysostosis and damage caused by macrophage-mediated inflammatory processes.

The present invention also provides in a further aspect, a method of identifying an therapeutic antibody or antigen binding fragment able to impair an osteoclast differentiation activity of a polypeptide such as, for example, SEQ ID NO.:2 or a variant having at least 80% sequence identity with SEQ ID NO.:2. The method may comprise contacting the polypeptide or a cell expressing the polypeptide with a candidate antibody or antigen binding fragment and measuring the activity of the polypeptide. A reduction in the osteoclast differentiation activity (in the presence of antibody or antibody fragment in comparison with the absence of antibody or antibody fragment) may thus positively identify an inhibitory antibody or antigen binding fragment.

The present invention also relates in a further aspect to an antibody or antigen binding fragment which may be capable of inhibiting differentiation of an osteoclast precursor cell into an osteoclast and which may be obtained by the method of providing an antibody or antigen binding fragment able to bind to the polypeptide described herein (SEQ ID NO.:2 or to a variant having at least 80% sequence identity with SEQ ID NO.:2) to an osteoclast precursor cell and inducing differentiation. A reduced osteoclast differentiation (in the presence of antibody or antibody fragment in comparison with the absence of antibody or antibody fragment) may thus positively identify an antibody or antigen binding fragment which may be capable of inhibiting differentiation of an osteoclast precursor cell into an osteoclast.

The present invention also relates to an isolated antibody or antigen binding fragment which may be capable of specific binding to SEQ ID NO.:2 or to a variant having at least 80% sequence identity with SEQ ID NO.:2 and of inhibiting a resorptive activity of an osteoclast.

The invention also provides a method of generating an antibody or antigen binding fragment which may be capable of inhibiting differentiation of an osteoclast precursor cell (into an osteoclast) or of inhibiting a resorptive activity of an osteoclast. The method may comprise administering SEQ ID NO.:2, a variant having at least 80% identity with SEQ ID NO.:2 or a fragment of at least 10 amino acids thereof, to a mammal (e.g., especially an animal) under conditions allowing for the production of antibodies (under conditions which induces humoral immunity). The method may also comprise isolating or purifying the antibody or antigen binding fragment from the mammal.

The invention additionally provides an antibody or antigen binding fragment that comprises at least one CDRL1, CDRL2, CDRL3, CDRH1, CDRH2 and/or CDRH3 described herein. Identification of CDRs in a light chain or heavy chain may be made in accordance with the Kabat or Chotia method or by other methods known in the art In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

In accordance with the present invention, the antibody or antigen binding fragment may comprise at least two CDRs of a CDRH1, a CDRH2 or a CDRH3.

Also in accordance with the present invention, the antibody or antigen binding fragment may comprise one CDRH1, one CDRH2 and one CDRH3.

Further in accordance with the present invention, the antibody or antigen binding fragment may comprise:
a. At least two CDRs of a CDRL1, CDRL2 or CDRL3 and;
b. At least two CDRs of a CDRH1, one CDRH2 or one CDRH3.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

The invention further provides antibody or antigen binding fragment that comprises amino acids of the light chain variable region and/or of the heavy chain variable region described herein.

The present invention relates to polynucleotides comprising sequences involved in the process of bone remodeling, the open reading frame of such sequences, substantially identical sequences (e.g., variants (e.g., allelic variant), non human orthologs), substantially complementary sequences and fragments of any one of the above thereof.

The present invention relates to polypeptide comprising sequences involved in the process of bone remodeling including biologically active analogs and biologically active fragments thereof. The present invention also relates to compositions that are useful for the diagnosis, prognosis, treatment, prevention and/or evaluation of therapies for bone remodeling and associated disorders.

In addition, the present invention relates to a method for analyzing polynucleotide expression patterns, and applied in the identification of polynucleotides, polypeptides, variants and derivatives specifically involved in bone remodeling.

The present invention relates to polynucleotide expression profiles of osteoclasts, the isolation and identification of polynucleotides, their corresponding polypeptides, variants and derivatives involved in osteoclast activity, validation of these identified elements for their potential as therapeutic targets and use of said polynucleotides, polypeptides, variants and derivatives for the amelioration of disease states.

It is an object of the present invention to provide polynucleotides and/or related polypeptides that have been isolated and identified. More specifically, the invention provides (isolated or substantially purified) polynucleotides comprising or consisting of any one of SEQ ID NO.:1, its coding sequence (open reading frame) substantially identical sequence (e.g., variants, orthologs (e.g., SEQ ID NO.:3; SEQ ID NO.:107)), substantially complementary sequences and related polypeptides comprising any one of SEQ ID NO.:2, SEQ ID NO.:4 or SEQ ID NO.:108 which have been shown to be upregulated in a highly specific fashion in osteoclasts.

NSEQ refers generally to polynucleotide sequences of the present invention and includes for example, SEQ. ID. NO.:1, SEQ ID NO.:3 and SEQ ID NO.:107 whereas PSEQ refers generally to polypeptide sequences of the present invention and includes, for example, SEQ ID NO.:2 or a SEQ ID NO.:2 variant (including SEQ ID NO.:4 and SEQ ID NO.:108). Of course it will be understood that NSEQ also encompasses polynucleotide sequences which are designed or derived from SEQ. ID. NO.:1, SEQ ID NO.:3 or and SEQ ID NO.:107 including for example, their coding sequence, complementary sequences etc.

As used herein the term "NSEQ" refers generally to polynucleotides sequences comprising or consisting of any one of SEQ. ID. NO.:1, SEQ ID NO.:3, or SEQ ID NO.:107 (e.g., an isolated form) or comprising or consisting of a fragment of any one of SEQ. ID. NO.:1, SEQ ID NO.:3 or SEQ ID NO.:107. The term "NSEQ" more particularly refers to a polynucleotide sequence comprising or consisting of a transcribed portion of any one of SEQ. ID. NO.:1, SEQ ID NO.:3 or SEQ ID NO.:107, which may be, for example, free of untranslated or untranslatable portion(s) (i.e., a coding portion of any one of SEQ ID No.:1, SEQ ID NO.:3 or SEQ ID NO.:107). The term "NSEQ" additionally refers to a sequence substantially identical to any one of the above and more particularly substantially identical to polynucleotide sequence comprising or consisting of a transcribed portion of any one of SEQ. ID. Nos.: 1 or 3, which may be, for example, free of untranslated or untranslatable portion(s). The term "NSEQ" additionally refers to a polynucleotide sequence region of any one of SEQ. ID. NO.:1, SEQ ID NO.:3 or SEQ ID NO.:107 which encodes or is able to encode a polypeptide. The term "NSEQ" also refers to a polynucleotide sequence able of encoding any one of the polypeptides described herein or a polypeptide fragment of any one of the above. Finally, the term "NSEQ" also comprise a sequence substantially complementary to any one of the above.

The term "inhibitory NSEQ" generally refers to a sequence substantially complementary to any one of SEQ. ID. NO.:1, SEQ ID NO.: 3 or SEQ ID NO.:107, substantially complementary to a fragment of any one of SEQ. ID. NO.:1, SEQ ID NO.:3 or SEQ ID NO.:107, substantially complementary to a sequence substantially identical to SEQ. ID. NO.:1, SEQ ID NO.:3 or SEQ ID NO.:107 and more particularly, substantially complementary to a transcribed portion of any one of SEQ. ID. NO.:1, SEQ ID NO.:3 or SEQ ID NO.:107 (e.g., which may be free of unstranslated or untranslatable portion) and which may have attenuating or even inhibitory action against the transcription of a mRNA or against expression of a polypeptide encoded by a corresponding SEQ ID NO.:1, SEQ ID NO.:3 or SEQ ID NO.:107. Suitable "inhibitory NSEQ" may have for example and without limitation from about 10 to about 30 nucleotides, from about 10 to about 25 nucleotides or from about 15 to about 20 nucleotides. As used herein the term "nucleotide" means deoxyribonucleotide or ribonucleotide. In an exemplary embodiment, the use of nucleotide analogues is also encompassed in the present invention.

The present invention relates in one aspect thereof to an isolated polynucleotide sequence having at least from about 80% to about 100% (e.g., 80%, 90%, 95%, etc.) sequence identity to a polynucleotide sequence selected from the group consisting of polynucleotides comprising (a) any one of a SEQ. ID. NO.:1, SEQ ID NO.:3 or SEQ ID NO.:107; (b) an open reading frame of (a); (c) a full complement of (a) or (b), and; (d) a fragment of any one of (a) to (c).

As used herein the term "unstranscribable region" may include for example, a promoter region (or portion thereof), silencer region, enhancer region etc. of a polynucleotide sequence.

As used herein the term "unstranslatable region" may include for example, an initiator portion of a polynucleotide sequence (upstream of an initiator codon, e.g., AUG), intronic regions, stop codon and/or region downstream of a stop codon (including polyA tail, etc.).

Complements of the isolated polynucleotide sequence encompassed by the present invention may be those, for example, which hybridize under high stringency conditions to any of the nucleotide sequences in (a), or (b). The high stringency conditions may comprise, for example, a hybridization reaction at 65° C. in 5×SSC, 5×Denhardt's solution, 1% SDS, and 100 µg/ml denatured salmon sperm DNA.

In accordance with the present invention, the polynucleotide sequence may be used, for example, in the treatment of diseases or disorders involving bone remodeling.

Fragments of polynucleotides may be used, for example, as probes for determining the presence of the isolated polynucleotide (or its complement or fragments thereof) in a sample, cell, tissue, etc. for experimental purposes or for the purpose of diagnostic of a diseases or disorders involving bone remodeling.

The present invention also relates to a combination comprising a plurality of polynucleotides (substantially purified and/or isolated). The polynucleotides may be co-expressed with one or more genes known to be involved in bone remodeling. Furthermore, the plurality of polynucleotides may be selected, for example, from the group consisting of a polynucleotide comprising (a) any one of SEQ. ID. NO.:1, SEQ ID NO.:3 or SEQ ID NO.:107; (b) an open reading frame of (a); (c) a polynucleotide sequence comprising or consisting of a transcribed portion of any one of SEQ. ID. NO.:1, SEQ ID NO.:3 or SEQ ID NO.:107, which may be, for example, free of untranslated or untranslatable portion(s) (d) a complementary sequence of any one of (a) to (c); (e) a sequence that hybridizes under high stringency conditions to any one of the nucleotide sequences of (a) to (d) and; (f) fragments of any one of (a) to (e).

The present invention further relates to a polynucleotide encoding any one of the polypeptides described herein. In accordance with the present invention, the polynucleotide (RNA, DNA, etc.) may encode a polypeptide which may be selected from the group consisting of any one of SEQ ID NO.:2 or a SEQ ID NO.:2 analogue such as, for example, SEQ ID NO.:4 or SEQ ID NO.:108, or fragments thereof (e.g., biologically active fragments, immunologically active fragments, etc.).

The present invention also relates to an isolated nucleic acid molecule comprising the polynucleotides of the present invention, operatively linked to a nucleotide sequence encoding a heterologous polypeptide thereby encoding a fusion polypeptide.

The invention further relates to a polypeptide encoded by a polynucleotide of SEQ. ID. NO.:1, SEQ ID NO.:3 or SEQ ID NO.:107 or more particularly from the open reading frame of any one of SEQ. ID. NO.:1, SEQ ID NO.:3 or SEQ ID NO.:107, or a portion thereof. The invention also comprises the product of a gene that is co-expressed with one or more genes known to be involved in bone remodeling.

Isolated naturally occurring allelic variant are also encompassed by the present invention as well as synthetic variants (e.g., made by recombinant DNA technology or by chemical synthesis, etc.) such as biologically active variant which may comprise one or more amino acid substitutions (compared to a naturally occurring polypeptide), such as conservative or non conservative amino acid substitution.

The present invention, further provides a vector (mammalian, bacterial, viral, etc.) comprising the polynucleotides described herein or fragments thereof, such as an expression vector. The vector may further comprise a nucleic acid sequence which may help in the regulation of expression of the polynucleotide and/or a nucleotide sequence encoding a tag (e.g., affinity tag; HA, GST, His etc.).

In accordance with the present invention, an expression vector may comprise, for example, the following operatively linked elements:

a) a transcription promoter;
b) a polynucleotide segment (which may comprise an open reading frame of any one of SEQ ID NO.:1, SEQ ID NO.:3 or SEQ ID NO.:107); and
c) a transcription terminator.

The invention also relates to an expression vector comprising a polynucleotide described herein, a host cell transformed with the expression vector and a method for producing a polypeptide of the present invention.

The invention further relates to a vector comprising a polynucleotide or polynucleotide fragment. Vectors which may comprise a sequence substantially complementary to the polynucleotides of the present invention (e.g., siRNA, shRNA) are thus encompassed by the present invention. The vector may comprise sequences enabling transcription of the polynucleotide or polynucleotide fragment.

More particularly, the present invention therefore provides a cell which may be genetically engineered to contain and/or to express the polynucleotide (including complements and fragments) and/or polypeptides of the present invention. The cell may be, for example, a mammalian cell, an insect cell, a bacteria cell, etc.

The present invention therefore provides a host cell which may comprise a vector as described herein. The cell may be, for example, a mammalian cell, an insect cell, a bacteria, etc. The cell may be able to express or expresses a polypeptide encoded by the polynucleotide described herein.

Methods of producing the polypeptides of the present invention encompassed herewith includes for example, culturing the cell in conditions allowing the transcription of a gene or expression of the polypeptide. The polypeptide may be recovered, for example, from cell lysate or from the cell supernatant.

The invention relates to the use of at least one polynucleotide comprising any one of SEQ. ID. NO.:1, SEQ ID NO.:3 or SEQ ID NO.:107 their coding sequence, substantially identical sequences, substantially complementary sequences or fragments thereof on an array. The array may be used in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder. Of course, the use of a polynucleotide of the present invention in a diagnosis method is not dependent exclusively by way of a specific assay. The sequence or sequences may be used in conventionally used diagnosis methods known in the art.

The present invention also relates to a method of ameliorating bone remodeling disease or disorder symptoms, or for inhibiting or delaying bone disease or disorder, the method may comprise: contacting a compound capable of specifically inhibiting activity or expression of a polynucleotide sequence described herein or a polypeptide described herein, in osteoclasts so that symptoms of the bone remodeling disease or disorder may be ameliorated, or the disease or disorder may be prevented, delayed or lowered.

The present invention further relates to a method for ameliorating bone remodeling disease or disorder symptoms, or for inhibiting or delaying bone disease or disorder, the method may comprise: contacting a compound capable of specifically promoting activity or expression of a polynucleotide sequence described herein or a polypeptide described herein, in osteoclasts so that symptoms of the bone remodeling disease or disorder may be ameliorated, or the disease or disorder may be prevented, delayed or lowered.

The present invention also relates to a method of treating a condition in a mammal characterized by a deficiency in, or need for, bone growth or replacement and/or an undesirable level of bone resorption, which method may comprise administering to a mammalian subject in need of such treatment an effective amount of a suitable compound described herein.

The present invention further relates to a method of using a polynucleotide sequence described herein, a polypeptide described herein on an array and for the use of the array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample may indicate the presence of a bone remodeling disease or disorder.

In accordance with the present invention, the polynucleotide sequence described herein may be used for somatic cell gene therapy or for stem cell gene therapy.

The invention also relates to a pharmaceutical composition comprising a polynucleotide described herein or a polypeptide encoded by the selected polynucleotide or portion thereof and a suitable pharmaceutical carrier.

Additionally, the invention relates to products, compositions, processes and methods that comprise a polynucleotide described herein, a polypeptide encoded by the polynucleotides, a portion thereof, their variants or derivatives, for research, biological, clinical and therapeutic purposes.

The NSEQs and PSEQs may be used in diagnosis, prognosis, treatment, prevention, and selection and evaluation of therapies for diseases and disorders involving bone remodeling including, but not limited to, osteoporosis, osteopenia, osteomalacia, hyperparathyroidism, hyperthyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

Use of NSEQ as a Screening Tool

The polynucleotides obtained by the present invention may be used to detect and isolate expression products, for example, mRNA, complementary DNAs (cDNAs) and proteins derived from or homologous to the NSEQs. In one embodiment, the expression of mRNAs homologous to the NSEQs of the present invention may be detected, for example, by hybridization analysis, reverse transcription and in vitro nucleic acid amplification methods. Such procedures permit detection of mRNAs in a variety of tissue types or at different stages of development. The subject nucleic acids which are expressed in a tissue-specific or a developmental-stage-specific manner are useful as tissue-specific markers or for defining the developmental stage of a sample of cells or tissues that may define a particular disease state. One of skill in the art may readily adapt the NSEQs for these purposes.

Those skilled in the art will also recognize that the NSEQs and its expression products such as cDNA nucleic acids and genomic DNA may be used to prepare short oligonucleotides sequences. For example, oligonucleotides having ten to twelve nucleotides or more may be prepared which hybridize specifically to the present NSEQs and cDNAs and allow detection, identification and isolation of unique nucleic sequences by hybridization. Sequences of for example, at least 15-20 nucleotides may be used and selected from regions that lack homology to other known sequences. Sequences of 20 or more nucleotides that lack such homology show an increased specificity toward the target sequence. Useful hybridization conditions for probes and primers are readily determinable by those of skill in the art. Stringent hybridization conditions encompassed herewith are those that may allow hybridization of nucleic acids that are greater than 90% homologous but which may prevent hybridization of nucleic acids that are less than 70% homologous. The specificity of a probe may be determined by whether it is made from a unique region, a regulatory region, or from a conserved motif. Both probe specificity and the stringency of diagnostic hybridization or amplification (maximal, high, intermediate, or low) reactions may be determined whether the probe identifies exactly complementary sequences, allelic variants, or related sequences. Probes designed to detect related sequences may have at least 50% sequence identity to any of the selected polynucleotides.

It is to be understood herein that the NSEQs (including substantially identical sequences and fragments thereof) may hybridize to a substantially complementary sequence found in a test sample. Additionally, a sequence substantially complementary to NSEQ may bind a NSEQ found in a test sample.

Furthermore, a probe may be labelled by any procedure known in the art, for example by incorporation of nucleotides linked to a "reporter molecule". A "reporter molecule", as used herein, may be a molecule that provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes may be conjugated to avidin or streptavidin for use with a biotinylated probe. Similarly, probes may be conjugated to avidin or streptavidin for use with a biotinylated enzyme. Incorporation of a reporter molecule into a DNA probe may be by any method known to the skilled artisan, for example by nick translation, primer extension, random oligo priming, by 3' or 5' end labeling or by other means. In addition, hybridization probes include the cloning of nucleic acid sequences into vectors for the production of mRNA probes. Such vectors are known in the art, are commercially available, and may be used to synthesize RNA probes in vitro. The labelled polynucleotide sequences may be used in Southern or northern analysis, dot blot, or other membrane-based technologies; in PCR technologies; and in micro arrays utilizing samples from subjects to detect altered expression. Oligonucleotides useful as probes for screening of samples by hybridization assays or as primers for amplification may be packaged into kits. Such kits may contain the probes or primers in a pre-measured or pre-determined amount, as well as other suitably packaged reagents and materials needed for the particular hybridization or amplification protocol. In another embodiment, the invention entails a substantially purified polypeptide encoded by the polynucleotides of NSEQs, polypeptide analogs or polypeptide fragments thereof. The polypeptides whether in a premature, mature or fused form, may be isolated from lysed cells, or from the culture medium, and purified to the extent needed for the intended use. One of skill in the art may readily purify these proteins, polypeptides and peptides by any available procedure. For example, purification may be accomplished by salt fractionation, size exclusion chromatography, ion exchange chromatography, reverse phase chromatography, affinity chromatography and the like.

Use of NSEQ for Development of an Expression System

In order to express a biologically active polypeptide, NSEQ, or derivatives thereof, may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, NSEQ may be transformed into cell lines using expression vectors that may contain viral origins of replication and/or endogenous expression elements and a selectable or visible marker gene on the same or on a separate vector. The invention is not to be limited by the vector or host cell employed.

In general, host cells that contain NSEQ and that express a polypeptide encoded by the NSEQ, or a portion thereof, may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

The present invention additionally relates to a bioassay for evaluating compounds as potential antagonists of the polypeptide described herein, the bioassay may comprise:
  a) culturing test cells in culture medium containing increasing concentrations of at least one compound whose ability to inhibit the action of a polypeptide described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter
  b) monitoring in the cells the level of expression of the product of the reporter gene as a function of the concentration of the potential antagonist compound in the culture medium, thereby indicating the ability of the potential antagonist compound to inhibit activation of the polypeptide encoded by, the polynucleotide sequence described herein.

The present invention further relates to a bioassay for evaluating compounds as potential agonists for a polypeptide encoded by the polynucleotide sequence described herein, the bioassay may comprise:
  a) culturing test cells in culture medium containing increasing concentrations of at least one compound whose ability to promote the action of the polypeptide encoded by the polynucleotide sequence described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter
  b) monitoring in the cells the level of expression of the product of the reporter gene as a function of the concentration of the potential agonist compound in the culture medium, thereby indicating the ability of the potential agonist compound to promote activation of a polypeptide encoded by the polynucleotide sequence described herein.

Host cells transformed with NSEQ may be cultured under conditions for the expression and recovery of the polypeptide from cell culture. The polypeptide produced by a transgenic cell may be secreted or retained intracellularly depending on the sequence and/or the vector used. As will be understood by those of skill in the art, expression vectors containing NSEQ may be designed to contain signal sequences that direct secretion of the polypeptide through a prokaryotic or eukaryotic cell membrane. Due to the inherent degeneracy of the genetic code, other DNA sequences that encode substantially the same or a functionally equivalent amino acid sequence may be produced and used to express the polypeptide encoded by NSEQ. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and monoclonal antibody epitopes.

In yet a further aspect, the present invention relates to an isolated polynucleotide which may comprise a nucleotide sequence encoding a fusion protein, the fusion protein may comprise a fusion partner fused to a peptide fragment of a protein encoded by, or a naturally occurring allelic variant polypeptide encoded by, the polynucleotide sequence described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Use of NSEQ as a Diagnostic Screening Tool

The skilled artisan will readily recognize that NSEQ may be used for diagnostic purposes to determine the absence, presence, or altered expression (i.e. increased or decreased compared to normal) of the gene. The polynucleotides may be at least 10 nucleotides long or at least 12 nucleotides long or at least 15 nucleotides long up to any desired length and may comprise complementary RNA and DNA molecules, branched nucleic acids, and/or peptide nucleic acids (PNAs). In one alternative, the polynucleotides may be used to detect and quantify gene expression in samples in which expression of NSEQ is correlated with disease. In another alternative, NSEQ may be used to detect genetic polymorphisms associated with a disease. These polymorphisms may be detected in the transcript cDNA.

The invention provides for the use of at least one polynucleotide comprising NSEQ (e.g., an open reading frame of NSEQ, a substantially complementary sequence, a substantially identical sequence, and fragments thereof) on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder.

In another embodiment, the present invention provides one or more compartmentalized kits for detection of bone resorption disease states. A first kit may have a receptacle containing at least one isolated probe. Such a probe may be a nucleic acid fragment which is present/absent in the genomic DNA of normal cells but which is absent/present in the genomic DNA of affected cells. Such a probe may be specific for a DNA site that is normally active/inactive but which may be inactive/active in certain cell types. Similarly, such a probe may be specific for a DNA site that may be abnormally expressed in certain cell types. Finally, such a probe may identify a specific DNA mutation. By specific for a DNA site is meant that the probe may be capable of hybridizing to the DNA sequence which is mutated, or may be capable of hybridizing to DNA sequences adjacent to the mutated DNA sequences. The probes provided in the present kits may have a covalently attached reporter molecule. Probes and reporter molecules may be readily prepared as described above by those of skill in the art.

Use of NSEQ as a Therapeutic

One of skill in the art will readily appreciate that the expression systems and assays discussed above may also be used to evaluate the efficacy of a particular therapeutic treatment regimen, in animal studies, in clinical trials, or to monitor the treatment of an individual subject. Once the presence of disease is established and a treatment protocol is initiated, hybridization or amplification assays may be repeated on a regular basis to determine if the level of expression in the patient begins to approximate the level observed in a healthy subject. The results obtained from successive assays may be used to show the efficacy of treatment over a period ranging from several days to many years.

In yet another aspect of the invention, an NSEQ, a portion thereof, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art may be used to construct vectors to express nucleic acid sequences or their complements.

Alternatively, NSEQ, a portion thereof, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods that are well known in the art. Additionally, endogenous NSEQ expression may be inactivated using homologous recombination methods that insert an inactive gene sequence into the coding region or other targeted region of NSEQ.

Depending on the specific goal to be achieved, vectors containing NSEQ may be introduced into a cell or tissue to express a missing polypeptide or to replace a non-functional polypeptide. Of course, when one wishes to express PSEQ in a cell or tissue, one may use a NSEQ able to encode such PSEQ for that purpose or may directly administer PSEQ to that cell or tissue.

On the other hand, when one wishes to attenuate or inhibit the expression of PSEQ, one may use a NSEQ (e.g., an inhibitory NSEQ) which is substantially complementary to at least a portion of a NSEQ able to encode such PSEQ.

The expression of an inhibitory NSEQ may be done by cloning the inhibitory NSEQ into a vector and introducing the vector into a cell to down-regulate the expression of a polypeptide encoded by the target NSEQ.

Vectors containing NSEQ (e.g., including inhibitory NSEQ) may be transformed into a cell or tissue to express a missing polypeptide or to replace a non-functional polypeptide. Similarly a vector constructed to express the complement of NSEQ may be transformed into a cell to down-regulate the over-expression of a polypeptide encoded by the polynucleotides of NSEQ, or a portion thereof. Complementary or anti-sense sequences may consist of an oligonucleotide derived from the transcription initiation site; nucleotides between about positions −10 and +10 from the ATG are preferred. Similarly, inhibition may be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. 1994)

Ribozymes, enzymatic RNA molecules, may also be used to catalyze the cleavage of mRNA and decrease the levels of particular mRNAs, such as those comprising the polynucleotide sequences of the invention. Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

In addition to the active ingredients, a pharmaceutical composition may contain pharmaceutically acceptable carriers comprising excipients and auxiliaries that facilitate processing of the active compounds into preparations that may be used pharmaceutically.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Use of NSEQ in General Research

The invention finally provides products, compositions, processes and methods that utilize an NSEQ, their open reading frame, or a polypeptide encoded by the polynucleotides of NSEQ or their open reading frame, or a portion thereof, their variants, analogs, derivatives and fragments for research, biological, clinical and therapeutic purposes. For example, to identify splice variants, mutations, and polymorphisms NSEQ may be extended utilizing a partial nucleotide sequence and employing various PCR-based methods known in the art to detect upstream sequences such as promoters and other regulatory elements. Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence.

The polynucleotides may also be used as targets in a microarray. The micro-array may be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genomic level.

In yet another embodiment, polynucleotides may be used to generate hybridization probes useful in mapping the naturally occurring genomic sequence. Fluorescent in situ hybridization (FISH) may be correlated with other physical chromosome mapping techniques and genetic map data.

The present invention more particularly relates in one aspect thereof to a method of representatively identifying an endogeneously differentially expressed sequence involved in osteoclast differentiation. The sequence may be, for example, differentially expressed in a differentiated osteoclast cell compared to an undifferentiated osteoclast precursor cell.

The method of the present invention may comprise;
  a) separately providing total messenger RNA from (mature or intermediately) differentiated human osteoclast cell and undifferentiated human osteoclast precursor cell, the total messenger RNA may comprise, for example, at least one endogeneously differentially expressed sequence,
  b) generating single-stranded cDNA from each messenger RNA of differentiated human osteoclast cell and (e.g., randomly) tagging the 3'-end of the single-stranded cDNA with a RNA polymerase promoter sequence and a first sequence tag;
  c) generating single-stranded cDNA from each messenger RNA of undifferentiated human osteoclast precursor cell and (e.g., randomly) tagging the 3'-end of the single-stranded cDNA with a RNA polymerase promoter sequence and a second sequence tag;
  d) separately generating partially or completely double-stranded 5'-tagged-DNA from each of b) and c), the double-stranded 5'-tagged-DNA may thus comprise in a 5' to 3' direction, a double-stranded RNA polymerase promoter, a first or second sequence tag and an endogenously expressed sequence,
  e) separately linearly amplifying a first and second tagged sense RNA from each of d) with a RNA polymerase enzyme (which may be selected based on the promoter used for tagging),
  f) generating single-stranded complementary first or second tagged DNA from one of e),
  g) hybridizing the single-stranded complementary first or second tagged DNA of
  f) with the other linearly amplified sense RNA of e), h) recovering unhybridized RNA with the help of the first or second sequence tag (for example by PCR or hybridization), and;
i) identifying (determining) the nucleotide sequence of unhybridized RNA.

Steps b) and/or c), may comprise generating a single copy of a single-stranded cDNA.

The method may further comprise the step of comparatively determining the presence of the identified endogeneously and differentially expressed sequence in a differentiated osteoclast cell relative to an undifferentiated osteoclast precursor cell.

A sequence which is substantially absent (e.g., totally absent or present in very low quantity) from one of differentiated osteoclast cell or an undifferentiated osteoclast precursor cell and present in the other of differentiated osteoclast cell or an undifferentiated osteoclast precursor cell may therefore be selected.

The sequence thus selected may be a positive regulator of osteoclast differentiation and therefore may represent an attractive target which may advantageously be used to promote bone resorption or alternatively such target may be inhibited to lower or prevent bone resorption.

Alternatively, the sequence selected using the above method may be a negative regulator of osteoclast differentiation and may therefore represent an attractive target which may advantageously be induced (e.g., at the level of transcription, translation, activity etc.) or provided to a cell to lower or prevent bone resorption. Also such negative regulator may, upon its inhibition, serve as a target to promote bone resorption.

In accordance with the present invention, the sequence may be further selected based on a reduced or substantially absent expression in other normal tissue, therefore representing a candidate sequence specifically involved in osteoclast differentiation and bone remodeling.

The method may also further comprise a step of determining the complete sequence of the nucleotide sequence and may also comprise determining the coding sequence of the nucleotide sequence.

The present invention also relates in a further aspect, to the isolated endogeneously and differentially expressed sequence (polynucleotide and polypeptide) identified by the method of the present invention.

More particularly, the present invention encompasses a polynucleotide which may comprise the identified polynucleotide sequence, a polynucleotide which may comprise the open reading frame of the identified polynucleotide sequence, a polynucleotide which may comprise a nucleotide sequence substantially identical to the polynucleotide identified by the method of the present invention, a polynucleotide which may comprise a nucleotide sequence substantially complementary to the polynucleotide identified by the method of the present invention, fragments and splice variant thereof.

In accordance with the present invention, the isolated endogeneously and differentially expressed sequence of the present invention may be a complete or partial RNA molecule.

Isolated DNA molecule able to be transcribed into the RNA molecule of the present invention are also encompassed herewith as well as vectors (including expression vectors) comprising the such DNA or RNA molecule.

The present invention also relates to libraries comprising at least one isolated endogeneously and differentially expressed sequence identified herein (e.g., partial or complete RNA or DNA, substantially identical sequences or substantially complementary sequences (e.g., probes) and fragments thereof (e.g., oligonucleotides)).

In accordance with the present invention, the isolated endogeneously and differentially expressed sequence may be selected, for example, from the group consisting of a polynucleotide which may consist in or comprise;
a) any one of SEQ ID NO.:1, SEQ ID NO.:3 or SEQ ID NO.:107,
b) the open reading frame of any one of SEQ ID NO.:1, SEQ ID NO.:3 or SEQ ID NO.:107,
c) a polynucleotide which may comprise a nucleotide sequence substantially identical to a) or b), and;
d) a polynucleotide which may comprise a nucleotide sequence substantially complementary to any one of a) to c),
e) fragments of any one of a) to d).

In a further aspect the present invention relates to a polypeptide which may be encoded by the isolated endogeneously and differentially expressed sequence of the present invention.

In yet a further aspect the present invention relates to a polynucleotide able to encode a polypeptide of the present invention. Due to the degeneracy of the genetic code, it is to be understood herein that a multiplicity of polynucleotide sequence may encode the same polypeptide sequence and thus are encompassed by the present invention.

Exemplary polypeptides may comprise a sequence selected from the group consisting of any one of SEQ ID NO.:2 and a SEQ ID NO.:2 variant (e.g., SEQ ID NO.:4, SEQ ID NO.:108).

The present invention also relates to an isolated non-human ortholog polynucleotide sequence (involved in bone remodeling), the open reading frame of the non-human ortholog, substantially identical sequences, substantially complementary sequences, fragments and splice variants thereof.

The present invention as well relates to an isolated polypeptide encoded by the non-human ortholog polynucleotide as well as biologically active analogs and biologically active fragments thereof.

Exemplary embodiments of non-human (e.g., mouse) ortholog polynucleotides encompassed herewith include, for example, SEQ ID NO.:3 or SEQ ID NO.:107.

Exemplary embodiments of isolated polypeptide encoded by some non-human orthologs identified herein include for example, a polypeptide such as SEQ ID NO.:4 or SEQ ID NO.:108.

Exemplary embodiments of SEQ ID NO.:2 variant having 80% identity with SEQ ID NO.:2 include for example and without limitation, SEQ ID NO.:4, SEQ ID NO.:108 as well as other analogues that are published in databases under gene bank accession numbers or NCBI reference sequence: AAY40743.1, XP_512109.2, XP_001089000.1, XP_601064.4, NP_001094508.1, XP_855238.1, XP_574176.2 and EAX01462.1.

The present invention also more particularly relates, in an additional aspect thereof, to an isolated polynucleotide which may be differentially expressed in differentiated osteoclast cell compared to undifferentiated human osteoclast precursor cell.

The isolated polynucleotide may comprise a member selected from the group consisting of;
a) a polynucleotide which may comprise any one of SEQ ID NO.:1, SEQ ID NO.:3 or SEQ ID NO.:107;
b) a polynucleotide which may comprise the open reading frame of any one of SEQ ID NO.:1, SEQ ID NO.:3 or SEQ ID NO.:107;

c) a polynucleotide which may comprise a transcribed or transcribable portion of any one of SEQ. ID. NO.:1, SEQ ID NO.:3 or SEQ ID NO.:107, which may be, for example, free of untranslated or untranslatable portion(s);

d) a polynucleotide which may comprise a translated or translatable portion of any one of SEQ. ID. NO.:1, SEQ ID NO.:3 or SEQ ID NO.:107 (e.g., coding portion), e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b) c) or d), f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d) and;

g) a fragment of any one of a) to f)

h) including polynucleotides which consist in the above.

Exemplary polynucleotides fragments of those listed above comprise polynucleotides of at least 10 nucleic acids which may be substantially complementary to the nucleic acid sequence of any one of SEQ ID NO.:1, SEQ ID NO.:3 or SEQ ID NO.:107.

The present invention also relates to an isolated polynucleotide involved in osteoclast differentiation, the isolated polynucleotide may be selected, for example, from the group consisting of;

a) a polynucleotide comprising any one of SEQ ID NO.:1, SEQ ID NO.:3 or SEQ ID NO.:107, b) a polynucleotide comprising the open reading frame of any one of SEQ ID NO.:1, SEQ ID NO.: 3 or SEQ ID NO.:107, c) a polynucleotide which may comprise a transcribed or transcribable portion of any one of SEQ. ID. NO.:1, SEQ ID NO.:3 or SEQ ID NO.:107, which may be, for example, free of untranslated or untranslatable portion(s);

d) a polynucleotide which may comprise a translated or translatable portion of any one of SEQ. ID. NO.: SEQ ID NO.:3 or SEQ ID NO.:107 (e.g., coding portion), e) a polynucleotide substantially identical to a), b), c) or d); and;

f) a sequence of at least 10 nucleic acids which may be substantially complementary to the nucleic acid sequence of any one of SEQ ID NO.:1, SEQ ID NO.:3 or SEQ ID NO.:107 or more particularly of a), b), c) or d).

In accordance with the present invention the isolated polynucleotide may be able to promote osteoclast differentiation (e.g., in a mammal or mammalian cell thereof), i.e, a positive regulator of osteoclast differenciation.

Further in accordance with the present invention, the isolated polynucleotide may be able to inhibit, prevent or lower osteoclast differentiation (e.g., in a mammal or mammalian cell thereof), i.e, a negative regulator of osteoclast differenciation.

In yet a further aspect, the present invention relates to an isolated polynucleotide which may be able to inhibit osteoclast differentiation (e.g., in a mammal or mammalian cell thereof). The polynucleotide may be selected, for example, from the group consisting of polynucleotides which may comprise a sequence of at least 10 nucleic acids which is complementary to the nucleic acid sequence of any one of NSEQ described herein.

Suitable polynucleotides may be those which may be able to inhibit osteoclast differentiation which has been induced by an inducer of osteoclast differentiation such as those listed herein.

In accordance with the present invention, the polynucleotide may be, for example, a RNA molecule, a DNA molecule, including those which are partial or complete, single-stranded or double-stranded, hybrids, etc.

The present invention also relates to a vector (e.g., an expression vector) comprising the polynucleotide of the present invention.

The present invention additionally relates in an aspect thereof to a library of polynucleotide sequences which may be differentially expressed in a differentiated osteoclast cell compared to an undifferentiated osteoclast precursor cell. The library may comprise, for example, at least one member selected from the group consisting of a) a polynucleotide which may comprise any one of SEQ ID NO.:1, SEQ ID NO.: 3 or SEQ ID NO.:107, b) a polynucleotide which may comprise the open reading frame of any one of SEQ ID NO.:1, SEQ ID NO.:3 or SEQ ID NO.:107, c) a polynucleotide which may comprise a transcribed or transcribable portion of any one of SEQ. ID. NO.:1, SEQ ID NO.:3 or SEQ ID NO.:107, which may be, for example, free of untranslated or untranslatable portion(s);

d) a polynucleotide which may comprise a translated or translatable portion of any one of SEQ. ID. NO.:1, SEQ ID NO.:3 or SEQ ID NO.:107 (e.g., coding portion), e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b), c) or d);

f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d) and;

g) a fragment of any one of a) to d).

The present invention also relates to an expression library which may comprise a library of polynucleotides described herein. In accordance with the present invention, each of the polynucleotide may be contained within an expression vector.

Arrays and kits comprising a library of polynucleotide sequences (comprising at least one polynucleotide such as complementary sequences) of the present invention are also encompassed herewith.

The present invention also provides in an additional aspect, a pharmaceutical composition for inhibiting osteoclast differentiation (bone resorption and bone resorption related diseases or disorders), the pharmaceutical composition may comprise, for example;

a) an isolated polynucleotide as defined herein (e.g., able to inhibit osteoclast differentiation) and;

b) a pharmaceutically acceptable carrier.

The present invention also provides in yet an additional aspect, a method for inhibiting osteoclast differentiation (e.g., for inhibiting bone resorption or for ameliorating bone resorption) in a mammal (individual) in need thereof (or in a mammalian cell), the method may comprise administering an isolated polynucleotide (e.g., able to inhibit osteoclast differentiation) or a suitable pharmaceutical composition comprising such suitable polynucleotide.

In accordance with the present invention, the mammal in need may suffer, for example and without limitation, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In a further aspect, the present invention relates to the use of an isolated polynucleotide (e.g., able to inhibit osteoclast differentiation) for the preparation of a medicament for the treatment of a bone resorption disease.

The present invention in another aspect thereof, provides a pharmaceutical composition for promoting osteoclast differentiation in a mammal in need thereof. The pharmaceutical composition may comprise, for example;
  a. an isolated polynucleotide (e.g., able to promote osteoclast differentiation) and;
  b. a pharmaceutically acceptable carrier.

The present invention also further provides a method for promoting osteoclast differentiation in a mammal in need thereof (or in a mammalian cell), the method may comprise, for example, administering an isolated polynucleotide (e.g., able to promote osteoclast differentiation) or a suitable pharmaceutical composition as described above.

The present invention additionally relates to the use of an isolated polynucleotide (e.g., able to promote osteoclast differentiation) for the preparation of a medicament for the treatment of a disease associated with insufficient bone resorption (e.g., hyperostosis) or excessive bone growth.

The present invention also relates to the use of at least one polynucleotide which may be selected from the group consisting of;
  a) a polynucleotide comprising any one of SEQ ID NO.:1, SEQ ID NO.:3 or SEQ ID NO.:107,
  b) a polynucleotide comprising the open reading frame of any one of SEQ ID NO.:1, SEQ ID NO.:3 or SEQ ID NO.:107,
  c) a polynucleotide which may comprise a transcribed or transcribable portion of any one of SEQ. ID. NO.:1, SEQ ID NO.:3 or SEQ ID NO.:107, which may be, for example, free of untranslated or untranslatable portion(s);
  d) a polynucleotide which may comprise a translated or translatable portion of any one of SEQ. ID. NO.:1, SEQ ID NO.:3 or SEQ ID NO.:107 (e.g., coding portion),
  e) a polynucleotide comprising a sequence substantially identical (e.g., from about 50 to 100%, or about 60 to 100% or about 70 to 100% or about 80 to 100% or about 85, 90, 95 to 100% identical over the entire sequence or portion of sequences) to a), b), c) or d);
  f) a polynucleotide comprising a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d);
  g) a fragment of any one of a) to f) and;
  h) a library comprising any one of a) to g)

in the diagnosis of a condition related to bone remodeling (a bone disease).

Also encompassed by the present invention are kits for the diagnosis of a condition related to bone remodeling. The kit may comprise a polynucleotide as described herein.

The present invention also provides in an additional aspect, an isolated polypeptide (polypeptide sequence) involved in osteoclast differentiation (in a mammal or a mammalian cell thereof). The polypeptide may comprise (or consist in) a sequence selected from the group consisting of;
  a) any one of SEQ ID NO.:2 or a SEQ ID NO.:2 variant (e.g., SEQ ID NO.:4, SEQ ID NO.:108),
  b) a polypeptide able to be encoded and/or encoded by any one of SEQ ID NO.:1, SEQ ID NO.:3 or SEQ ID NO.:107 (their coding portion)
  c) a biologically active fragment of any one of a) or b),
  d) a biologically active analog of any one of a) or b).

In accordance with the present invention, the biologically active analog may comprise, for example, at least one amino acid substitution (conservative or non conservative) compared to the original sequence. In accordance with the present invention, the analog may comprise, for example, at least one amino acid substitution, deletion or insertion in its amino acid sequence.

The substitution may be conservative or non-conservative. The polypeptide analog may be a biologically active analog or an immunogenic analog which may comprise, for example, at least one amino acid substitution (conservative or non conservative), for example, 1 to 5, 1 to 10, 1 to 15, 1 to 20, 1 to 50 etc. (including any number there between) compared to the original sequence. An immunogenic analog may comprise, for example, at least one amino acid substitution compared to the original sequence and may still be bound by an antibody specific for the original sequence.

In accordance with the present invention, a polypeptide fragment may comprise, for example, at least 6 consecutive amino acids, at least 8 consecutive amino acids or more of an amino acid sequence described herein.

In yet a further aspect, the present invention provides a pharmaceutical composition which may comprise, for example a polypeptide as described herein and a pharmaceutically acceptable carrier.

Methods for modulating osteoclast differentiation in a mammal in need thereof (or in a mammalian cell) are also provided by the present invention, which methods may comprise administering an isolated polypeptide (e.g., able to promote osteoclast differentiation) or suitable pharmaceutical composition described herein.

In additional aspects, the present invention relates to the use of an isolated polypeptide (e.g., able to promote osteoclast differentiation) for the preparation of a medicament for the treatment of a disease associated with insufficient bone resorption.

Methods for ameliorating bone resorption in an individual in need thereof are also encompassed herewith, which method may comprise, for example, administering an isolated polypeptide (e.g., able to inhibit osteoclast differentiation) or suitable pharmaceutical compositions which may comprise such polypeptide.

In accordance with the present invention, the mammal may suffer, for example, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In yet a further aspect, the present invention relates to the use of a polypeptide able to inhibit osteoclast differentiation in the preparation of a medicament for the treatment of a bone resorption disease in an individual in need thereof.

The present invention also relates to a compound and the use of a compound able to inhibit (e.g., in an osteoclast precursor cell) the activity or expression of a polypeptide which may be selected, for example, from the group consisting of antibodies and antigen binding fragments thereof, in the preparation of a medicament for the treatment of a bone disease in an individual in need thereof.

In yet an additional aspect, the present invention relates to a method of diagnosing a condition related to a bone resorption disorder or disease in an individual in need thereof. The method may comprise, for example, quantifying a polynucleotide described herein, such as, for example, polynucleotide selected from the group consisting of those comprising or consisting of (a) SEQ ID NO.:1, SEQ ID NO.:3 or SEQ ID NO.:107, (b) a polynucleotide which may comprise the open reading frame of SEQ ID NO.:1, SEQ ID NO.:3 or SEQ ID NO.:107, (c) a polynucleotide which may comprise a transcribed or transcribable portion of any one of SEQ. ID. NO.:1, SEQ ID NO.:3 or SEQ ID NO.:107; (d) a polynucleotide which may comprise a translated or translatable portion of any one of SEQ. ID. NO.:1, SEQ ID NO.:3 or SEQ ID NO.:107; (e) substantially identical sequences of any one of (a) to (d); (f) substantially complementary sequences of any one of (a) to (e), or a polypeptide sequence which may be selected, for example, from the group consisting of SEQ ID NO.:2 and a SEQ ID NO.:2 variant thereof in a sample from the individual compared to a standard or normal value.

The present invention also relates to an assay and method for identifying a gene and/or protein involved in bone remodeling. The assay and method may comprise silencing an endogenous gene of an osteoclast cell and providing the cell with a candidate gene (or protein). A candidate gene (or protein) positively involved in bone remodeling may be identified by its ability to complement the silenced endogenous gene. For example, a candidate gene involved in osteoclast differentiation provided to a cell for which an endogenous gene has been silenced, may enable the cell to differentiate in the presence of an inducer such as, for example, RANKL.

The present invention further relates to a cell expressing an exogenous form of any one of the polypeptide (including variants, analogs etc.) or polynucleotide of the present invention (including substantially identical sequences, substantially complementary sequences, fragments, variants, orthologs, etc).

In accordance with the present invention, the cell may be for example, a bone cell. Also in accordance with the present invention, the cell may be an osteoclast (at any level of differentiation).

As used herein the term "exogenous form" is to be understood herein as a form which is not naturally expressed by the cell in question.

Antibodies and Antigen Binding Fragments

The term "antibody" refers to intact antibody, monoclonal or polyclonal antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., SEQ ID NO.:2 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$ are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding. Antibodies and/or antigen binding fragments of the present invention may originate, for example, from a mouse, a rat or any other mammal or from other sources such as through recombinant DNA technologies.

In a further aspect, the present invention relates to an antibody (e.g., isolated antibody), or antigen-binding fragment thereof, that may specifically bind to a protein or polypeptide described herein. The antibody may be, for example, a monoclonal antibody; a polyclonal antibody an antibody generated using recombinant DNA technologies. The antibody may originate for example, from a mouse, rat, rabbit or any other mammal.

The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

Suitable antibodies may also include, for example, an antigen-binding fragment, an Fab fragment; an $F(ab')_2$ fragment, and Fv fragment; or a single-chain antibody comprising an antigen-binding fragment (e.g., a single chain Fv).

The antibody of the present invention may be mutated and selected based on an increased affinity and/or specificity for one of a polypeptide described herein and/or based on a reduced immunogenicity in a desired host.

The antibody may further comprise a detectable label attached thereto.

The present invention further relates to a method of producing antibodies able to bind to one of a polypeptide, polypeptide fragments, or polypeptide analogs described herein, the method may comprise:
   a) immunizing a mammal (e.g., mouse, a transgenic mammal capable of producing human Ig, etc.) with a suitable amount of a PSEQ described herein including, for example, a polypeptide fragment comprising at least 6 consecutive amino acids of a PSEQ;
   b) collecting the serum from the mammal; and
   c) isolating the polypeptide-specific antibodies from the serum of the mammal.

The method may further comprise the step of administering a second dose to the animal.

The present invention also relates to a method of producing a hybridoma which secretes an antibody that binds to a polypeptide described herein, the method may comprise:
   a) immunizing a mammal (e.g., mouse, a transgenic mammal capable of producing human Ig, etc.) with a suitable amount of a PSEQ thereof;
   b) obtaining lymphoid cells from the immunized animal obtained from (a);
   c) fusing the lymphoid cells with an immortalizing cell to produce hybrid cells; and
   d) selecting hybrid cells which produce antibody that specifically binds to a PSEQ thereof.

The present invention further relates to a method of producing an antibody that binds to one of the polypeptide described herein, the method may comprise:
   a) synthesizing a library of antibodies (antigen binding fragment) on phage or ribosomes;
   b) panning the library against a sample by bringing the phage or ribosomes into contact with a composition comprising a polypeptide or polypeptide fragment described herein;
   c) isolating phage which binds to the polypeptide or polypeptide fragment, and;
   d) obtaining an antibody from the phage or ribosomes.

The antibody of the present invention may thus be obtained, for example, from a library (e.g., bacteriophage library) which may be prepared, for example, by
   a) extracting cells which are responsible for production of antibodies from a host mammal;
   b) isolating RNA from the cells of (a);
   c) reverse transcribing mRNA to produce cDNA;
   d) amplifying the cDNA using a (antibody-specific) primer; and
   e) inserting the cDNA of (d) into a phage display vector or ribosome display cassette such that antibodies are expressed on the phage or ribosomes.

The host animal may be immunized with polypeptide and/or a polypeptide fragment and/or analog described herein to induce an immune response prior to extracting the cells which are responsible for production of antibodies.

The present invention also relates to a kit for specifically assaying a polypeptide described herein, the kit may comprise, for example, an antibody or antibody fragment capable of binding specifically to the polypeptide described herein.

The present invention further contemplates antibodies that may bind to PSEQ. Suitable antibodies may bind to unique antigenic regions or epitopes in the polypeptides, or a portion thereof. Epitopes and antigenic regions useful for generating antibodies may be found within the proteins, polypeptides or peptides by procedures available to one of skill in the art. For example, short, unique peptide sequences may be identified in the proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the proteins and polypeptides. These surface epitopes are more readily detected in samples tested for the presence of the proteins and polypeptides. Such antibodies may include, but are not limited to, polyclonal, monoclonal, chimeric, and single chain antibodies, Fab fragments, and fragments produced by a Fab expression library. The production of antibodies is well known to one of skill in the art.

Peptides may be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary widely. The minimum size must be sufficient to provide an antigenic epitope that is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 6, 8, 10, 12 or 15 amino acids, up to about 20 or 25 amino acids.

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

Antigenic polypeptides and peptides are useful for the production of monoclonal and polyclonal antibodies. Antibodies to a polypeptide encoded by the polynucleotides of NSEQ, polypeptide analogs or portions thereof, may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those that inhibit dimer formation, are especially preferred for therapeutic use. Monoclonal antibodies may be prepared using any technique that provides for the production of antibody molecules by continuous cell lines in culture. These include, but are not limited to, the hybridoma, the human B-cell hybridoma, and the EBV-hybridoma techniques. In addition, techniques developed for the production of chimeric antibodies may be used. Alternatively, techniques described for the production of single chain antibodies may be employed. Fabs that may contain specific binding sites for a polypeptide encoded by the polynucleotides of NSEQ, or a portion thereof, may also be generated. Various immunoassays may be used to identify antibodies having the desired specificity. Numerous protocols for competitive binding or immunoradiometric assays using either polyclonal or monoclonal antibodies with established specificities are well known in the art.

Since hybridoma cells are hybrid mouse cells, they are strictly used to produce murine antibodies. It is clear that the glycosyl side chains of such murine antibodies might significantly differ from the glycosylation pattern observed in human cells. Differences in phosphorylation pattern between human cells and hybridomas might also have an impact on the activity of the antibody. Furthermore, administration of murine antibodies to human usually induces an anti-antibody immune response that could potentially neutralize any of the biological activity that the murine antibody might have.

In order to minimize recognition of murine antibodies by the human immune system or for improving the biological activity of the antibodies in human, murine antibodies are advantageously converted into partially (e.g., chimeric) or fully humanized antibodies. Recombinant form of the light chain and heavy chain of the (partially or fully) humanized antibody may thus be introduced into a mammalian expression system other than hybridoma cells (such as 293 cells, CHO or else). Mammalian expression system may procure the advantage of having a resulting glycosylation pattern that is closer to that of naturally occurring human form of the antibodies.

For example, in the case of lytic IgG1 antibodies, the proper glycosylation of the immunoglobulin chains is necessary for effector functions. These biological functions of IgG1 monoclonal antibodies include antibody-dependent cell cytotoxicity (ADCC) and complement-dependent cytotoxicity (CDC), both of which will be greatly influenced by the type of glycosyl side chains that are grafted to the amino acids during expression in mammalian cells.

In addition, optimized mammalian cell expression systems will often secrete significantly a greater amounts of antibodies compared to hybridomas. Therefore, there is a practical and probably economical reason for adopting human cells for production.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (MAbs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of MAbs from mRNA extracted from bone marrow and spleen cells of immunized animals using combinatorial antibody library technology.

One drawback of MAbs derived from animals or from derived cell lines is that although they may be administered to a patient for diagnostic or therapeutic purposes, they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Chimeric antibodies may be constructed in which regions of a non-human MAb are replaced by their human counterparts, e.g., constant region. A preferred chimeric antibody is one that has amino acid sequences that comprise one or more complementarity determining regions (CDRs) of a non-human Mab that binds to a polypeptide encoded by the polynucleotides of NSEQ, or a portion thereof, grafted to human framework (FW) regions. Methods for producing such antibodies are well known in the art. Amino acid residues corresponding to CDRs and FWs are known to one of average skill in the art.

A variety of methods have been developed to preserve or to enhance affinity for antigen of antibodies comprising grafted CDRs. One way is to include in the chimeric antibody the foreign framework residues that influence the conformation of the CDR regions. A second way is to graft the foreign CDRs onto human variable domains with the closest homology to the foreign variable region. Thus, grafting of one or more non-human CDRs onto a human antibody may also involve the substitution of amino acid residues which are adjacent to a particular CDR sequence or which are not contiguous with the CDR sequence but which are packed against the CDR in the overall antibody variable domain structure and which affect the conformation of the CDR. Humanized antibodies of the invention therefore include human antibodies which comprise one or more non-human CDRs as well as such antibodies in which additional substitutions or replacements have been made to preserve or enhance binding characteristics.

Chimeric antibodies of the invention also include antibodies that have been humanized by replacing surface-exposed residues to make the MAb appear human. Because the internal packing of amino acid residues in the vicinity of the antigen-binding site remains unchanged, affinity is preserved. Substitution of surface-exposed residues of a polypeptide encoded by the polynucleotides of NSEQ (or a portion thereof)-antibody according to the invention for the purpose of humanization does not mean substitution of CDR residues or adjacent residues that influence affinity for a polypeptide encoded by the polynucleotides of NSEQ, or a portion thereof.

Chimeric antibodies may also include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Antibodies of the invention include human antibodies (e.g., humanized) that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide encoded by the polynucleotides of NSEQ, or a portion thereof. Preferred variable domain combinations may also be characterized by high specificity for a polypeptide encoded by the polynucleotides of NSEQ, or a portion thereof, and little cross-reactivity to other related antigens. By screening from very large repertoires of antibody fragments, (2-10× $10^{10}$) a good diversity of high affinity Mabs may be isolated, with many expected to have sub-nanomolar affinities for a polypeptide encoded by the polynucleotides of NSEQ, or a portion thereof.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific Mabs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of E. coli. These methods of mutagenesis are illustrative of the many methods known to one of skill in the art.

Antibodies of the invention may include complete antipolypeptide antibodies as well as antibody fragments and derivatives that comprise a binding site for a polypeptide encoded by the polynucleotides of NSEQ, or a portion thereof. Derivatives are macromolecules that comprise a binding site linked to a functional domain. Functional domains may include, but are not limited to signalling domains, toxins, enzymes and cytokines.

The antibodies obtained by the means described herein may be useful for detecting proteins, variant and derivative polypeptides in specific tissues or in body fluids. Moreover, detection of aberrantly expressed proteins or protein fragments is probative of a disease state. For example, expression of the present polypeptides encoded by the polynucleotides of NSEQ, or a portion thereof, may indicate that the protein is being expressed at an inappropriate rate or at an inappropriate developmental stage. Hence, the present antibodies may be useful for detecting diseases associated with protein expression from NSEQs disclosed herein.

A variety of protocols for measuring polypeptides, including ELISAs, RIAs, and FACS, are well known in the art and provide a basis for diagnosing altered or abnormal levels of expression. Standard values for polypeptide expression are established by combining samples taken from healthy subjects, preferably human, with antibody to the polypeptide under conditions for complex formation. The amount of complex formation may be quantified by various methods, such as photometric means. Quantities of polypeptide expressed in disease samples may be compared with standard values. Deviation between standard and subject values may establish the parameters for diagnosing or monitoring disease.

Design of immunoassays is subject to a great deal of variation and a variety of these are known in the art. Immunoassays may use a monoclonal or polyclonal antibody reagent that is directed against one epitope of the antigen being assayed. Alternatively, a combination of monoclonal or polyclonal antibodies may be used which are directed against more than one epitope. Protocols may be based, for example, upon competition where one may use competitive drug screening assays in which neutralizing antibodies capable of binding a polypeptide encoded by the polynucleotides of NSEQ, or a portion thereof, specifically compete with a test compound for binding the polypeptide. Alternatively one may use, direct antigen-antibody reactions or sandwich type assays and protocols may, for example, make use of solid supports or immunoprecipitation. Furthermore, antibodies may be labelled with a reporter molecule for easy detection. Assays that amplify the signal from a bound reagent are also known. Examples include immunoassays that utilize avidin and biotin, or which utilize enzyme-labelled antibody or antigen conjugates, such as ELISA assays.

Kits suitable for immunodiagnosis and containing the appropriate labelled reagents include antibodies directed against the polypeptide protein epitopes or antigenic regions, packaged appropriately with the remaining reagents and materials required for the conduct of the assay, as well as a suitable set of assay instructions.

The present invention therefore provides a kit for specifically assaying a polypeptide described herein, the kit may comprise, for example, an antibody or antibody fragment capable of binding specifically to the polypeptide described herein.

In accordance with the present invention, the kit may be a diagnostic kit, which may comprise:
a) one or more antibodies described herein; and
b) a detection reagent which may comprise a reporter group.

In accordance with the present invention, the antibodies may be immobilized on a solid support. The detection reagent may comprise, for example, an anti-immunoglobulin, protein G, protein A or lectin etc. The reporter group may be selected, without limitation, from the group consisting of radioisotopes, fluorescent groups, luminescent groups, enzymes, biotin and dye particles.

In an additional aspect, the present invention provides a method for identifying an inhibitory compound (inhibitor, antagonist) which may be able to impair the function (activity) or expression of a polypeptide described herein, such as, for example, those which may be selected from the group consisting of SEQ ID NO.:2 or SEQ ID NO.:2 variant. The method may comprise contacting the polypeptide or a cell expressing the polypeptide with a candidate compound and measuring the function (activity) or expression of the polypeptide. A reduction in the function or activity of the polypeptide (compared to the absence of the candidate compound) may positively identify a suitable inhibitory compound.

In accordance with the present invention, the impaired function or activity may be associated with a reduced ability of the polypeptide to promote osteoclast differentiation, such as osteoclast differentiation induced by an inducer described herein or known in the art.

In accordance with the present invention the cell may not naturally (endogenously) express (polypeptide may substantially be unexpressed in a cell) the polypeptide or analog or alternatively, the expression of a naturally expressed polypeptide analog may be repressed.

For example, suitable method of screening for an inhibitor of SEQ ID NO.:1 may comprise repressing the expression of the mouse ortholog in a mouse osteoclast cell and evaluating differentiation of the osteoclast cell comprising SEQ ID NO.:1 in the presence or absence of a candidate inhibitor and for example, an inducer of osteoclast differentiation (e.g., RANKL).

The present invention also provides a method for identifying an inhibitory compound (inhibitor, antagonist) able to impair the function (activity) or expression of a polypeptide such as, for example SEQ ID NO.:2 or a SEQ ID NO.:2 variant such as SEQ ID NO.:4 or SEQ ID NO.:108. The method may comprise, for example, contacting the (isolated) polypeptide or a cell expressing the polypeptide with a candidate compound and measuring the function (activity) or expression of the polypeptide. A reduction in the function or activity of the polypeptide (compared to the absence of the candidate compound) may thus positively identify a suitable inhibitory compound.

In accordance with the present invention, the impaired function or activity may be associated, for example, with a reduced ability of the polypeptide to inhibit or promote osteoclast differentiation.

The cell used to carry the screening test may not naturally (endogenously) express the polypeptide or analogs, or alternatively the expression of a naturally expressed polypeptide analog may be repressed.

The present invention also relates to a method of identifying a positive or a negative regulator of osteoclast differentiation. The method may comprise, for example, performing a knockdown effect as described herein. The method may more particularly comprise a) providing an osteoclast cell with a compound (e.g., siRNA) able to specifically inhibit a target sequence (e.g., a polynucleotide or polypeptide as described herein), b) inducing differentiation (e.g., with an inducer such as, for example, RANKL) and c) determining the level of differentiation of the osteoclast cell (e.g., measuring the number of differentiated cells, their rate of differentiation, specific marker of differentiation etc).

Upon inhibition of a positive regulator, the levels of osteoclast differentiation will appear lowered. Upon inhibition of a negative regulator, the level of osteoclast differentiation will appear increased.

Another method of identifying a positive or a negative regulator of osteoclast differentiation is to a) provide a cell with one of a target sequence described herein (polypeptide or polynucleotide able to express a polypeptide) b) to induce differentiation (e.g., with an inducer such as, for example, RANKL) and c) to determine the level of differentiation of the osteoclast cell (e.g., measuring the number of differentiated cells, their rate of differentiation, specific marker of differentiation etc).

A cell provided with a positive regulator of osteoclast differentiation may have an increased level of differentiation. A cell provided with a negative regulator of osteoclast differentiation may have a decreased level of differentiation.

The present invention also provides a method of identifying a compound capable of interfering with osteoclast differentiation, the method may comprise contacting a cell including therein a non-endogenous polynucleotide sequence comprising any one of SEQ ID NO.:1, SEQ ID NO.:3 or SEQ ID NO.:107 (a coding portion) and quantifying (e.g. the number of) differentiated osteoclasts. A reduction in osteoclast differentiation in the presence of the compound in comparison to the absence of the compound may be indicative of an antagonist of osteoclast differentiation, while an increase in osteoclast differentiation in the presence of the compound in comparison to the absence of the compound may be indicative of an agonist of osteoclast differentiation.

In accordance with the present invention, the cell may also comprise an endogenous form of a polynucleotide.

As used herein the term "endogenous" means a substance that naturally originates from within an organism, tissue or cell. The term "endogenous polynucleotide" refers to a chromosomal form of a polynucleotide or RNA version (hnRNA, mRNA) produced by the chromosal form of the polynucleotide. The term "endogenous polypeptide" refers to the form of the protein encoded by an "endogenous polynucleotide".

As used herein the term "non-endogenous" or "exogenous" is used in opposition to "endogenous" in that the substance is provided from an external source although it may be introduced within the cell. The term "non-endogenous polynucleotide" refers to a synthetic polynucleotide introduced within the cell and include for example and without limitation, a vector comprising a sequence of interest, a synthetic mRNA, an oligonucleotide comprising a NSEQ etc. The term "non-endogenous polypeptide" refers to the form of the protein encoded by a "non-endogenous polynucleotide".

The present invention also relates to a method of identifying a compound capable of interfering with osteoclast differentiation, the method may comprise contacting a cell including therein a non-endogenous polypeptide sequence comprising any one of SEQ ID NO.:2 or SEQ ID NO.:2 variant with the compound and quantifying (e.g. the number of) differentiated osteoclasts. A reduction in osteoclast differentiation in the presence of the compound in comparison to the absence of the compound may be indicative of an antagonist of osteoclast differentiation while an increase in osteoclast differentiation in the presence of the compound in comparison to the absence of the compound may be indicative of an agonist of osteoclast differentiation.

As used herein the term "sequence identity" relates to (consecutive) nucleotides of a nucleotide sequence which with reference to an original nucleotide sequence. The identity may be compared over a region or over the total sequence of a nucleic acid sequence.

Thus, "identity" may be compared, for example, over a region of 3, 4, 5, 10, 19, 20 nucleotides or more (and any number there between). It is to be understood herein that gaps of non-identical nucleotides may be found between identical nucleic acids. For example, a polynucleotide may have 100% identity with another polynucleotide over a portion thereof. However, when the entire sequence of both polynucleotides is compared, the two polynucleotides may have 50% of their overall (total) sequence identical to one another.

Polynucleotides of the present invention or portion thereof having from about 50 to about 100%, or about 60 to about 100% or about 70 to about 100% or about 80 to about 100% or about 85%, about 90%, about 95% to about 100% sequence identity with an original polynucleotide are encompassed herewith. It is known by those of skill in the art, that a polynucleotide having from about 50% to 100% identity may function (e.g., anneal to a substantially complementary sequence) in a manner similar to an original polynucleotide and therefore may be used in replacement of an original polynucleotide. For example a polynucleotide (a nucleic acid sequence) may comprise or have from about 50% to 100% identity with an original polynucleotide over a defined region and may still work as efficiently or sufficiently to achieve the present invention.

Percent identity may be determined, for example, with an algorithm GAP, BESTFIT, or FASTA in the Wisconsin Genetics Software Package Release 7.0, using default gap weights.

As used herein the terms "sequence complementarity" refers to (consecutive) nucleotides of a nucleotide sequence which are complementary to a reference (original) nucleotide sequence. The complementarity may be compared over a region or over the total sequence of a nucleic acid sequence.

Polynucleotides of the present invention or portion thereof having from about 50 to about 100%, or about 60 to about 100% or about 70 to about 100% or about 80 to about 100% or about 85%, about 90%, about 95% to about 100% sequence complementarity with an original polynucleotide are thus encompassed herewith. It is known by those of skill in the art, that an polynucleotide having from about 50% to 100% complementarity with an original sequence may anneal to that sequence in a manner sufficient to carry out the present invention (e.g., inhibit expression of the original polynucleotide).

An "analogue" is to be understood herein as a molecule having a biological activity and chemical structure similar to that of a polypeptide described herein. An "analogue" may have sequence similarity with that of an original sequence or a portion of an original sequence and may also have a modification of its structure as discussed herein. For example, an "analogue" may have at least 90% sequence similarity with an original sequence or a portion of an original sequence. An "analogue" may also have, for example; at least 70% or even 50% sequence similarity (or less, i.e., at least 40%) with an original sequence or a portion of an original sequence.

Also, an "analogue" with reference to a polypeptide may have, for example, at least 50% sequence similarity to an original sequence with a combination of one or more modification in a backbone or side-chain of an amino acid, or an addition of a group or another molecule, etc.

"Polynucleotide" generally refers to any polyribonucleotide or polydeoxyribo-nucleotide, which may be unmodified RNA or DNA, or modified RNA or DNA.

"Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "polypeptide analog" relates to mutants, variants, chimeras, fusions, deletions, additions and any other type of modifications made relative to a given polypeptide.

As used herein the term "biologically active" refers to a variant or fragment which retains some or all of the biological activity of the natural polypeptide, i.e., to be able to promote or inhibit osteoclast differentiation. Polypeptides or fragments of the present invention may also include "immunologically active" polypeptides or fragments. "Immunologically active polypeptides or fragments may be useful for immunization purposes (e.g. in the generation of antibodies).

Thus, biologically active polypeptides in the form of the original polypeptides, fragments (modified or not), analogues (modified or not), derivatives (modified or not), homologues, (modified or not) of the polypeptides described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be desirable. Polypeptides of the present invention may comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and H is may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table A. If such substitutions result in a change not desired, then other type of substitutions, denominated "exemplary substitutions" in Table A, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE A

Examplary amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc.; and similarly with respect to other parameters such as, concentrations, elements, etc.

It is in particular to be understood herein that the methods of the present invention each include each and every individual steps described thereby as well as those defined as positively including particular steps or excluding particular steps or a combination thereof; for example an exclusionary definition for a method of the present invention, may read as follows: "provided that said polynucleotide does not comprise or consist in SEQ ID NO.:XX or the open reading frame of SEQ ID NO.:XX" or "provided that said polypeptide does not comprise or consist in SEQ ID NO.:XX" or "provided that said polynucleotide fragment or said polypeptide fragment is less than X unit (e.g., nucleotides or amino acids) long or more than X unit (e.g., nucleotides or amino acids) long".

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

In the appended drawings:

In FIG. 1, macroarrays were prepared using RAMP amplified RNA from human precursor cells (A-F1), and differentiated intermediate (A-F 2-3) and mature osteoclasts for four human donors (A-F 4), and 30 different normal human tissues (adrenal (A5), liver (B5), lung (C5), ovary (D5), skeletal muscle (E5), heart (F5), cervix (G5), thyroid (H5), breast (A6), placenta (B6), adrenal cortex (C6), kidney (D6), vena cava (E6), fallopian tube (F6), pancreas (G6), testicle (H6), jejunum (A7), aorta (B7), esophagus (C7), prostate (D7), stomach (E7), spleen (F7), ileum (G7), trachea (A8), brain (B8), colon (C8), thymus (D8), small intestine (E8), bladder (F8) and duodenum (G8)). The STAR dsDNA clone representing the respective SEQ ID NOs. was labeled with $^{32}$P and hybridized to the macroarray. The probe labeling reaction was also spiked with a dsDNA sequence for *Arabidopsis*, which hybridizes to the same sequence spotted on the macroarray (M) in order to serve as a control for the labeling reaction. Quantitation of the hybridization signal at each spot was performed using a STORM 820 phosphorimager and the ImageQuant TL software (Amersham Biosciences, Piscataway, N.J.). A $\log_2$ value representing the average of the signals for the precursors (A-F1) was used as the baseline and was subtracted from the $\log_2$ value obtained for each of the remaining samples in order to determine their relative abundancies compared to the precursors and plotted as a bar graph (right panel).

FIG. 6 shows the results of an Fc-Siglec-15 ELISA of the individual monoclonal antibodies selected from the 96-well plate from Omniclonal library #25 containing anti-Siglec-15 Fabs. The wells indicated by bold numbers contained the exemplary monoclonals 25A1, 25B4, 25B8, 25C1, 25D8, 25E5, 25E6, and 25E9. Also shown is an ELISA on the same plate using the Fc moiety alone to identify those monoclonals that were specific for the Fc portion of the Fc-Siglec-15 fusion protein.

DESCRIPTION OF ILLUSTRATIVE EMBODIMENTS

Figure 1:
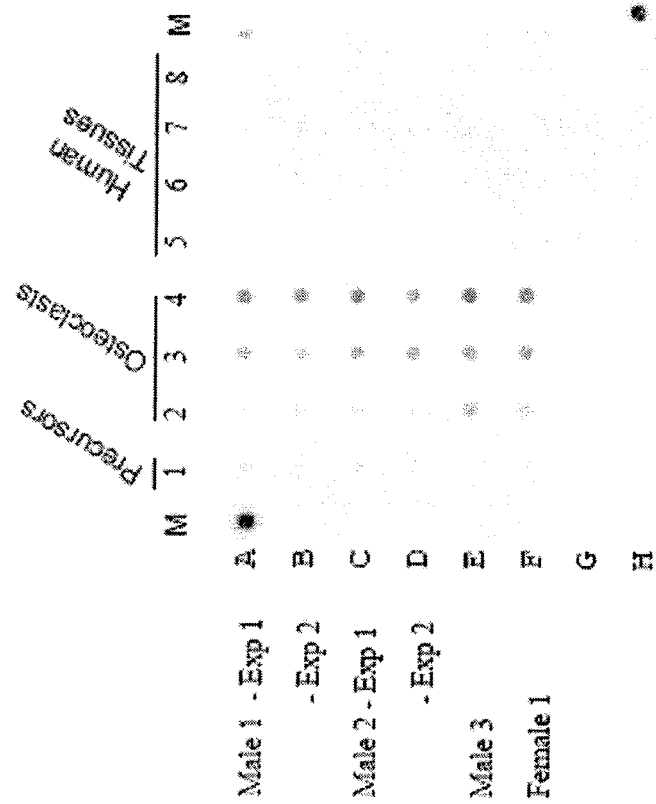
FIG. 1 is a picture of the macroarray hybridization results and quantitation of the signal intensities showing the differential expression data for STAR selected osteoclast-specific human SEQ. ID. NO.:1. The hybridization results obtained confirms its upregulation in all of the human osteoclast samples with generally higher expression in the more mature osteoclasts (A-F 2-4) compared to the precursors (A-F1) and little or no expression in most normal tissues (A-H 5-6 and A-G 7-8).
Figure 1:
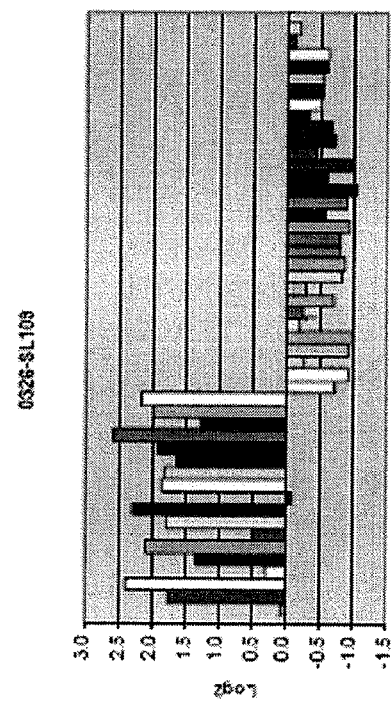

The applicant employed a carefully planned strategy to identify and isolate genetic sequences involved in osteoclastogenesis and bone remodeling. The process involved the following steps: 1) preparation of highly representative cDNA libraries using mRNA isolated from precursors and differentiated intermediate and mature osteoclasts of human origin; 2) isolation of sequences upregulated during osteoclastogenesis; 3) identification and characterization of upregulated sequences; 4) selection of upregulated sequences for tissue specificity; and 5) determination of knock-down effects on osteoclastogenesis. The results discussed in this disclosure demonstrate the advantage of targeting osteoclast genes that are specific to this differentiated cell type and provide a more efficient screening method when studying the genetic basis of diseases and disorders. Genes that are known to have a role in other areas of biology have been shown to play a critical role in osteoclastogenesis and osteoclast function. Genes that are known but have not had a role assigned to them until the present disclosure have also been isolated and shown to have a critical role in osteoclastogenesis and osteoclast function. Finally, novel genes have been identified and play a role, however, applicant reserves their disclosure until further study has been completed.

The present invention is illustrated in further details below in a non-limiting fashion.

Material and Methods

Commercially available reagents referred to in the present disclosure were used according to supplier's instructions unless otherwise indicated. Throughout the present disclosure certain starting materials were prepared as follows:

Example 1

Preparation of Osteoclast Differentiated Cells

The RAW 264.7 (RAW) osteoclast precursor cell line and human precursor cells (peripheral blood mononuclear cells or CD34+ progenitors) are well known in the art as murine and human models of osteoclastogenesis. These murine and human osteoclasts are therefore excellent sources of materials for isolating and characterizing genes specialized for osteoclast function.

Human primary osteoclasts were differentiated from G-CSF-mobilized peripheral blood mononuclear cells (Cambrex, East Rutherford, N.J.) as described by the supplier in the presence of 35 ng/ml M-CSF and 100 ng/ml RANK ligand. Multinucleated TRAP-staining osteoclasts were visible by 11-14 days. Osteoclasts were also derived from human osteoclasts precursor cells (CD34+ progenitors) (Cambrex, East Rutherford, N.J.) and cultured as described by the supplier. In the latter case, osteoclasts were obtained after 7 days.

RAW cells were purchased from American Type Culture Collection and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of $4 \times 10^3$ cells/well and allowed to plate for 24 h. Differentiation was induced in high glucose DMEM, 10% charcoal-treated foetal bovine serum (Hyclone, Logan, Utah), 0.05% BSA, antibiotics, 10 ng/ml macrophage colony stimulating factor (M-CSF), and 100 ng/ml receptor activator of NF-kB (RANK) ligand. The plates were re-fed on day 3 and osteoclasts were clearly visible by day 4. Typically, the cells were stained for tartrate-resistant acid phosphatase (TRAP) on day 4 or 5 unless otherwise indicated. For TRAP staining, the cells were washed with PBS and fixed in 10% formaldehyde for 1 h. After two PBS washes, the cells were rendered lightly permeable in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. Cells were visualized microscopically.

Example 2

Method of Isolating Differentially Expressed mRNA

Key to the discovery of differentially expressed sequences unique to osteoclasts is the use of the applicant's patented STAR technology (Subtractive Transcription-based Amplification of mRNA; U.S. Pat. No. 5,712,127 Malek et al., issued on Jan. 27, 1998). In this procedure, mRNA isolated from intermediate and mature osteoclasts is used to prepare "tester RNA", which is hybridized to complementary single-stranded "driver DNA" prepared from osteoclast precursor mRNA and only the un-hybridized "tester RNA" is recovered, and used to create cloned cDNA libraries, termed "subtracted libraries". Thus, the "subtracted libraries" are enriched for differentially expressed sequences inclusive of rare and novel mRNAs often missed by micro-array hybridization analysis. These rare and novel mRNA are thought to be representative of important gene targets for the development of better diagnostic and therapeutic strategies.

The clones contained in the enriched "subtracted libraries" are identified by DNA sequence analysis and their potential function assessed by acquiring information available in public databases (NCBI and GeneCard). The non-redundant clones are then used to prepare DNA micro-arrays, which are used to quantify their relative differential expression patterns by hybridization to fluorescent cDNA probes. Two classes of cDNA probes may be used, those which are generated from either RNA transcripts prepared from the same subtracted libraries (subtracted probes) or from mRNA isolated from different osteoclast samples (standard probes). The use of subtracted probes provides increased sensitivity for detecting the low abundance mRNA sequences that are preserved and enriched by STAR. Furthermore, the specificity of the differentially expressed sequences to osteoclast is measured by hybridizing radio-labeled probes prepared from each selected sequence to macroarrays containing RNA from different osteoclast samples and different normal human tissues. Additionally, Northern blot analysis is performed so as to confirm the presence of one or more specific mRNA species in the osteoclast samples. Following this, the full-length cDNAs representative of the mRNA species and/or spliced variants are cloned in E. coli DH10B.

A major challenge in gene expression profiling is the limited quantities of RNA available for molecular analysis. The amount of RNA isolated from many osteoclast samples or human specimens (needle aspiration, laser capture microdissection (LCM) samples and transfected cultured cells) is often insufficient for preparing: 1) conventional tester and driver materials for STAR; 2) standard cDNA probes for DNA micro-array analysis; 3) RNA macroarrays for testing the specificity of expression; 4) Northern blots and; 5) full-length cDNA clones for further biological validation and characterization etc. Thus, the applicant has developed a proprietary technology called RAMP (RNA Amplification Procedure) (U.S. patent application Ser. No. 11/000,958 published under No. US 2005/0153333A1 on Jul. 14, 2005 and entitled "Selective Terminal Tagging of Nucleic Acids"), which linearly amplifies the mRNA contained in total RNA samples yielding microgram quantities of amplified RNA sufficient for the various analytical applications. The RAMP RNA produced is largely full-length mRNA-like sequences as a result of the proprietary method for adding a terminal sequence tag to the 3'-ends of single-stranded cDNA molecules, for use in linear transcription amplification. Greater than 99.5% of the sequences amplified in RAMP reactions show <2-fold variability and thus, RAMP provides unbiased RNA samples in quantities sufficient to enable the discovery of the unique mRNA sequences involved in osteoclastogenesis.

Example 3

Preparation of Human Osteoclasts Subtracted Library

Two human primary precursor cells from two different donors (Cambrex, East Rutherford, N.J.), and the corresponding intermediate (day 3 and day 7) and mature (days 11-14) osteoclasts were prepared as described above. Isolation of cellular RNA followed by mRNA purification from each was performed using standard methods (Qiagen, Mississauga, ON). Following the teachings of Malek et al. (U.S. Pat. No. 5,712,127), 2 µg of poly A+ mRNA from each sample were used to prepare highly representative (>2×10$^6$ CFU) cDNA libraries in specialized plasmid vectors necessary for preparing tester and driver materials. In each case, first-strand cDNA was synthesized using an oligo dT$_{11}$ primer with 3' locking nucleotides (e.g., A, G or C) and containing a Not I recognition site. Next, second-strand cDNA synthesis was performed according to the manufacturer's procedure for double-stranded cDNA synthesis (Invitrogen, Burlington, ON) and the resulting double-stranded cDNA ligated to linkers containing an Asc I recognition site (New England Biolabs, Pickering, ON). The double-stranded cDNAs were then digested with Asc I and Not I restriction enzymes (New England Biolabs, Pickering, ON), purified from the excess linkers using the cDNA fractionation column from Invitrogen (Burlington, ON) as specified by the manufacturer and each ligated into specialized plasmid vectors—p14 (SEQ. ID. NO.:6) and p17+ (SEQ. ID. NO.:7) used for preparing tester and driver materials respectively. Thereafter, the ligated cDNAs were transformed into E. coli DH10B resulting in the desired cDNA libraries (RAW 264.7-precursor-p14, RAW 264.7-precursor-p17+, RAW 264.7-osteoclasts-p14 and RAW 264.7-osteoclasts-p17+). The plasmid DNA pool for each cDNA library was purified and a 2-µg aliquot of each linearized with Not I restriction enzyme. In vitro transcription of the Not I digested p14 and p17+ plasmid libraries was then performed with T7 RNA polymerase and sp6 RNA polymerase respectively (Ambion, Austin, Tex.).

Next, in order to prepare 3'-represented tester and driver libraries, a 10-µg aliquot of each of the in vitro synthesized RNA was converted to double-stranded cDNA by performing first-strand cDNA synthesis as described above followed by primer-directed (primer OGS 77 for p14 (SEQ. ID. NO.:8) and primer OGS 302 for p17+ (SEQ. ID. NO.:9)) second-strand DNA synthesis using Advantage-2 Taq polymerase (BD Biosciences Clontech, Mississauga, ON). The sequences corresponding to OGS 77 and OGS 302 were introduced into the in vitro synthesized RNA by way of the specialized vectors used for preparing the cDNA libraries. Thereafter, 6×1-µg aliquots of each double-stranded cDNA was digested individually with one of the following 4-base recognition restriction enzymes Rsa I, Sau3A1, Mse I, Msp I, MinPI I and Bsh 12361 (MBI Fermentas, Burlington, ON), yielding up to six possible 3'-fragments for each RNA species contained in the cDNA library. Following digestion, the restriction enzymes were inactivated with phenol and the set of six reactions pooled. The restriction enzymes sites were then blunted with T4 DNA polymerase and ligated to linkers containing an Asc I recognition site. Each linker-adapted pooled DNA sample was digested with Asc I and Not I restriction enzymes, desalted and ligated to specialized plasmid vectors, p14 and p17 (p17 plasmid vector is similar to the p17+ plasmid vector except for the sequence corresponding to SEQ. ID. NO.:9), and transformed into E. coli DH10B. The plasmid DNA pool for each p14 and p17 3'-represented library was purified (Qiagen, Mississauga, ON) and a 2-µg aliquot of each digested with Not I restriction enzyme, and transcribed in vitro with either T7 RNA polymerase or sp6 RNA polymerase (Ambion, Austin, Tex.). The resulting p14 3'-represented RNA was used directly as "tester RNA" whereas, the p17 3'-represented RNA was used to synthesize first-strand cDNA as described above, which then served as "driver DNA". Each "driver DNA" reaction was treated with RNase A and RNase H to remove the RNA, phenol extracted and desalted before use.

The following 3'-represented libraries were prepared:
Tester 1 (donor 1-day 3)—human intermediate osteoclast-3' in p14
Tester 2 (donor 1-day 7—human intermediate osteoclast)-3' in p14
Tester 3 (donor 1-day 11—human mature osteoclast)-3' in p14
Tester 4 (donor 2-day 3—human intermediate osteoclast)-3' in p14
Tester 5 (donor 2-day 7—human intermediate osteoclast)-3' in p14
Tester 6 (donor 2-day 13—human mature osteoclast)-3' in p14
Driver 1 (donor 1-day 3)—human precursor-3' in p17
Driver 2 (donor 2-day 3)—human precursor-3' in p17

The tester RNA samples were subtracted following the teachings of U.S. Pat. No. 5,712,127 with the corresponding driver DNA in a ratio of 1:100 for either 1- or 2-rounds following the teachings of Malek et al. (U.S. Pat. No. 5,712,127). Additionally, control reactions containing tester RNA and no driver DNA, and tester RNA plus driver DNA but no RNase H was prepared. The tester RNA remaining in each reaction after subtraction was converted to double-stranded DNA and a volume of 5% removed and amplified in a standard PCR reaction for 30-cycles for analytical purposes. The remaining 95% of only the driver plus RNase H subtracted samples were amplified for 4-cycles in PCR, digested with Asc I and Not I restriction enzymes, and one half ligated into the pCATRMAN (SEQ. ID. NO.:10) plasmid vector and the other half, into the p20 (SEQ. ID. NO.:11) plasmid vector. The ligated materials were transformed into E. coli DH10B and individual clones contained in the pCATRMAN libraries were picked for further analysis (DNA sequencing and hybridization) whereas, clones contained in each p20 library were pooled for use as subtracted probes. Each 4-cycles amplified cloned subtracted library contained between 25,000 and 40,000 colonies.

The following cloned subtracted libraries were prepared:
SL90-tester 1 (day 3 osteoclast) minus driver 1 (precursor) (1-round) in pCATRMAN;
SL91-tester 2 (day 7 osteoclast) minus driver 1 (precursor) (1-round) in pCATRMAN;
SL92-tester 3 (day 11 osteoclast) minus driver 1 (precursor) (1-round) in pCATRMAN;
SL108-tester 1 (day 3 osteoclast) minus driver 1 (precursor) (2-rounds) in pCATRMAN;
SL109-tester 2 (day 7 osteoclast) minus driver 1 (precursor) (2-rounds) in pCATRMAN;
SL110-tester 3 (day 11 osteoclast) minus driver 1 (precursor) (2-rounds) in pCATRMAN;
SL93-tester 4 (day 3 osteoclast) minus driver 2 (precursor) (1-round) in pCATRMAN;
SL94-tester 5 (day 7 osteoclast) minus driver 2 (precursor) (1-round) in pCATRMAN;
SL95-tester 6 (day 13 osteoclast) minus driver 2 (precursor) (1-round) in pCATRMAN;
SL87-tester 4 (day 3 osteoclast) minus driver 2 (precursor) (2-rounds) in pCATRMAN;
SL88-tester 5 (day 7 osteoclast) minus driver 2 (precursor) (2-rounds) in pCATRMAN;
SL89-tester 6 (day 11 osteoclast) minus driver 2 (precursor) (2-rounds) in pCATRMAN A 5-4 aliquot of the 30-cycles PCR amplified subtracted materials described above were visualized on a 1.5% agarose gel containing ethidium bromide and then transferred to Hybond N+ (Amersham Biosciences, Piscataway, N.J.) nylon membrane for Southern blot analysis. Using radiolabeled probes specific to the CTSK (cathepsin K; NM_000396.2) gene, which is known to be upregulated in osteoclasts, and GAPDH (glyceraldehyde-3-phosphate dehydrogenase; M32599.1), which is a non-differentially expressed house-keeping gene, it was evident that there was subtraction of GAPDH but not CTSK. Based on these results, it was anticipated that the subtracted libraries would be enriched for differentially expressed upregulated sequences.

Example 4

Sequence Identification and Annotation of Clones Contained in the Subtracted Libraries A total of 6,912 individual colonies contained in the pCATRMAN subtracted libraries (SL87-95 and SL108-110) described above were randomly picked using a Qbot (Genetix Inc., Boston, Mass.) into 60 µL of autoclaved water. Then, 42 µL of each was used in a 100-µL standard PCR reaction containing oligonucleotide primers, OGS 1 and OGS 142 and amplified for 40-cycles (94° C. for 10 minutes, 40× (94° C. for 40 seconds, 55° C. for 30 seconds and 72° C. for 2 minutes) followed by 72° C. for 7 minutes) in 96-wells microtitre plates using HotStart™ Taq polymerase (Qiagen, Mississauga, ON). The completed PCR reactions were desalted using the 96-well filter plates (Corning) and the amplicons recovered in 100 µL 10 mM Tris (pH 8.0). A 5-4 aliquot of each PCR reaction was visualized on a 1.5% agarose gel containing ethidium bromide and only those reactions containing a single amplified product were selected for DNA sequence analysis using standard DNA sequencing performed on an ABI 3100 instrument (Applied Biosystems, Foster City, Calif.). Each DNA sequence obtained was given a Sequence Identification Number and entered into a database for subsequent tracking and annotation.

Each sequence was selected for BLAST analysis of public databases (e.g. NCBI). Absent from these sequences were the standard housekeeping genes (GAPDH, actin, most ribosomal proteins etc.), which was a good indication that the subtracted library was depleted of at least the relatively abundant non-differentially expressed sequences.

Once sequencing and annotation of the selected clones were completed, the next step involved identifying those sequences that were actually upregulated in osteoclasts compared to precursors.

Example 5

Hybridization Analysis for Identifying Upregulated Sequences

The PCR amplicons representing the annotated sequences from the pCATRMAN libraries described above were used to prepare DNA microarrays. The purified PCR amplicons contained in 70 µL of the PCR reactions prepared in the previous section was lyophilized and each reconstituted in 20 µL of spotting solution comprising 3×SSC and 0.1% sarkosyl. DNA micro-arrays of each amplicon in triplicate were then prepared using CMT-GAP2 slides (Corning, Corning, N.Y.) and the GMS 417 spotter (Affymetrix, Santa Clara, Calif.).

The DNA micro-arrays were then hybridized with either standard or subtracted cy3 and cy5 labelled cDNA probes as recommended by the supplier (Amersham Biosciences, Piscataway, N.J.). The standard cDNA probes were synthesized using RAMP amplified RNA prepared from the different human osteoclast samples and the corresponding precursors. It is well known to the skilled artisan that standard cDNA probes only provide limited sensitivity of detection and consequently, low abundance sequences contained in the cDNA probes are usually missed. Thus, the hybridization analysis was also performed using cy3 and cy5 labelled subtracted cDNA probes prepared from subtracted libraries representing the different tester and driver materials. These subtracted libraries may be enriched for low abundance sequences as a result of following the teachings of Malek et al., and therefore, may provide increased detection sensitivity.

All hybridization reactions were performed using the dye-swap procedure as recommended by the supplier (Amersham Biosciences, Piscataway, N.J.) and approximately 500 putatively differentially expressed upregulated (>2-fold) sequences were selected for further analysis.

Example 6

Determining Osteoclast Specificity of the Differentially Expressed Sequences Identified The differentially expressed sequences identified in Section F for the different human osteoclast subtracted libraries were tested for osteoclast specificity by hybridization to nylon membrane-based macroarrays. The macroarrays were prepared using RAMP amplified RNA from human precursors and osteoclasts (intermediate and mature) of six independent experiments from 4 different donors (3 males and 1 female), and 30 normal human tissues (adrenal, liver, lung, ovary, skeletal muscle, heart, cervix, thyroid, breast, placenta, adrenal cortex, kidney, vena cava, fallopian tube, pancreas, testicle, jejunum, aorta, esophagus, prostate, stomach, spleen, ileum, trachea, brain, colon, thymus, small intestine, bladder and duodenum) purchased commercially (Ambion, Austin, Tex.). Because of the limited quantities of mRNA available for many of these samples, it was necessary to first amplify the mRNA using the RAMP methodology. Each amplified RNA sample was reconstituted to a final concentration of 250 ng/μL in 3×SSC and 0.1% sarkosyl in a 96-well microtitre plate and 1 μL spotted onto Hybond N+ nylon membranes using the specialized MULTI-PRINT™ apparatus (VP Scientific, San Diego, Calif.), air dried and UV-cross linked. A total of 400 different sequences selected from SL87-95 and SL108-110 were individually radiolabeled with α-$^{32}$P-dCTP using the random priming procedure recommended by the supplier (Amersham, Piscataway, N.J.) and used as probes on the macroarrays. Hybridization and washing steps were performed following standard procedures well known to those skilled in the art.

Of the 500 sequences tested, approximately 85% were found to be upregulated in all of the osteoclast RNA samples that were used to prepare the macroarrays. However, many of these sequences were also readily detected in a majority of the different normal human tissues. Based on these results, those sequences that appeared to be associated with experimental variability and those that were detected in many of the other human tissues at significantly elevated levels were eliminated. Consequently, only 35 sequences, which appeared to be upregulated and highly osteoclast-specific, were selected for biological validation studies. Included in this set of 35 genes were 4 where there was a significant upregulation in mature osteoclasts compared to most normal tissues but because the expression of these genes were overall lower in the precursor cells, they appeared to be elevated in the normal tissues after quantitation. However, their expression in the normal tissues was still relatively lower than that of the mature osteoclasts. Thus, these genes may still be important regulators in osteoclastogenesis and bone resorption and were therefore selected for biological validation. This subset of 35 sequences does not include genes also identified such as, CTSK, TRAP, MMP9, CST3 and CKB amongst others since these were previously reported in the literature to be upregulated in osteoclasts. FIG. 1 shows the macroarray pattern and quantitation of the hybridization signals of the osteoclasts and normal human tissues relative to precursor cells for the sequence selected for biological validation. Amongst the 35 sequences studied were 24 genes with functional annotation 9 genes with no functional annotation and 2 novel sequences (genomic hits). The identification of gene products involved in regulating osteoclast differentiation and function has thus led to the discovery of novel targets for the development of new and specific therapies of disease states characterized by abnormal bone remodeling.

SEQ. ID. NO.:1:

SEQ. ID. NO.:1 corresponds to a previously identified gene that encodes a hypothetical protein, LOC284266 with an unknown function. We have demonstrated that this gene is markedly upregulated in intermediate and mature osteoclast compared to precursor cells and other normal human tissues (FIG. 1), which have not been previously reported. Thus, it is believed that this gene may be required for osteoclastogenesis and/or bone remodeling.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO.: 1 | Hs.287692/ CD33L3/ | NM_213602 | 150-1136 encoding SEQ | hypothetical protein |
| | 284266/ SIGLEC-15 | | ID NO.: 2 | LOC284266; membrane associated function unknown |

Example 7

Cloning of Full-Length cDNAs of Selected Sequences from Osteoclast mRNA

It was necessary to obtain full-length cDNA sequences in order to perform functional studies of the expressed proteins. Spliced variants are increasingly being implicated in tissue specific functions and as such, it is important to work with cDNA clones from the system under study. Applicant also recognizes that spliced variants may not always be involved. Thus, the applicant's approach has been to isolate the relevant full-length cDNA sequences directly from osteoclasts in order to identify variants and their potential role with respect to specificity.

Coding cDNA clones were isolated using both a 5'-RACE strategy (Invitrogen, Burlington, ON) and a standard two-primer gene specific approach in PCR. The 5'-RACE strategy used cDNA prepared from cap-selected osteoclast RNA and/or RAMP amplified osteoclast RNA. For amplification using gene specific primers, either cDNA prepared from RAMP RNA or total RNA was used. All cDNAs were synthesized following standard reverse transcription procedures (Invitrogen, Burlington, ON). The cDNA sequences obtained were cloned in E. coli DH10B and the nucleotide sequences for multiple clones determined. Thereafter, the cDNA sequences for each set were aligned and the open reading frame(s) (ORF) identified using standard software (e.g. ORF Finder-NCBI). The cDNA clones for the coding region for SEQ. ID. NO.:1 obtained from a human osteoclast sample, were identical to that of the published sequences corresponding to Accession#NM_213602.

Example 8

RNA Interference Studies

RNA interference is a recently discovered gene regulation mechanism that involves the sequence-specific decrease in a gene's expression by targeting the mRNA for degradation and although originally described in plants, it has been discovered across many animal kingdoms from protozoans and invertebrates to higher eukaryotes (reviewed in Agrawal et al., 2003). In physiological settings, the mechanism of RNA interference is triggered by the presence of double-stranded RNA molecules that are cleaved by an RNAse III-like protein active in cells, called Dicer, which releases the 21-23 bp siRNAs. The siRNA, in a homology-driven manner, complexes into a RNA-protein amalgamation termed RISC (RNA-induced silencing complex) in the presence of mRNA to cause degradation resulting in attenuation of that mRNA's expression (Agrawal et al., 2003).

Current approaches to studying the function of genes, such as gene knockout mice and dominant negatives, are often inefficient, and generally expensive, and time-consuming. RNA interference is proving to be a method of choice for the analysis of a large number of genes in a quick and relatively inexpensive manner. Although transfection of synthetic siRNAs is an efficient method, the effects are often transient at best (Hannon G. J., 2002). Delivery of plasmids expressing short hairpin RNAs by stable transfection has been successful in allowing for the analysis of RNA interference in longer-term studies (Brummelkamp et al., 2002; Elbashir et al., 2001). In addition, more recent advances have permitted the expression of siRNA molecules, in the form of short hairpin RNAs, in primary human cells using viral delivery methods such as lentivirus (Lee et al., 2004; Rubinson et al., 2003).

Example 9

Determination of Knockdown Effects on Osteoclastogenesis

In order to develop a screening method for the human candidate genes, RNA interference was adapted to deliver shRNAs into human osteoclast precursor cells so that the expression of the candidate genes could be attenuated. This approach would then allow osteoclast differentiation to be carried out in cells containing decreased expression of these genes to determine their requirement, if any, in this process.

Figure 2:
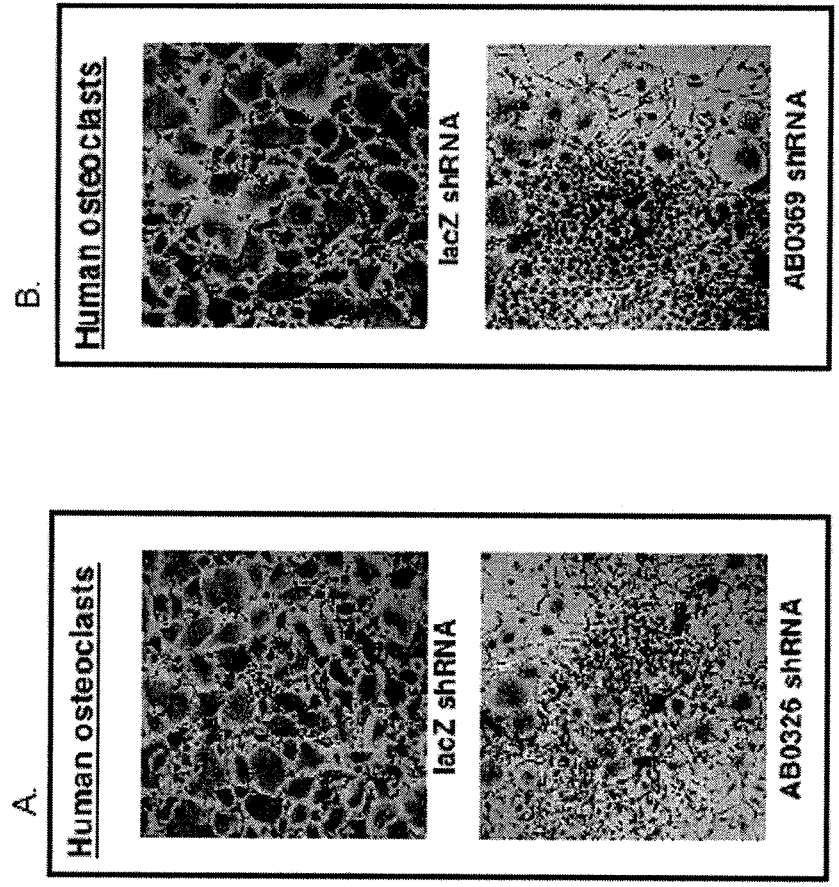
FIG. 2 is a picture showing the knockdown effects on osteoclastogenesis by attenuating the endogenous expression of SEQ. ID. NO.:1 (AB0326). A significant decrease in the number of multinucleated osteoclasts was observed from precursor cells infected with the AB0326 shRNA (FIG. 2A; bottom panel) compared to those with the lacZ shRNA (FIGS. 2A and B; top panels). These results clearly indicated that expression of the gene encoding SEQ. ID. NO.:1 (AB0326) is required for osteoclast differentiation.

To this end, a commercial lentiviral shRNA delivery system (Invitrogen, Burlington, ON) was utilized to introduce specific shRNAs into human osteoclast precursor cells. The techniques used were as described by the manufacturer unless otherwise stated. In this example, the results obtained for the candidate gene, SEQ. ID. NO.:1 (AB0326) are presented. The protein encoded by this gene has no known function. The shRNA sequence used to specifically target SEQ. ID. NO.:1 is 5'-CAGGCCCAGGAGTCCAATT-3' (SEQ. ID. NO.:12). Briefly, a template for the expression of the shRNA was cloned into the lentiviral expression vector and co-transfected in 293FT cells with expression vectors for the viral structural proteins. After two days, supernatants containing the lentivirus were collected and stored at −80° C. Human osteoclast precursors purchased from Cambrex (East Rutherford, N.J.) were seeded in 24-well plates and cultured in complete medium containing macrophage-colony stimulating factor and allowed to adhere for three days. After washing with PBS, the cells were infected with 20 MOIs (multiplicity of infection) of either lentiviral particles containing a shRNA specific for the bacterial lacZ gene as a control (lacZ shRNA) or SEQ. ID. NO.:1 (AB0326 shRNA). After 24 h, the infected cells were treated with same medium containing 100 ng/ml RANK ligand for 5-8 days to allow for differentiation of osteoclast from precursor cells. Mature osteoclasts were fixed with formaldehyde and stained for TRAP expression as follows: the cells were washed with PBS and fixed in 10% formaldehyde for 1 h. After two PBS washes, the cells were lightly permeabilized in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. The stained cells were visualized by light microscopy and photographed (magnification: 40×). A significant decrease in the number of multinucleated osteoclasts was observed from precursor cells infected with the AB0326 shRNA (FIG. 2A; bottom panel) compared to those with the lacZ shRNA (FIG. 2A top panel). Therefore, the lentiviral shRNA perturbed osteoclastogenesis. These results clearly indicated that expression of the gene encoding SEQ. ID. NO.:1 (AB0326) is required for osteoclast differentiation.

Example 10

Biological Validation of the Mouse Orthologue (SEQ ID NO.:4 or 108) for AB0326 (SEQ. ID. NO.: 2) in Osteoclastogenesis Using the RAW 264.7 Model As a means of developing a drug screening assay for the discovery of therapeutic molecules capable of attenuating human osteoclasts differentiation and activity using the targets identified, another osteoclast differentiation model was used. The RAW 264.7 (RAW) osteoclast precursor cell line is well known in the art as a murine model of osteoclastogenesis. However, due to the difficulty in transiently transfecting RAW cells, stable transfection was used as an approach where shRNA are expressed in the RAW cells constitutively. This permitted long term studies such as osteoclast differentiation to be carried out in the presence of specific shRNAs specific to the mouse orthologues of the human targets identified.

RAW cells were purchased from American Type Culture Collection (Manassass, Va.) and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of $4 \times 10^3$ cells/well and allowed to plate for 24 h. Differentiation was induced in high glucose DMEM, 10% charcoal-treated foetal bovine serum (obtained from Hyclone, Logan, Utah), 0.05% BSA, antibiotics, 10 ng/ml macrophage colony stimulating factor (M-CSF), and 100 ng/ml RANK ligand. The plates were re-fed on day 3 and osteoclasts were clearly visible by day 4. Typically, the cells were stained for TRAP on day 4 or 5 unless otherwise indicated.

To incorporate the shRNA-expression cassettes into the RAW cell chromosomes, the pSilencer 2.0 plasmid (SEQ. ID. NO.:15) was purchased from Ambion (Austin, Tex.) and sequence-specific oligonucleotides were ligated as recommended by the manufacturer. Two shRNA expression plasmids were designed and the sequences used for attenuating the mouse ortholog of AB0326 (SEQ. ID. NO.:4 or 108) gene expression were 5'-GCGCCGCGGATCGTCAACA-3' (SEQ. ID. NO.:13) and 5'-ACACGTGCACGGCGGCCAA-3' (SEQ. ID. NO.:14). A plasmid supplied by Ambion containing a scrambled shRNA sequence with no known homology to any mammalian gene was also included as a negative control in these experiments. RAW cells were seeded in 6-well plates at a density of $5 \times 10^5$ cells/well and transfected with 1 µg of each plasmid using Fugene6 (Roche, Laval, QC) as described in the protocol. After selection of stable transfectants in medium containing 2 µg/ml puromycin, the cell lines were expanded and tested in the presence of RANK ligand for osteoclastogenesis.

The stably transfected cell lines were designated RAW-0326.1, RAW-0326.2 and RAW-ctl. In 96-well plates in triplicate, 4 000 cells/well were seeded and treated with 100 ng/ml RANK ligand. After 4 days, osteoclasts were stained for TRAP expression and visualized by light microscopy (magnification was 40× and 100× as depicted in the left and right panels, respectively).

Figure 3:
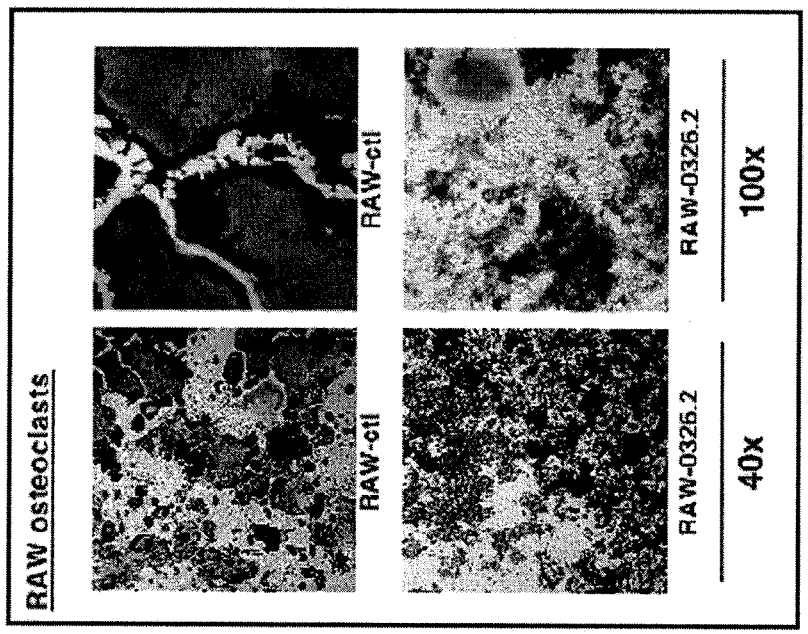
FIG. 3 is a picture showing the knockdown effects on osteoclastogenesis of the mouse orthologue for AB0326 in the RAW 264.7 model using shRNA-0326.2 (SEQ. ID. NO.: 5). The RAW-0326.2 cell line produced significantly less osteoclasts (FIG. 3; bottom panel) compared to the cell line containing the scrambled shRNA (FIG. 3; top panel). This result, coupled with that obtained in the human osteoclast precursor cells using the lentiviral shRNA delivery system demonstrate that in both human and mouse, AB0326 gene product is clearly required for osteoclastogenesis.

The representative results for the RAW-0326.2 line are shown in FIG. 3. The RAW-0326.2 cell line produced significantly less osteoclasts (FIG. 3; bottom panel) compared to the cell line containing the scrambled shRNA (FIG. 3; top panel). The RAW-0326.1 cell line also showed attenuation of the mouse ortholog of AB0326 but not as pronounced (data not shown). Therefore, as observed for the human gene, siRNAs to the mouse orthologue appear to phenotypically perturb osteoclast differentiation in the mouse model as well. These results, coupled with that obtained in the human osteoclast precursor cells using the lentiviral shRNA delivery system (section J), demonstrate that in both human and mouse, AB0326 gene product is clearly required for osteoclastogenesis.

Example 11

A Functional Complementation Assay for SEQ. ID. NO.:1 (AB0326) in RAW 264.6 Cells to Screen for Inhibitors of Osteoclastogenesis To establish a screening assay based on SEQ. ID. NO.:1 and SEQ ID NO.:2 (AB0326) to find small molecules capable of attenuating osteoclast differentiation, the cDNA encoding human AB0326 was introduced into the RAW-0326.2 cell line. Thus, if the human AB0326 plays an identical functional role as the mouse orthologue in RAW 264.7 cells, it should restore the osteoclastogenesis capabilities of the RAW-0326.2 cell line.

Figure 4:
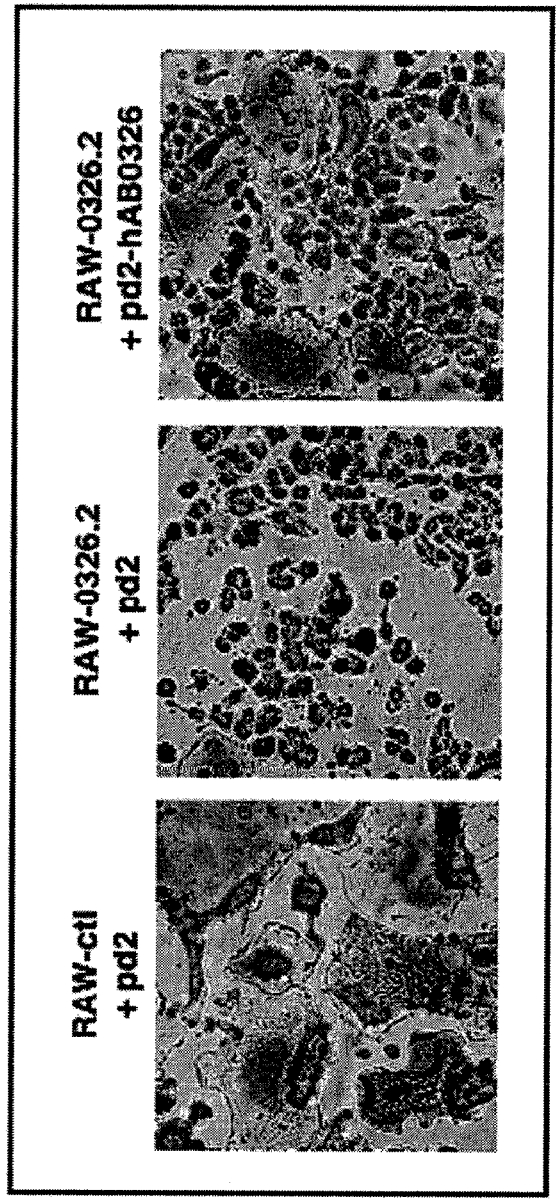
FIG. 4 is a picture showing the results of a functional complementation assay for SEQ. ID. NO.:1 (AB0326) in RAW-0326.2 cells to screen for inhibitors of osteoclastogenesis. The RAW-0326.2 cells transfected with the empty pd2 vector are unable to form osteoclasts in the presence of RANK ligand (center panel) indicating that the mouse AB0326 shRNA is still capable of silencing the AB0326 gene expression in these cells. Conversely, the cells transfected with the cDNA for the human AB0326 (pd2-hAB0326) are rescued and thus, differentiate more efficiently into osteoclasts in response to RANK ligand (right panel). Wild-type RAW 264.7 cells containing the empty vector (pd2) did not adversely affect the formation of osteoclasts in the presence of RANK ligand (left panel) ruling out an effect due to pd2. Thus, this complementation assay can be used to screen for inhibitors of the human AB0326 polypeptide.

To accomplish this task, the RAW-0326.2 cell line was transfected with an eukaryotic expression vector encoding the full length cDNA for human AB0326, termed pd2-hAB0326. This expression vector pd2; (SEQ. ID. NO.:15) was modified from a commercial vector, pd2-EGFP-N1 (Clontech, Mountain View, Calif.) where the EGFP gene was replaced by the full length coding sequence of the human AB0326 cDNA. The AB0326 gene expression was driven by a strong CMV promoter. Stable transfectants were selected using the antibiotic, G418. This resulted in a RAW-0326.2 cell line that expressed the human AB0326 gene product in which, the mouse orthologue of AB0326 was silenced. As a control, RAW-0326.2 cells were transfected with the pd2 empty vector, which should not complement the AB0326 shRNA activity. Also, the pd2 empty vector was transfected into RAW 264.7 cells to serve as a further control. After selection of stable pools of cells, 4 000 cells/well were seeded in 96-well plates and treated for 4 days with 100 ng/ml RANK ligand. Following fixation with formaldehyde, the cells were stained for TRAP, an osteoclast-specific marker gene. As shown in FIG. 4, the RAW-0326.2 cells transfected with the empty pd2 vector are still unable to form osteoclasts in the presence of RANK ligand (center panel) indicating that the mouse AB0326 shRNA is still capable of silencing the AB0326 gene expression in these cells. Conversely, the cells transfected with human AB0326 (pd2-hAB0326) are rescued and thus, differentiate into more osteoclasts in response to RANK ligand (right panel). RAW 264.7 cells containing the empty vector (pd2) did not adversely affect the formation of osteoclasts in the presence of RANK ligand (left panel). These results confirm that the mouse and human orthologues of AB0326 are functionally conserved in osteoclast differentiation.

This particular type of cell-based assay can now serve as the basis for screening compounds capable of binding to and inhibiting the function of human AB0326. A compound library could be applied to this 'rescued' cell line in order to identify molecules (small molecule drugs, peptides, or antibodies) capable of inhibiting AB0326. Any reduction in osteoclast differentiation measured by a reduction in the expression of TRAP would be indicative of a decrease in human AB0326 activity. This assay is applicable to any gene required for proper osteoclast differentiation in RAW cells. A complementation assay can be developed for any human gene and used as the basis for drug screening.

One of skill in the art will readily recognize that orthologues for all mammals may be identified and verified using well-established techniques in the art, and that this disclosure is in no way limited to one mammal. The term "mammal(s)" for purposes of this disclosure refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The sequences in the experiments discussed above are representative of the NSEQ being claimed and in no way limit the scope of the invention. The disclosure of the roles of the NSEQs in osteoclastogenesis and osteoclast function satisfies a need in the art to better understand the bone remodeling process, providing new compositions that are useful for the diagnosis, prognosis, treatment, prevention and evaluation of therapies for bone remodeling and associated disorders.

The art of genetic manipulation, molecular biology and pharmaceutical target development have advanced considerably in the last two decades. It will be readily apparent to those skilled in the art that newly identified functions for genetic sequences and corresponding protein sequences allows those sequences, variants and derivatives to be used directly or indirectly in real world applications for the development of research tools, diagnostic tools, therapies and treatments for disorders or disease states in which the genetic sequences have been implicated.

Example 12

Antibodies and Antigen Binding Fragments Binding to Siglec-15 to a Siglec-15 Analogue This example provides details pertaining to the family of monoclonal antibodies that bind to Siglec-15.

To generate monoclonal antibodies, recombinant human Siglec-15 was produced in 293E cells using the large-scale transient transfection technology (Durocher et al., 2002; Durocher, 2004). A cDNA encoding amino acids 20-259 of SEQ ID NO.:2 (see SEQ ID NO.:16) was amplified by PCR using a forward primer that incorporated a BamHI restriction site (SEQ ID NO.:17) and a reverse primer that incorporated a NotI restriction site (SEQ ID NO.:18). The resulting PCR product was digested with BamHI and NotI and the fragment was ligated into the expression vector pYD5 (SEQ ID NO.: 19) that was similarly digested with the same restriction enzymes to create a vector called pYD5-0326. The pYD5 expression plasmid contains the coding sequence for the human Fc domain that allows fusion proteins to be generated as well as the sequence encoding the IgG1 signal peptide to allow the secretion of the fusion protein into the culture medium. For each milliliter of cells, one microgram of the expression vector, called pYD5-0326$_{20\text{-}259}$, was transfected in 293E cells grown in suspension to a density of 1.5-2.0 million cells/ml. The transfection reagent used was polyethylenimine (PEI), (linear, MW 25,000, Cat#23966 Polysciences, Inc., Warrington, Pa.) which was included at a DNA:PEI ratio of 1:3. Growth of the cells was continued for 5 days after which the culture medium was harvested for purification of the recombinant Fc-0326$_{20\text{-}259}$ fusion protein. The protein was purified using Protein-A agarose as instructed by the manufacturer (Sigma-Aldrich Canada Ltd., Oakville, ON). A representative polyacrylamide gel showing a sample of the purified Fc-0326$_{20\text{-}259}$ (indicated as Fc-Siglec-15$_{20\text{-}259}$) is shown in FIG. 3.

The antibodies that bind Siglec-15 were generated using the Biosite phage display technology. A detailed description of the technology and the methods for generating these antibodies can be found in the U.S. Pat. No. 6,057,098. Briefly, the technology utilizes stringent panning of phage libraries that display the antigen binding fragments (Fabs). After a several rounds of panning, a library, termed the Omniclonal, was obtained that was enriched for recombinant Fabs containing light and heavy chain variable regions that bound to Siglec-15 with very high affinity and specificity. From this library, more precisely designated Omniclonal AL0025Z1, 96 individual recombinant monoclonal Fabs were prepared from E. coli and tested for Siglec-15 binding.

To measure the relative binding of each individual monoclonal antibody, recombinant human Fc-Siglec-$15_{20-259}$ was produced in 293E cells using the large-scale transient transfection technology (Durocher et al., 2002; Durocher, 2004). The 96-well master plate of monoclonal preparations contained different concentrations of purified anti-Siglec-15 Fabs in each well. A second stock master plate was prepared by diluting the Fabs to a final concentration of 10 µg/ml from which all subsequent dilutions were performed for ELISA measurements. To carry out the binding of Fc-Siglec-15 to the monoclonal preparations, the Fc-Siglec-$15_{20-259}$ was biotinylated with NHS-biotin (Pierce, Rockford, Ill.) and 10 ng/well was coated in a streptavidin 96-well plate. One nanogram of each Fab monoclonal preparation was added to each well and incubated at room temperature for 30 minutes. Bound antibody was detected with HRP-conjugated mouse anti-kappa light chain antibody in the presence of TMB liquid substrate (Sigma-Aldrich Canada Ltd., Oakville, ON) and readings were conducted at 450 nm in microtiter plate reader. As shown in FIG. 4A, a total of 53 (highlighted dark grey) monoclonal antibodies displayed significant binding in this assay (>0.2 arbitrary $OD_{450}$ units). The antibodies were purposely diluted to 1 ng/well to accentuate the binding of those antibodies with the most affinity for Siglec-15. Since the antibodies were generated using a Fc fusion protein, the monoclonals were also tested in an ELISA using biotinylated Fc domain only. As shown on FIG. 4B, 17 antibodies interacted with the Fc moiety of the Fc-Siglec-$15_{20-259}$ (highlighted light grey). The values presented in bold (see FIG. 4) represent the exemplary antibodies 25A1, 25B4, 25B8, 25C1, 25D8, 25E5, 25E6, and 25E9. These data also revealed that the binding of the antibodies varied from well to well indicating that they exhibited different affinities for Siglec-15.

The applicant noted that the antibody or antigen binding fragment of the present invention may bind efficiently to the antigen, in fact it was found that 1 ng of antibody is capable of binding to less than 500 ng of SEQ ID NO.:2.

The nucleic acid and amino acid sequence of selected antibodies light chain or heavy chain is listed in Table 1. The nucleic acid and amino acid sequence of selected antibodies light chain variable region or heavy chain variable region is listed in Table 2

TABLE 1

Complete sequences of light and heavy chain immunoglobulins that bind to Siglec-15

| Antibody designation | Chain type | Nucleotide sequence (SEQ ID NO.:) | Amino acid sequence (SEQ ID NO.:) |
|---|---|---|---|
| 25A1 | Light (L) | 20 | 21 |
| 25A1 | Heavy (H) | 22 | 23 |
| 25B4 | Light | 24 | 25 |
| 25B4 | Heavy | 26 | 27 |
| 25B8 | Light | 28 | 29 |
| 25B8 | Heavy | 30 | 31 |
| 25C1 | Light | 32 | 33 |
| 25C1 | Heavy | 34 | 35 |
| 25D8 | Light | 36 | 37 |
| 25D8 | Heavy | 38 | 39 |
| 25E5 | Light | 40 | 41 |
| 25E5 | Heavy | 42 | 43 |
| 25E6 | Light | 44 | 45 |
| 25E6 | Heavy | 46 | 47 |
| 25E9 | Light | 48 | 49 |
| 25E9 | Heavy | 50 | 51 |

TABLE 2

Sequences of light and heavy chain variable regions that bind to Siglec-15

| Antibody designation | Chain type | Nucleotide sequence (SEQ ID NO.:) | Amino acid sequence (SEQ ID NO.:) |
|---|---|---|---|
| 25A1 | Light (L) | 52 | 53 |
| 25A1 | Heavy (H) | 54 | 55 |
| 25B4 | Light | 56 | 57 |
| 25B4 | Heavy | 58 | 59 |
| 25B8 | Light | 60 | 61 |
| 25B8 | Heavy | 62 | 63 |
| 25C1 | Light | 64 | 65 |
| 25C1 | Heavy | 66 | 67 |
| 25D8 | Light | 68 | 69 |
| 25D8 | Heavy | 70 | 71 |
| 25E5 | Light | 72 | 73 |
| 25E5 | Heavy | 74 | 75 |
| 25E6 | Light | 76 | 77 |
| 25E6 | Heavy | 78 | 79 |
| 25E9 | Light | 80 | 81 |
| 25E9 | Heavy | 82 | 83 |

Example 13

Conversion of Fabs into Chimeric Antibodies

Figure 5:
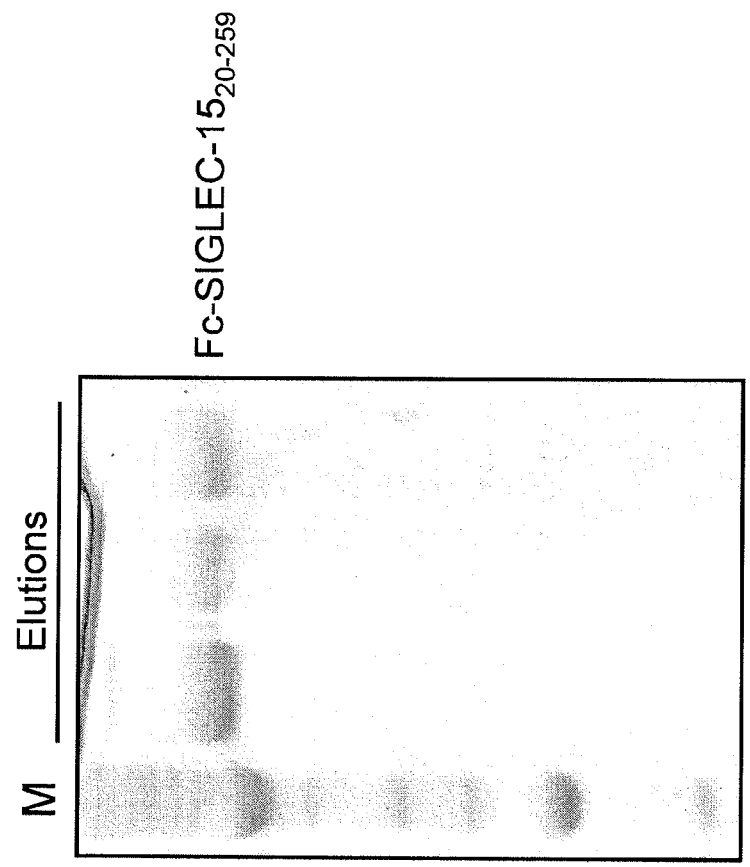
FIG. 5 presents a Coomassie-stained polyacrylamide gel containing a sample of the purified human recombinant Siglec-15 that was expressed as a Fc fusion protein in 293-6E cells. This preparation was used to generate the monoclonal antibodies described herein

This example discloses the methods used to convert the Fabs into full IgG2 chimeric monoclonal antibodies. A scheme of the methodology is presented in FIG. 5.

In order to conduct in vitro and in vivo studies to validate the biological function of the antigen the light and heavy chain variable regions contained in the Fabs was transferred to full antibody scaffolds, to generate mouse-human chimeric IgG2s. The expression vectors for both the light and heavy immunoglobulin chains were constructed such that i) the original bacterial signal peptide sequences upstream of the Fab expression vectors were replaced by mammalian signal peptides and ii) the light and heavy chain constant regions in the mouse antibodies were replaced with human constant regions. The methods to accomplish this transfer utilized standard molecular biology techniques that are familiar to those skilled in the art. A brief overview of the methodology is described here (see FIG. 5).

Light chain expression vector—an existing mammalian expression plasmid, called pTTVH8G (Durocher et al., 2002), designed to be used in a 293E transient transfection system was modified to accommodate the mouse light chain variable region. The resulting mouse-human chimeric light chain contained a mouse variable region followed by the human kappa constant domain. The cDNA sequence encoding the human kappa constant domain was amplified by PCR with primers OGS1773 and OGS1774 (SEQ ID NOS:84 and 85, respectively). The nucleotide sequence and the corresponding amino acid sequence for the human kappa constant region are shown in SEQ ID NOS:86 and 87, respectively. The resulting 321 base pair PCR product was ligated into pTTVH8G immediately downstream of the signal peptide sequence of human VEGF A (NM_003376). This cloning step also positioned unique restriction endonuclease sites that permitted the precise positioning of the cDNAs encoding the mouse light chain variable regions. The sequence of the final expression plasmid, called pTTVK1, is shown in SEQ ID NO.:88. Based on the sequences disclosed in Table 2, PCR primers specific for the light chain variable regions of antibodies 25A1, 25B4, 25B8, 25C1, 25D8, 25E5, 25E6, and 25E9 were designed that incorporated, at their 5'-end, a sequence identical to the last 20 base pairs of the VEGF A signal peptide. The sequences of these primers are shown in SEQ ID NO.:89 for 25A1; SEQ ID NO.:90 for 25B4, 25B8, 25C1, 25D8, and 25E9; SEQ ID NO.:91 for 25E5, and SEQ ID NO.:92 for 25E6, respectively. The same reverse primer was used to amplify all four light chain variable regions since the extreme 3'-ends were identical. This primer (SEQ ID NO.:93) incorporated, at its 3'-end, a sequence identical to the first 20 base pairs of the human kappa constant domain. Both the PCR fragments and the digested pTTVK1 were treated with the 3'-5' exonuclease activity of T4 DNA polymerase resulting in complimentary ends that were joined by annealing. The annealing reactions were transformed into competent *E. coli* and the expression plasmids were verified by sequencing to ensure that the mouse light chain variable regions were properly inserted into the pTTVK1 expression vector. Those skilled in the art will readily recognize that the method used for construction of the light chain expression plasmids applies to all anti-Siglec-15 antibodies contained in the original Fab library.

Heavy chain expression vector—the expression vector that produced the heavy chain immunoglobulins was designed in a similar manner to the pTTVK1 described above for production of the light chain immunoglobulins. In the case of the chimeric anti-Siglec-15 antibodies, IgG2 isotype was required which is the preferred type for stable, blocking antibodies. To this end, the constant regions (CH1, CH2, and CH3) of the human IgG2 immunoglobulin were amplified and ligated into a pre-existing IgG1 expression vector and the detailed methods are described herein. Plasmid pYD11 (Durocher et al., 2002), which contains the human IgGK signal peptide sequence as well as the CH2 and CH3 regions of the human Fc domain of IgG1, was modified by ligating the cDNA sequence encoding the human constant CH1 region. PCR primers OGS1769 and OGS1770 (SEQ ID NOS:94 and 95), designed to contain unique restriction endonuclease sites, were used to amplify the human IgG1 CH1 region containing the nucleotide sequence and corresponding amino acid sequence shown in SEQ ID NOS:96 and 97. Following ligation of the 309 base pair fragment of human CH1 immediately downstream of the IgGK signal peptide sequence, the resulting plasmid was digested with the restriction enzymes ApaI and NsiI. These enzymes that digest both the constant IgG1 and IgG2 cDNAs in exactly the same positions that permits the IgG1 constant sequence to be replaced by the human IgG2 sequence in the expression vector. The cDNA encoding the human IgG2 constant domains was obtained from a commercially available source (Open Biosystems, Huntsville, Ala.). The final plasmid used to express the IgG2 immunoglobulin heavy chain was designated pYD19 and the sequence is shown in SEQ ID NO.:98. When a selected heavy chain variable region is ligated into this vector, the resulting plasmid encodes a full IgG2 heavy chain immunoglobulin with human constant regions. Based on the sequences disclosed in Table 2, PCR primers specific for the heavy chain variable regions of antibodies 25A1, 25B4, 25B8, 25C1, 25D8, 25E5, 25E6, and were designed that incorporated, at their 5'-end, a sequence identical to the last 20 base pairs of the IgGK signal peptide. The sequences of these primers are shown in SEQ ID NO.:99 for 25A1; SEQ ID NO.:100 for 24B4 and 25D8; SEQ ID NO.:101 for 25B8, 25C1, and 25E9; SEQ ID NO.:102 for 25E5; and SEQ ID NO.:103 for 25E6, respectively. The same reverse primer was used to amplify all four heavy chain variable regions since the extreme 3'-ends were identical. This primer (SEQ ID NO.:104) incorporated, at its 3'-end, a sequence identical to the first 20 base pairs of the human CH1 constant domain. Both the PCR fragments and the digested pYD19 were treated with the 3'-5' exonuclease activity of T4 DNA polymerase resulting in complimentary ends that were joined by annealing. The annealing reactions were transformed into competent *E. coli* and the expression plasmids were verified by sequencing to ensure that the mouse heavy chain variable regions were properly inserted into the pYD19 expression vector. Those skilled in the art will readily recognize that the method used for construction of the heavy chain expression plasmids applies to all anti-Siglec-15 antibodies contained in the original Fab library.

Expression of human IgG2s in 293E cells—The expression vectors prepared above that encoded the light and heavy chain immunoglobulins were expressed in 293E cells using the transient transfection system (Durocher et al., 2002). By virtue of the signal peptides incorporated at the amino-termini of both immunoglobulin chains, the mature IgG2 was harvested from the serum-free culture medium of the cells. The methods used for co-transfecting the light and heavy chain expression vectors were described herein. For each milliliter of cells, one microgram of a combination of both the light and heavy chain expression plasmids was transfected in 293E cells grown in suspension to a density of 1.5-2.0 million cells/ml. The ratio of light to heavy chain plasmid was optimized in order to achieve the most yield of antibody in the tissue culture medium and it was found to be 9:1 (L:H). The transfection reagent used was polyethylenimine (PEI), (linear, MW 25,000, Cat#23966 Polysciences, Inc., Warrington, Pa.) which was included at a DNA:PEI ratio of 1:3. Growth of the cells was continued for 5 days after which the culture medium was harvested for purification of the IgG2 chimeric monoclonal antibodies. The protein was purified using Protein-A agarose as instructed by the manufacturer (Sigma-Aldrich Canada Ltd., Oakville, ON).

To determine the relative binding affinity of selected monoclonals more accurately, increasing concentration of the Fabs was incubated with biotinylated Fc-Siglec-15$_{20-259}$. Ten nanograms of biotinylated Fc-Siglec-15$_{20-259}$ was coated in streptavidin microtiter plates and increasing amounts of either Fabs or the chimeric IgG2 monoclonals 25B4, 25B8, 25C1, 25D8, 25E6, and 25E9 were added as indicated in FIG. 6. As depicted in FIG. 6, the binding of the 25B4, 2588, 25C1, 25D8, 25E6, and 25E9 chimeric IgG2 monoclonal antibodies was very similar to the Fabs. This result shows that the transposition of the variable domains from the mouse Fabs into a human IgG2 backbone did not significantly affect the capacity of the light and heavy chain variable regions to confer Siglec-15 binding.

Example 14

Inhibition of Siglec-15 Activity

This example describes the use of anti-Siglec-15 antibodies for inhibiting the differentiation of osteoclasts.

Figure 7:
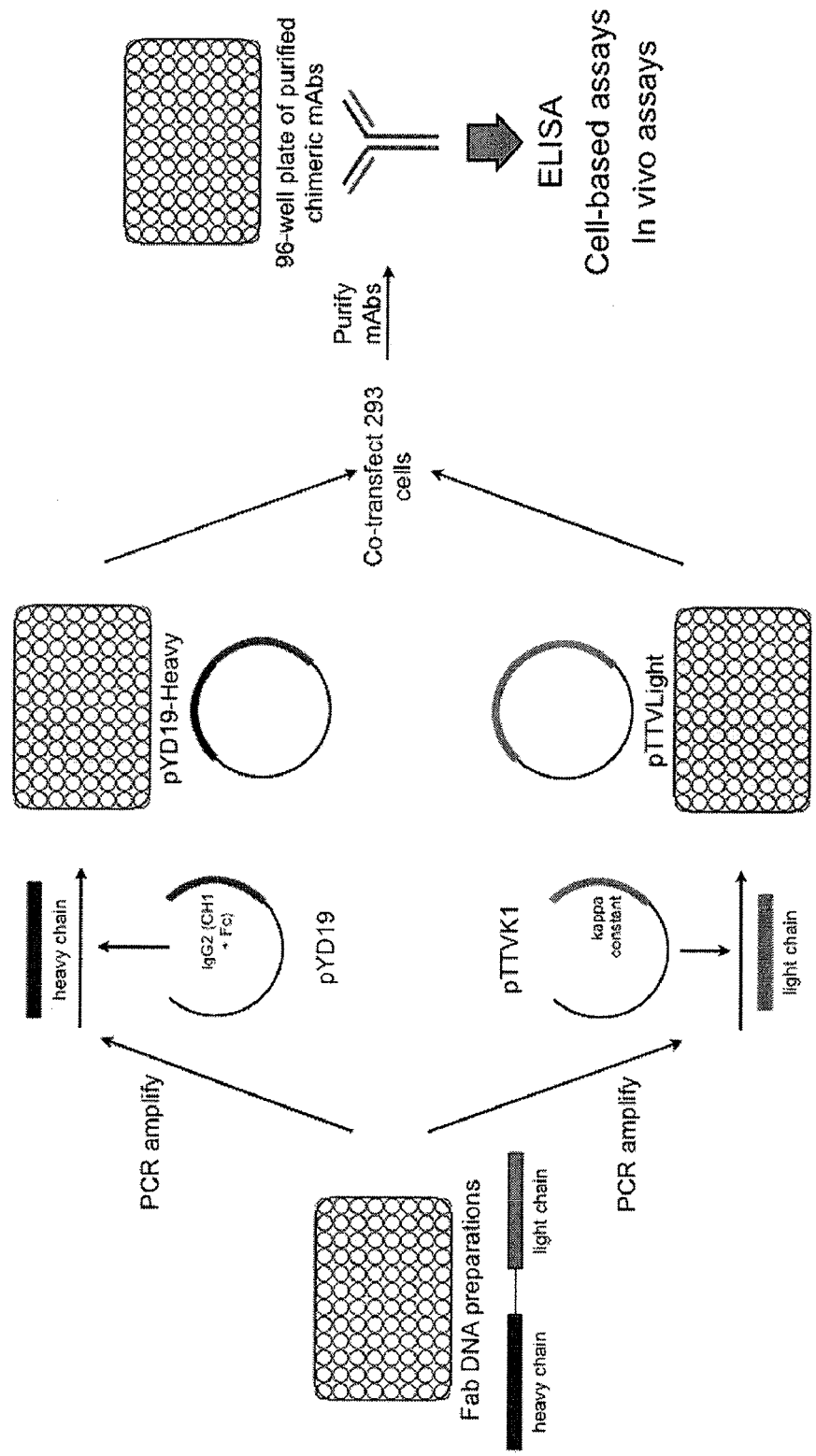
FIG. 7 presents a scheme that illustrates the steps involved to convert the mouse Fabs into IgG2 mouse-human chimeric mAbs.

Human PBMNCs (AllCells, Emoryville, Calif.) were placed in the appropriate culture medium for 24 h at 37 C in a 5% $CO_2$ atmosphere. The cells were seeded in 96-well plates at a cell density of 100,000 cells/ml and treated with increasing concentration (0.01 µg/ml-100 µg/ml) of anti-Siglec-15 IgG2 chimeric monoclonal antibodies in the presence of 35 ng/ml M-CSF and 30 ng/ml RANKL. Undifferentiated precursor cells were treated only with M-CSF, The control wells were treated with a non-Siglec-15 binding IgG2. The cells were fixed, stained for TRAP, and multinucleated cells counted and photographed (magnification 40×). As depicted in FIG. 7, mAbs targeting Siglec-15 could efficiently inhibit the differentiation of human osteoclasts in a dose-dependent manner. Inhibition of osteoclast differentiation was observed to varying extents with every exemplary Siglec-15 antibody that was tested but the most active monoclonals were 25B8, 25E6, and 25E9. Cells treated with a control chimeric IgG2 were not inhibited (see lower right panels in FIG. 8, Control IgG2). This result is in complete agreement with the experiments disclosed by Sooknanan (Sooknanan et al., 2007) that showed that knockdown of Siglec-15 expression by RNA interference caused inhibition of human osteoclast differentiation.

Figure 8:
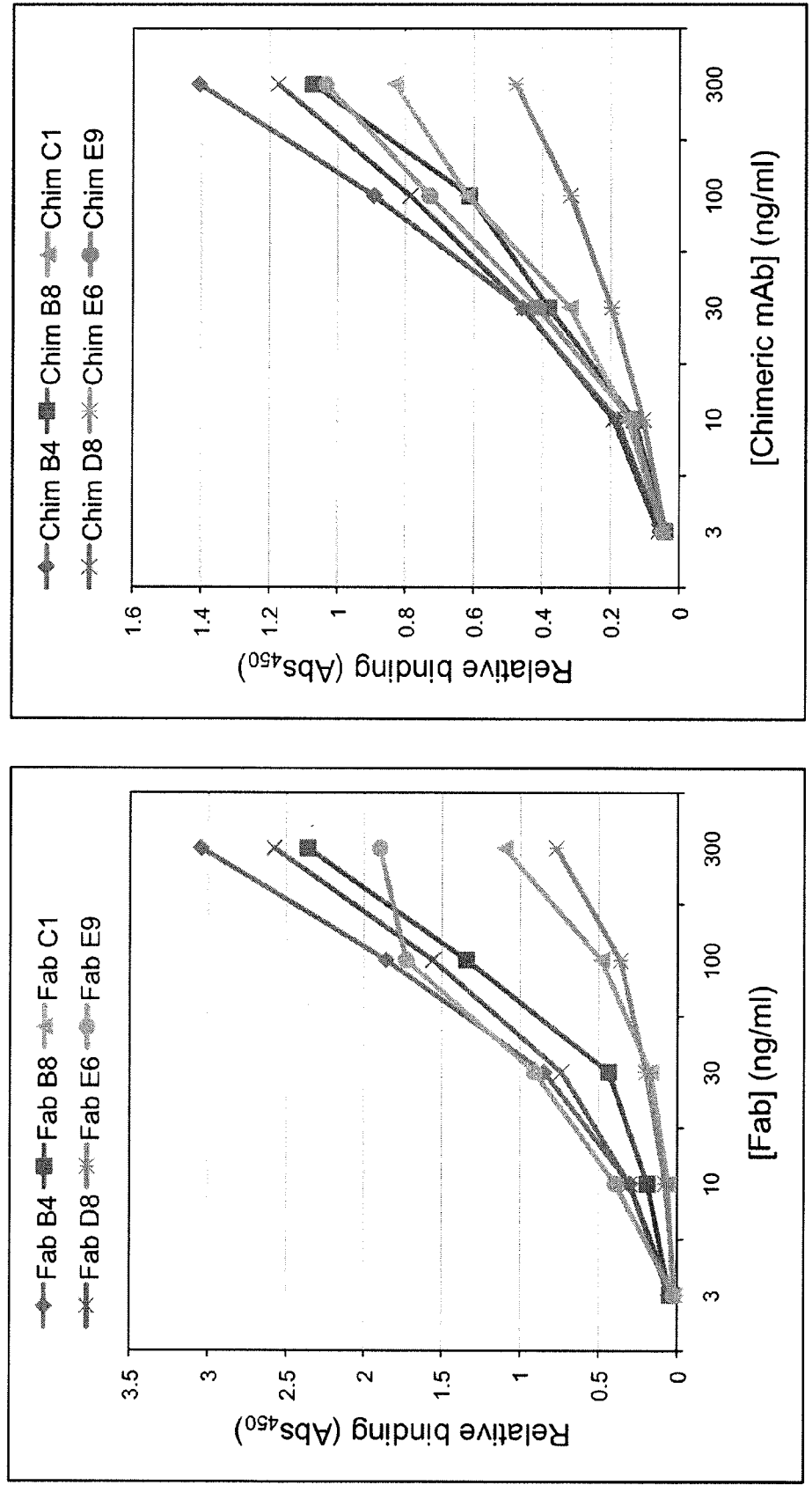
FIG. 8 shows drawings that compare the binding of the mouse anti-Siglec-15 Fabs with the binding of the corresponding IgG2 chimeric monoclonal antibodies for exemplary antibodies 25B4, 25B8, 25C1, 25D8, 25E6, and 25E9. The results indicate that the relative binding of the Fab variable regions was maintained when transferred to a full human IgG2 scaffold.

In a parallel experiment, mouse PBMNCs were treated in a similar manner. As depicted in FIG. 8, anti-Siglec-15 chimeric antibodies could inhibit the differentiation of mouse osteoclasts as exemplified by the chimeric mAbs designated 25B8, 25E6, and 25D8. This result confirms that the monoclonal antibodies that were generated against the human orthologue of Siglec-15 are cross-reactive against the mouse Siglec-15 protein as well. This was experimentally verified using an ELISA. A fragment of the mouse Siglec-15 cDNA was amplified corresponding to amino acids 21-256 using oligonucleotides containing the sequences shown in SEQ ID NOS: 105 and 106. This PCR fragment was ligated into the pYD5 expression vector as was described for the human Siglec-15 fragment for expression in 293-6E cells. The recombinant Fc-mouseSiglec-15 was purified using Protein-A affinity chromatography.

Figure 9:
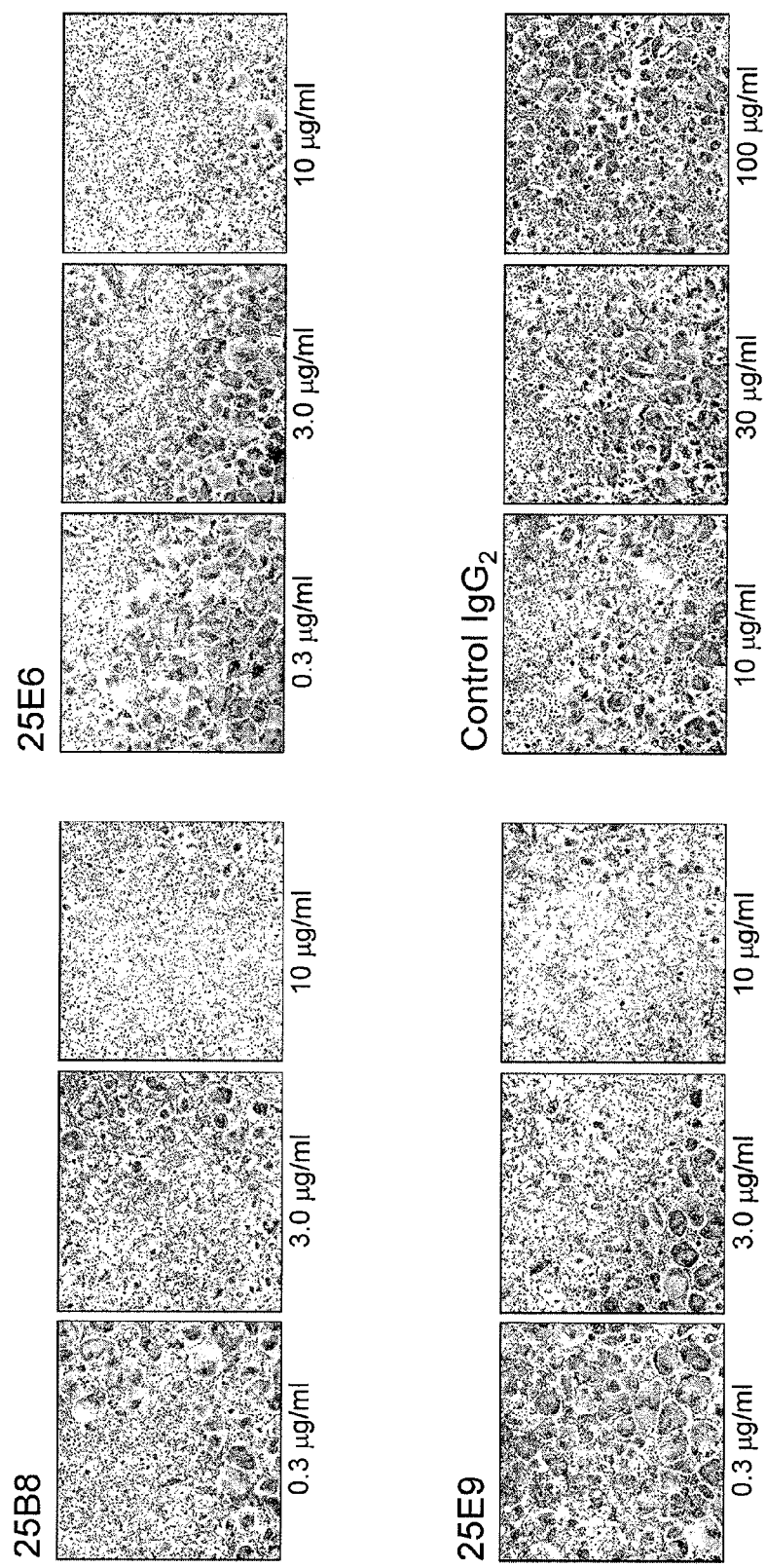
FIG. 9 shows the inhibition of the differentiation of human osteoclasts upon treatment with increasing concentrations of anti-Siglec-15 IgG2 chimeric monoclonal antibodies 25B8, 25E6, and 25E9. After treatment, the osteoclasts were stained for TRAP expression.
Figure 10:
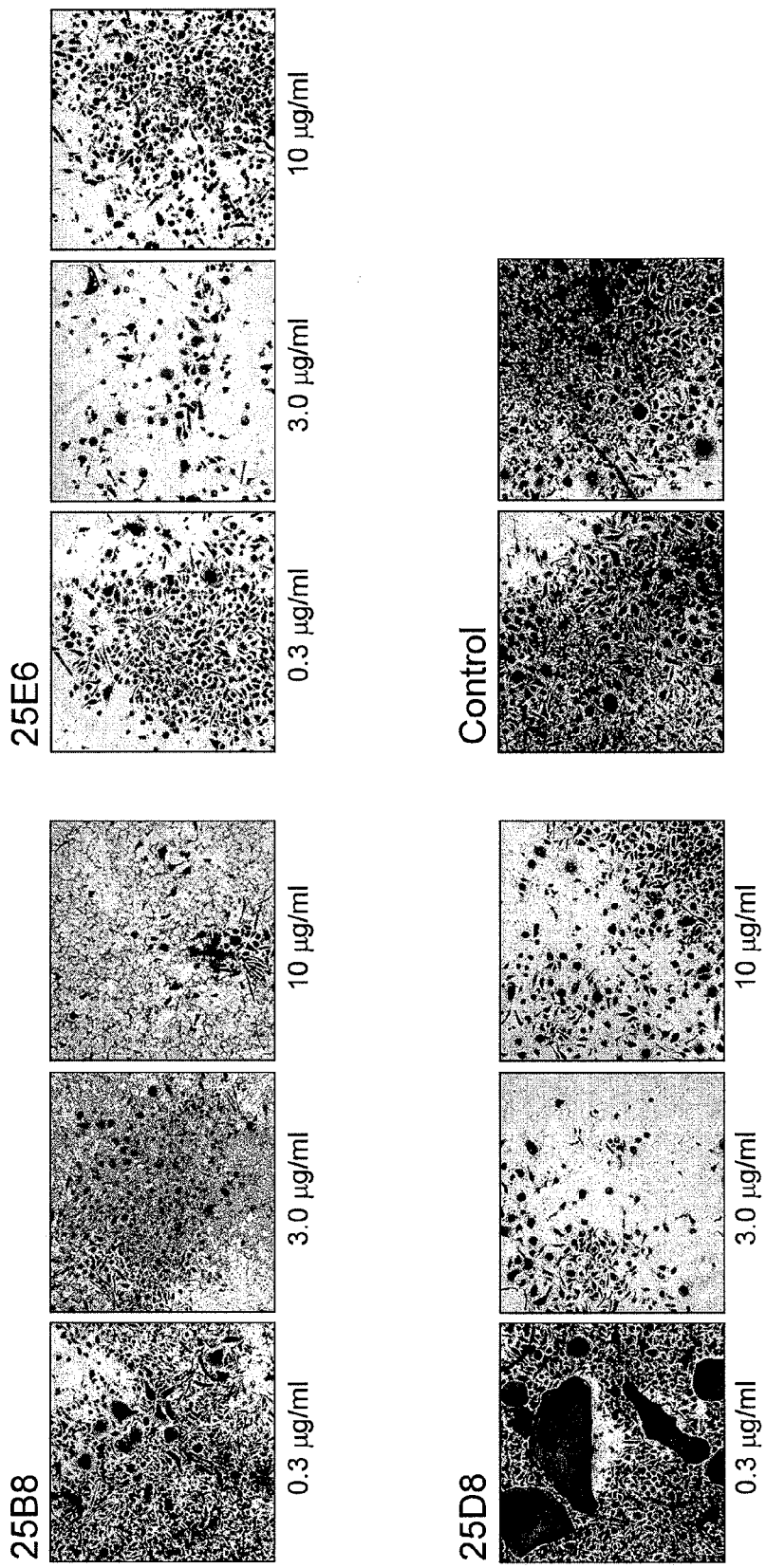
FIG. 10 shows the inhibition of the differentiation of mouse osteoclasts upon treatment with increasing concentrations of anti-Siglec-15 IgG2 chimeric monoclonal antibodies 25B8, 25E6, and 25D8. After treatment, the osteoclasts were stained for TRAP expression.
Figure 11:
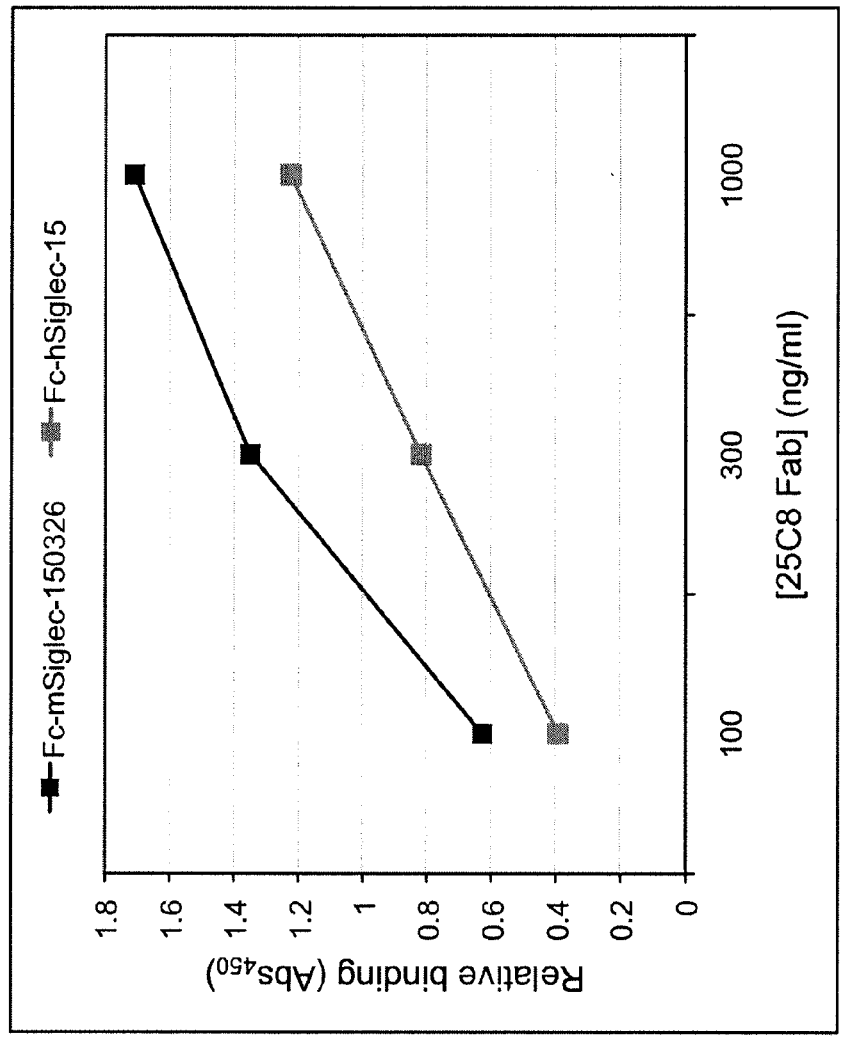
FIG. 11 shows the comparative binding of the human and mouse Siglec-15 in the presence of the exemplary antibody 25C8. The result indicates that the binding of the antibodies generated against the human Siglec-15 also interact with the mouse Siglec-15.

An exemplary anti-Siglec-15 monoclonal Fab designated 25C8 was incubated with either Fc-human(h)Siglec-$15_{20-259}$ or Fc-mouse(m)Siglec-$15_{21-256}$. The results (see FIG. 9) indicate that the binding activity of the antibodies that were generated against the human Siglec-15 also cross-react with the mouse orthologue of Siglec-15.

The results described above clearly demonstrate the importance of Siglec-15 in osteoclastogenesis. Attenuation of Siglec-15 expression in osteoclast precursor cells results in cells that are highly impaired in their ability to form multinucleated mature osteoclasts. Thus, targeting Siglec-15 with an inhibitor, in particular a therapeutic monoclonal antibody, would prove to be a very selective way to target those cells that are directly responsible for bone degradation during acute metastatic bone cancer or chronic osteoporosis.

Example 5

Inhibition of Siglec-15 Activity

This example evaluates the ability of anti-Siglec-15 antibodies in inhibiting bone resorption activity.

The OsteoLyse™ Assay (Human Collagen) made by Lonza provides a 96-well OsteoLyse™ Cell Culture Plate coated with fluorophore-derivatized human bone matrix (europiumconjugated collagen) for use in assays of osteoclast differentiation and function. The assay is a direct measure of the release of matrix metalloproteinases into the resorption lacuna of the osteoclast1. Cells can be seeded onto the surface of the OsteoLyse™ Plate in a manner identical to that used in traditional cell culture protocols. The resorptive activity of the osteoclasts, as reflected by the release of Eu-labeled collagen fragments, can be measured by simply sampling the cell culture supernatant after an appropriate period of cell culture. The cell culture supernatants are added to Fluorophore-Releasing Reagent in a second 96-well assay plate and counted using time-resolved fluorescence2.

Human PBMNCs (AllCells, Emoryville, Calif.) are placed in the appropriate culture medium for 24 h at 37 C in a 5% $CO_2$ atmosphere. The cells are seeded in a osteolysis assay plate at a cell density of 100,000 cells/ml and treated with increasing concentration (0.01 µg/ml-100 µg/ml) of anti-Siglec-15 IgG2 chimeric monoclonal antibodies in the presence of 35 ng/ml M-CSF and 30 ng/ml RANKL and appropriate culture medium.

After 3 days left in culture, 10 µL of the culture supernatant is removed, and treated with 200 µL of the Fluorophore Releasing Reagent. The quantity of free fluorescent collagen fragments released in the culture supernatant is determined by measuring the fluorescence intensity using a fluorescent plate reader.

Although the present invention has been described hereinabove by way of preferred embodiments thereof, it may be modified, without departing from the spirit and nature of the subject invention as defined in the appended claims.

REFERENCES

Patents

U.S. Pat. No. 5,712,127 Malek et al., Jan. 27, 1998
U.S. Pat. No. 6,498,024, Malek et al., Dec. 24, 2002
U.S. patent application Ser. No. 11/000,958 field on Dec. 2, 2003 published under No. US 2005/0153333A1 on Jul. 14, 2005 and entitled "Selective Terminal Tagging of Nucleic Acids"
U.S. Pat. No. 6,617,434 Duffy, Sep. 9, 2003
U.S. Pat. No. 6,451,555 Duffy, Sep. 17, 2002

OTHER REFERENCES

1. Frost H. M., 1964 Dynamics of Bone Remodeling. In: Bone Biodynamics, Little and Brown, Boston, Mass., USA pp. 315;
2. Baron, R., Anatomy and Biology of Bone Matrix and Cellular Elements, In: Primer on the Metabolic Bone Diseases and Disorders of Mineral Metabolism, Fifth Edition 2003, American Society for Bone and Mineral Research, Washington D.C., pp. 1-8;
3. Jilka, R. L. et al., "Increased Osteoclast Development After Esgtrogen Loss: Mediation by Interleukin-6", Science 257: 88-91 (1992).
4. Poli, V. et al., "Interleukin-6 deficient mice are protected from bone loss caused by estrogen depletion", EMBO J. 13: 1189-1196 (1994).
5. Srivastava, S. et al., "Estrogen Blocks M-CSF Gene Expression and Osteoclast Formation by Regulating Phosphorylation of Egr-1 and Its Interaction with Sp-1", J Clin Invest 102: 1850-1859 (1998).

6. de Vernejoul, M. C., "Dynamics of Bone Remodeling: Biochemical and Pathophysiological Basis", Eur J Clin Chem Clin Biochem 34: 729-734 (1996).
7. Netzel-Arnett, S., J. D. Hooper, et al. (2003). "Membrane anchored serine proteases: a rapidly expanding group of cell surface proteolytic enzymes with potential roles in cancer." Cancer Metastasis Rev 22(2-3): 237-58.
8. Shan, J., L. Yuan, et al. (2002). "TSP50, a possible protease in human testes, is activated in breast cancer epithelial cells." Cancer Res 62(1): 290-4.
9. Yuan, L., J. Shan, et al. (1999). "Isolation of a novel gene, TSP50, by a hypomethylated DNA fragment in human breast cancer." Cancer Res 59(13): 3215-21.
10. Nishi, T. and M. Forgac (2002). "The vacuolar (H+)-ATPases—nature's most versatile proton pumps." Nat Rev Mol Cell Biol 3(2): 94-103.
11. Nishi, T., S. Kawasaki-Nishi, et al. (2003). "Expression and function of the mouse V-ATPase d subunit isoforms." J Biol Chem 278(47): 46396-402.
12. Morello, R., L. Tonachini, et al. (1999). "cDNA cloning, characterization and chromosome mapping of Crtap encoding the mouse cartilage associated protein." Matrix Biol 18(3): 319-24.
13. Tonachini, L., R. Morello, et al. (1999). "cDNA cloning, characterization and chromosome mapping of the gene encoding human cartilage associated protein (CRTAP)." Cytogenet Cell Genet. 87(3-4): 191-4.
14. Kawai, J., A. Shinagawa, et al. (2001). "Functional annotation of a full-length mouse cDNA collection." Nature 409(6821): 685-90.
15. Strausberg, R. L., E. A. Feingold, et al. (2002). "Generation and initial analysis of more than 15,000 full-length human and mouse cDNA sequences." Proc Natl Acad Sci USA 99(26): 16899-903.
16. Janssen, E., M. Zhu, et al. (2003). "LAB: a new membrane-associated adaptor molecule in B cell activation." Nat Immunol 4(2): 117-23.
17. Kawaida, R., T. Ohtsuka, et al. (2003). "Jun dimerization protein 2 (JDP2), a member of the AP-1 family of transcription factor, mediates osteoclast differentiation induced by RANKL." J Exp Med 197(8): 1029-35.
18. Agrawal, N., P. V. Dasaradhi, et al. (2003). "RNA interference: biology, mechanism, and applications." Microbiol Mol Biol Rev 67(4): 657-85.
19. Hannon, G. J. (2002). "RNA interference." Nature 418 (6894): 244-51.
20. Brummelkamp, T. R., R. Bernards, et al. (2002). "A system for stable expression of short interfering RNAs in mammalian cells." Science 296(5567): 550-3.
21. Elbashir, et al. (2001). "Duplexes of 21-nucleotide RNAs mediate RNA interference in cultured mammalian cells." Nature 411(6836): 494-8.
22. Lee, J. S., Z. Hmama, et al. (2004). "Stable gene silencing in human monocytic cell lines using lentiviral-delivered small interference RNA. Silencing of the p110alpha isoform of phosphoinositide 3-kinase reveals differential regulation of adherence induced by 1alpha,25-dihydroxycholecalciferol and bacterial lipopolysaccharide." J Biol Chem 279(10): 9379-88.
23. Rubinson, D. A., C. P. Dillon, et al. (2003). "A lentivirus-based system to functionally silence genes in primary mammalian cells, stem cells and transgenic mice by RNA interference." Nat Genet 33(3): 401-6.
24. Boyle, W. J., W. S. Simonet, et al. (2003). "Osteoclast differentiation and activation." Nature 423(6937): 337-42.
25. Gee et al. In: Huber and Carr (1994) Molecular and Immunologic Approaches, Futura Publishing Co., Mt. Kisco N.Y., pp. 163-177.
26. Smith, A. N., F. Jouret, et al. (2005). "Vacuolar H+-ATPase d2 subunit: molecular characterization, developmental regulation, and localization to specialized proton pumps in kidney and bone." J Am Soc Nephrol 16(5): 1245-56
27. Smith, A. N., J. Skaug, et al. (2000). "Mutations in ATP6NIB, encoding a new kidney vacuolar proton pump 116-kD subunit, cause recessive distal renal tubular acidosis with preserved hearing." Nat Genet 26(1): 71-5.
28. Stehberger, P. A., N. Schulz, et al. (2003). "Localization and regulation of the ATP6V0A4 (a4) vacuolar H+-ATPase subunit defective in an inherited form of distal renal tubular acidosis." J Am Soc Nephrol 14(12): 3027-38.
29. Malkin I, Dahm S, Suk A, Kobyliansky E, Toliat M, Ruf N, Livshits G, Nurnberg P. Association of ANKH gene polymorphisms with radiographic hand bone size and geometry in a Chuvasha population. Bone. 2005 February; 36(2):365-73.
30. McMahon C, Will A, Hu P, Shah G N, Sly W S, Smith O P. Bone marrow transplantation corrects osteopetrosis in the carbonic anhydrase II deficiency syndrome. Blood. 2001 Apr. 1; 97(7):1947-50.
31. Biskobing D M, Fan D. Acid pH increases carbonic anhydrase II and calcitonin receptor mRNA expression in mature osteoclasts. Calcif Tissue Int. 2000 August; 67(2): 178-83.
32. Brage M, Abrahamson M, Lindstrom V, Grubb A, Lerner U H. Different cysteine proteinases involved in bone resorption and osteoclast formation. Calcif Tissue Int. 2005 June; 76(6):439-47. Epub 2005 May 19.

What is claimed is:

1. A method of impairing osteoclast differentiation in a mammal in need thereof, the method comprising administering an antibody or antigen binding fragment which specifically binds to human Siglec-15 (SEQ ID NO.:2) or murine Siglec-15 (SEQ ID NO.:108) to said mammal.

2. The method of claim 1, wherein the antibody or antigen binding fragment impairs an osteoclast differentiation activity of human Siglec-15 or murine Siglec 15.

3. The method of claim 2, wherein the osteoclast differentiation activity is characterized by differentiation of osteoclast precursor cells into differentiated osteoclasts.

4. The method of claim 2, wherein the antibody is a polyclonal antibody.

5. The method of claim 2, wherein the antibody or antigen binding fragment is a monoclonal antibody or an antigen binding fragment thereof.

6. The method of claim 5, wherein the monoclonal antibody or antigen binding fragment is produced from an isolated mammalian cell.

7. The method of claim 6, wherein the isolated mammalian cell is a human cell.

8. The method of claim 6, wherein the antibody or antigen binding fragment comprises a constant region of a human antibody or a fragment thereof.

9. The method of claim 8, wherein the antibody or antigen binding fragment comprises a framework region of a human antibody.

10. The method of claim 2, wherein the antibody or antigen binding fragment is a FV, a Fab, a Fab' or a (Fab')$_2$.

11. The method of claim 3, wherein the osteoclast precursor cells are human osteoclast precursor cells.

12. The method of claim 11, wherein the human osteoclast precursor cells are primary human osteoclast precursor cells.

13. The method of claim 2, wherein the antibody or antigen binding fragment binds to human Siglec-15 with a greater affinity than to murine Siglec-15.

14. The method of claim 2, wherein the antibody or antigen binding fragment binds to human Siglec-15 and does not bind murine Siglec-15.

15. A method for inhibiting bone resorption comprising administering to a subject in need thereof, an antibody or antigen binding fragment which specifically binds to human Siglec-15 (SEQ ID NO.:2) or murine Siglec-15 (SEQ ID NO.:108).

16. The method of claim 15, wherein the antibody or antigen binding fragment impairs an activity of human Siglec-15 or murine Siglec-15 in osteoclast precursor cells or in osteoclasts.

17. The method of claim 16, wherein the activity is osteoclastogenesis.

18. The method of claim 15, wherein the antibody or antigen binding fragment inhibits osteoclast differentiation.

19. The method of claim 15, wherein the antibody or antigen binding fragment is administered in combination with a drug or an hormone.

20. The method of claim 19, wherein the drug is an antiresorptive drug or a drug increasing bone mineral density.

21. The method of claim 15, wherein the subject in need thereof, suffers from a bone remodelling disorder.

22. The method of claim 21, wherein the bone remodelling disorder is associated with a decrease in bone mass.

23. The method of claim 21, wherein the bone remodelling disorder is selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets, fibrogenesis imperfecta ossium, osteosclerotic disorders, pycnodysostosis, and damage caused by macrophage-mediated inflammatory processes.

24. The method of claim 15, wherein the antibody or antigen binding fragment binds to human Siglec-15 with a greater affinity than to murine Siglec-15.

25. The method of claim 15, wherein the antibody or antigen binding fragment binds to human Siglec-15 and does not bind murine Siglec-15.

* * * * *

SEQUENCE LISTING

```
<160> NUMBER OF SEQ ID NOS: 108

<210> SEQ ID NO 1
<211> LENGTH: 987
<212> TYPE: DNA
<213> ORGANISM: Homo sapiens
<300> PUBLICATION INFORMATION:
<301> AUTHORS: Ota et al.
<302> TITLE: Complete sequencing and characterization of 21,243
      full-length
<303> JOURNAL: Nat Genet.
<304> VOLUME: 36
<306> PAGES: 40-45
<307> DATE: 2004
<313> RELEVANT RESIDUES IN SEQ ID NO: (1)..(987)
```

```
<300> PUBLICATION INFORMATION:
<308> DATABASE ACCESSION NUMBER: NM_213602
<309> DATABASE ENTRY DATE: 2009-03-25
<313> RELEVANT RESIDUES IN SEQ ID NO: (1)..(987)

<400> SEQUENCE: 1
atggaaaagt ccatctggct gctggcctgc ttggcgtggg ttctcccgac aggctcattt      60
gtgagaacta aaatagatac tacggagaac ttgctcaaca cagaggtgca cagctcgcca     120
gcgcagcgct ggtccatgca ggtgccaccc gaggtgagcg cggaggcagg cgacgcggca     180
gtgctgccct gcaccttcac gcacccgcac cgccactacg acgggccgct gacggccatc     240
tggcgcgcgg gcgagcccta tgcgggcccg caggtgttcc gctgcgctgc ggcgcggggc     300
agcgagctct gccagacggc gctgagcctg cacggccgct tccggctgct gggcaacccg     360
cgccgcaacg acctctcgct gcgcgtcgag cgcctcgccc tggctgacga ccgccgctac     420
ttctgccgcg tcgagttcgc cggcgacgtc catgaccgct acgagagccg ccacggcgtc     480
cggctgcacg tgacagccgc gccgcggatc gtcaacatct cggtgctgcc cagtccggct     540
cacgccttcc gcgcgctctg cactgccgaa ggggagccgc cgcccgccct cgcctggtcc     600
ggcccggccc tgggcaacag cttggcagcc gtgcggagcc cgcgtgaggg tcacggccac     660
ctagtgaccg ccgaactgcc cgcactgacc catgacggcc gctacacgtg tacggccgcc     720
aacagcctgg gccgctccga ggccagcgtc tacctgttcc gcttccatgg cgccagcggg     780
gcctcgacgg tcgccctcct gctcggcgct ctcggcttca aggcgctgct gctgctcggg     840
gtcctggccg ccgcgctgc ccgccgccgc ccagagcatc tggacacccc ggacacccca     900
ccacggtccc aggcccagga gtccaattat gaaaatttga gccagatgaa ccccggagc      960 ccaccagcca ccatgtgctc accgtga                                         987

<210> SEQ ID NO 2
<211> LENGTH: 328
<212> TYPE: PRT
<213> ORGANISM: Homo sapiens
<300> PUBLICATION INFORMATION:
<301> AUTHORS: Angata,T.
<302> TITLE: Siglec-15: an immune system Siglec conserved throughout
      vertebrate
<303> JOURNAL: Glycobiology
<304> VOLUME: 17
<305> ISSUE: 8
<306> PAGES: 838-846
<307> DATE: 2007-05-04
<313> RELEVANT RESIDUES IN SEQ ID NO: (1)..(328)

<400> SEQUENCE: 2

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala
                85                  90                  95

Ala Ala Arg Gly Ser Glu Leu Cys Gln Thr Ala Leu Ser Leu His Gly
            100                 105                 110
```

| | | | | | | | | | | | | |
|---|---|---|---|---|---|---|---|---|---|---|---|---|
|Arg|Phe|Arg|Leu|Leu|Gly|Asn|Pro|Arg|Arg|Asn|Asp|Leu|Ser|Leu|Arg|
| |115| | | |120| | | |125| | | |

Val Glu Arg Leu Ala Leu Ala Asp Asp Arg Tyr Phe Cys Arg Val
    130                 135                 140

Glu Phe Ala Gly Asp Val His Asp Arg Tyr Glu Ser Arg His Gly Val
145                 150                 155                 160

Arg Leu His Val Thr Ala Ala Pro Arg Ile Val Asn Ile Ser Val Leu
            165                 170                 175

Pro Ser Pro Ala His Ala Phe Arg Ala Leu Cys Thr Ala Glu Gly Glu
            180                 185                 190

Pro Pro Pro Ala Leu Ala Trp Ser Gly Pro Ala Leu Gly Asn Ser Leu
            195                 200                 205

Ala Ala Val Arg Ser Pro Arg Glu Gly His Gly His Leu Val Thr Ala
210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
            245                 250                 255

Gly Ala Ser Gly Ala Ser Thr Val Ala Leu Leu Gly Ala Leu Gly
            260                 265                 270

Phe Lys Ala Leu Leu Leu Gly Val Leu Ala Ala Arg Ala Ala Arg
            275                 280                 285

Arg Arg Pro Glu His Leu Asp Thr Pro Asp Thr Pro Pro Arg Ser Gln
290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
            325

<210> SEQ ID NO 3
<211> LENGTH: 1029
<212> TYPE: DNA
<213> ORGANISM: Mus musculus

<400> SEQUENCE: 3

```
atggagggt ccctccaact cctggcctgc ttggcctgtg tgctccagat gggatccctt    60
gtgaaaacta aagagacgc ttcgggggat ctgctcaaca cagaggcgca cagtgccccg   120
gcgcagcgct ggtccatgca ggtgcccgcg gaggtgaacg cggaggctgg cgacgcggcg   180
gtgctgccct gcaccttcac gcacccgcac cgccactacg acgggccgct gacggccatc   240
tggcgctcgg gcgagccgta cgcgggcccg caggtgttcc gctgcaccgc ggcgccgggc   300
agcgagctgt gccagacggc gctgagcctg cacggccgct tccgcctgct gggcaacccg   360
cgccgcaacg acctgtccct gcgcgtcgag cgcctcgccc tggcggacag cggccgctac   420
ttctgccgcg tggagttcac cggcgacgcc acgatcgct atgagagtcg ccatggggtc   480
cgtctgcgcg tgactgcagc tgcgccgcgg atcgtcaaca tctcggtgct gccgggcccc   540
gcgcacgcct tccgcgcgct ctgcaccgcc gaggggggagc cccgcccgc cctcgcctgg   600
tcgggtcccg ccccaggcaa cagctccgct gccctgcagg gccagggtca cggctaccag   660
gtgaccgccg agttgcccgc gctgacccgc gacggccgct acacgtgcac ggcggccaat   720
agcctgggcc gcgccgaggc cagcgtctac ctgttccgct ccacggcgc cccggaacc    780
tcgaccctag cgctcctgct gggcgcgctg ggcctcaagg ccttgctgct gcttggcatt   840
ctgggagcgc gtgccacccg cgccgactaa gatcacctgg tccccagga cacccctcca   900
```

```
cggtctcagg ctcaggagtc caattatgaa aatttgagcc agatgagtcc tccaggccac    960
cagctgccac gtgtttgctg tgaggaactc ctcagccatc accatctagt cattcaccat   1020
gagaaataa                                                            1029
```

<210> SEQ ID NO 4
<211> LENGTH: 342
<212> TYPE: PRT
<213> ORGANISM: Mus musculus

<400> SEQUENCE: 4

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125

Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Ala Pro Arg Ile Val Asn Ile Ser Val
                165                 170                 175

Leu Pro Gly Pro Ala His Ala Phe Arg Ala Leu Cys Thr Ala Glu Gly
            180                 185                 190

Glu Pro Pro Pro Ala Leu Ala Trp Ser Gly Pro Ala Pro Gly Asn Ser
        195                 200                 205

Ser Ala Ala Leu Gln Gly Gln Gly His Gly Tyr Gln Val Thr Ala Glu
    210                 215                 220

Leu Pro Ala Leu Thr Arg Asp Gly Arg Tyr Thr Cys Thr Ala Ala Asn
225                 230                 235                 240

Ser Leu Gly Arg Ala Glu Ala Ser Val Tyr Leu Phe Arg Phe His Gly
                245                 250                 255

Ala Pro Gly Thr Ser Thr Leu Ala Leu Leu Leu Gly Ala Leu Gly Leu
            260                 265                 270

Lys Ala Leu Leu Leu Leu Gly Ile Leu Gly Ala Arg Ala Thr Arg Arg
        275                 280                 285

Arg Leu Asp His Leu Val Pro Gln Asp Thr Pro Pro Arg Ser Gln Ala
    290                 295                 300

Gln Glu Ser Asn Tyr Glu Asn Leu Ser Gln Met Ser Pro Pro Gly His
305                 310                 315                 320

Gln Leu Pro Arg Val Cys Cys Glu Glu Leu Ser His His Leu
                325                 330                 335

Val Ile His His Glu Lys
            340
```

<210> SEQ ID NO 5
<211> LENGTH: 19
<212> TYPE: DNA
<213> ORGANISM: Artificial Sequence
<220> FEATURE:
<223> OTHER INFORMATION: shRNA sequence

<400> SEQUENCE: 5

| | |
|---|---:|
| acacgtgcac ggcggccaa | 19 |

<210> SEQ ID NO 6
<211> LENGTH: 2996
<212> TYPE: DNA
<213> ORGANISM: Artificial Sequence
<220> FEATURE:
<223> OTHER INFORMATION: plasmid vectors - p14

<400> SEQUENCE: 6

| | |
|---|---:|
| ttttcccagt cacgacgttg taaaacgacg gccagtgaat tctaatacga ctcactatag | 60 |
| ggagacgaga gcacctggat aggttcgcgt ggcgcgccgc atgcgtcgac ggatcctgag | 120 |
| aacttcaggc tcctgggcaa cgtgctggtt attgtgctgt ctcatcattt tggcaaagaa | 180 |
| ttcactcctc aggtgcaggc tgcctatcag aaggtggtgg ctggtgtggc caatgccctg | 240 |
| gctcacaaat accactgaga tcttttttccc tctgccaaaa attatgggga catcatgaag | 300 |
| ccccttgagc atctgacttc tggctaataa aggaaattta ttttcattgc aaaaaaaaaa | 360 |
| agcggccgct aactgttggt gcaggcgctc ggaccgctag cttggcgtaa tcatggtcat | 420 |
| agctgtttcc tgtgtgaaat tgttatccgc tcacaattcc acacaacata cgagccggaa | 480 |
| gcataaagtg taaagcctgg ggtgcctaat gagtgagcta actcacatta attgcgttgc | 540 |
| gctcactgcc cgctttccag tcgggaaacc tgtcgtgcca gctgcattaa tgaatcggcc | 600 |
| aacgcgcggg gagaggcggt ttgcgtattg ggcgctcttc cgcttcctcg ctcactgact | 660 |
| cgctgcgctc ggtcgttcgg ctgcggcgag cggtatcagc tcactcaaag gcggtaatac | 720 |
| ggttatccac agaatcaggg gataacgcag gaaagaacat gtgagcaaaa ggccagcaaa | 780 |
| aggccaggaa ccgtaaaaag gccgcgttgc tggcgttttt ccataggctc cgcccccctg | 840 |
| acgagcatca caaaaatcga cgctcaagtc agaggtggcg aaacccgaca ggactataaa | 900 |
| gataccaggc gtttccccct ggaagctccc tcgtgcgctc tcctgttccg accctgccgc | 960 |
| ttaccggata cctgtccgcc tttctccctt cgggaagcgt ggcgctttct caatgctcac | 1020 |
| gctgtaggta tctcagttcg gtgtaggtcg ttcgctccaa gctgggctgt gtgcacgaac | 1080 |
| cccccgttca gcccgaccgc tgcgccttat ccggtaacta tcgtcttgag tccaacccgg | 1140 |
| taagacacga cttatcgcca ctggcagcag ccactggtaa caggattagc agagcgaggt | 1200 |
| atgtaggcgg tgctacagag ttcttgaagt ggtggcctaa ctacggctac actagaagga | 1260 |
| cagtatttgg tatctgcgct ctgctgaagc cagttacctt cggaaaaaga gttggtagct | 1320 |
| cttgatccgg caaacaaacc accgctggta gcggtggttt ttttgtttgc aagcagcaga | 1380 |
| ttacgcgcag aaaaaaagga tctcaagaag atcctttgat cttttctacg ggtctgacg | 1440 |
| ctcagtggaa cgaaaactca cgttaaggga ttttggtcat gagattatca aaaaggatct | 1500 |
| tcacctagat ccttttaaat taaaaatgaa gttttaaatc aatctaaagt atatatgagt | 1560 |
| aaacttggtc tgacagttac caatgcttaa tcagtgaggc acctatctca gcgatctgtc | 1620 |
| tatttcgttc atccatagtt gcctgactcc ccgtcgtgta gataactacg atacgggagg | 1680 |
| gcttaccatc tggccccagt gctgcaatga taccgcgaga cccacgctca ccggctccag | 1740 |

```
atttatcagc aataaaccag ccagccggaa gggccgagcg cagaagtggt cctgcaactt    1800
tatccgcctc catccagtct attaattgtt gccgggaagc tagagtaagt agttcgccag    1860
ttaatagttt gcgcaacgtt gttgccattg ctacaggcat cgtggtgtca cgctcgtcgt    1920
ttggtatggc ttcattcagc tccggttccc aacgatcaag gcgagttaca tgatccccca    1980
tgttgtgcaa aaaagcggtt agctccttcg gtcctccgat cgttgtcaga gtaagttgg     2040 ccgcagtgtt atcactcatg gttatggcag cactgcataa ttctcttact gtcatgccat    2100
ccgtaagatg cttttctgtg actggtgagt actcaaccaa gtcattctga aatagtgta    2160 tgcggcgacc gagttgctct tgcccggcgt caatacggga taataccgcg ccacatagca    2220
gaactttaaa agtgctcatc attggaaaac gttcttcggg gcgaaaactc tcaaggatct    2280
taccgctgtt gagatccagt tcgatgtaac ccactcgtgc acccaactga tcttcagcat    2340
cttttacttt caccagcgtt tctgggtgag caaaaacagg aaggcaaaat gccgcaaaaa    2400
agggaataag ggcgacacgg aaatgttgaa tactcatact cttcctttt caatattatt    2460 gaagcattta tcagggttat tgtctcatga gcggatacat atttgaatgt atttagaaaa    2520
ataaacaaat aggggttccg cgcacatttc cccgaaaagt gccacctgac gtctaagaaa    2580
ccattattat catgacatta acctataaaa ataggcgtat cacgaggccc tttcgtctcg    2640
cgcgtttcgg tgatgacggt gaaaacctct gacacatgca gctcccggag acggtcacag    2700
cttgtctgta agcggatgcc gggagcagac aagcccgtca gggcgcgtca gcgggtgttg    2760
gcgggtgtcg ggctggctt aactatgcgg catcagagca gattgtactg agagtgcacc    2820
atatgcggtg tgaaataccg cacagatgcg taaggagaaa ataccgcatc aggcgccatt    2880
cgccattcag gctgcgcaac tgttgggaag ggcgatcggt gcgggcctct tcgctattac    2940
gccagctggc gaaggggga tgtgctgcaa ggcgattaag ttgggtaacg ccaggg         2996
```

<210> SEQ ID NO 7
<211> LENGTH: 2992
<212> TYPE: DNA
<213> ORGANISM: Artificial Sequence
<220> FEATURE:
<223> OTHER INFORMATION: plasmid vector p17+

<400> SEQUENCE: 7

```
ttttcccagt cacgacgttg taaaacgacg gccagtgaat tcgagctcac atacgattta      60
ggtgacacta taggcctgca ccaacagtta acacggcgcg ccgcatgcgt cgacggatcc     120
tgagaacttc aggctcctgg gcaacgtgct ggttattgtg ctgtctcatc attttggcaa    180
agaattcact cctcaggtgc aggctgccta tcagaaggtg gtggctggtg tggccaatgc    240
cctggctcac aaataccact gagatctttt tccctctgcc aaaaattatg gggacatcat    300
gaagcccctt gagcatctga cttctggcta taaaggaaa tttattttca ttgcaaaaaa    360
aaaaagcggc cgctagagtc ggccgcagcg gccgagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgctc    540
actgcccgct ttccagtcgg gaaacctgtc gtgccagctg cattaatgaa tcggccaacg    600
cgcggggaga ggcggtttgc gtattggcg ctcttccgct tcctcgctca ctgactcgct    660
gcgctcggtc gttcggctgc ggcgagcggt atcagctcac tcaaaggcgg taatacggtt    720
atccacagaa tcaggggata acgcaggaaa gaacatgtga gcaaaaggcc agcaaaaggc    780
caggaaccgt aaaaaggccg cgttgctggc gttttccat aggctccgcc cccctgacga    840
```

```
gcatcacaaa aatcgacgct caagtcagag gtggcgaaac ccgacaggac tataaagata      900
ccaggcgttt cccctggaa gctccctcgt gcgctctcct gttccgaccc tgccgcttac      960
cggatacctg tccgcctttc tcccttcggg aagcgtggcg ctttctcaaa gctcacgctg     1020
taggtatctc agttcggtgt aggtcgttcg ctccaagctg gctgtgtgc acgaaccccc      1080 cgttcagccc gaccgctgcg ccttatccgg taactatcgt cttgagtcca acccggtaag     1140
acacgactta tcgccactgg cagcagccac tggtaacagg attagcagag cgaggtatgt     1200
aggcggtgct acagagttct tgaagtggtg gcctaactac ggctacacta agaacagt       1260 atttggtatc tgcgctctgc tgaagccagt taccttcgga aaagagttg gtagctcttg      1320 atccggcaaa caaaccaccg ctggtagcgg tggttttttt gtttgcaagc agcagattac     1380
gcgcagaaaa aaaggatctc aagaagatcc tttgatcttt tctacggggt ctgacgctca     1440
gtggaacgaa aactcacgtt aagggatttt ggtcatgaga ttatcaaaaa ggatcttcac     1500
ctagatcctt ttaaattaaa aatgaagttt taaatcaatc taaagtatat atgagtaaac     1560
ttggtctgac agttaccaat gcttaatcag tgaggcacct atctcagcga tctgtctatt     1620
tcgttcatcc atagttgcct gactccccgt cgtgtagata actacgatac gggagggctt     1680
accatctggc cccagtgctg caatgatacc gcgagaccca cgctcaccgg ctccagattt     1740
atcagcaata aaccagccag ccggaagggc cgagcgcaga gtggtcctg caactttatc      1800 cgcctccatc cagtctatta attgttgccg ggaagctaga gtaagtagtt cgccagttaa     1860 tagtttcgc aacgttgttg ccattgctac aggcatcgtg gtgtcacgct cgtcgtttgg      1920
tatggcttca ttcagctccg gttcccaacg atcaaggcga gttacatgat ccccatgtt     1980 gtgcaaaaaa gcggttagct ccttcggtcc tccgatcgtt gtcagaagta agttggccgc     2040
agtgttatca ctcatggtta tggcagcact gcataattct cttactgtca tgccatccgt     2100
aagatgcttt tctgtgactg gtgagtactc aaccaagtca ttctgagaat agtgtatgcg     2160
gcgaccgagt tgctcttgcc cggcgtcaat acgggataat accgcgccac atagcagaac     2220
tttaaaagtg ctcatcattg gaaaacgttc ttcggggcga aaactctcaa ggatcttacc     2280
gctgttgaga tccagttcga tgtaacccac tcgtgcaccc aactgatctt cagcatcttt     2340
tactttcacc agcgtttctg ggtgagcaaa aacaggaagg caaaatgccg caaaaaaggg     2400
aataagggcg acacggaaat gttgaatact catactcttc ctttttcaat attattgaag     2460
catttatcag ggttattgtc tcatgagcgg atacatattt gaatgtattt agaaaaataa     2520
acaaataggg gttccgcgca catttccccg aaaagtgcca cctgacgtct aagaaaccat     2580
tattatcatg acattaacct ataaaaatag gcgtatcacg aggcccttc gtctcgcgcg     2640 tttcggtgat gacggtgaaa acctctgaca catgcagctc ccggagacgg tcacagcttg     2700
tctgtaagcg gatgccggga gcagacaagc ccgtcagggc gcgtcagcgg gtgttggcgg     2760
gtgtcggggc tggcttaact atgcggcatc agagcagatt gtactgagag tgcaccatat     2820
gcggtgtgaa ataccgcaca gatgcgtaag agaaaatac cgcatcaggc gccattcgcc      2880
attcaggctg cgcaactgtt gggaagggcg atcggtgcgg gcctcttcgc tattacgcca     2940
gctggcgaaa gggggatgtg ctgcaaggcg attaagttgg gtaacgccag gg             2992
```

<210> SEQ ID NO 8
<211> LENGTH: 48
<212> TYPE: DNA
<213> ORGANISM: Artificial Sequence
<220> FEATURE:
<223> OTHER INFORMATION: primer OGS 77 for p14

```
<400> SEQUENCE: 8
aattctaata cgactcacta tagggagacg agagcacctg gataggtt          48

<210> SEQ ID NO 9
<211> LENGTH: 20
<212> TYPE: DNA
<213> ORGANISM: Artificial Sequence
<220> FEATURE:
<223> OTHER INFORMATION: primer OGS 302 for p17+

<400> SEQUENCE: 9
gcctgcacca acagttaaca                                         20

<210> SEQ ID NO 10
<211> LENGTH: 2757
<212> TYPE: DNA
<213> ORGANISM: Artificial Sequence
<220> FEATURE:
<223> OTHER INFORMATION: pCATRMAN plasmid vector

<400> SEQUENCE: 10
ttttcccagt cacgacgttg taaaacgacg gccagtgaat tctaatacga ctcactatag    60
ggagatggag aaaaaaatca ctggacgcgt ggcgcgccat taattaatgc ggccgctagc   120
tcgagtgata taagcggat gaatggctgc aggcatgcaa gcttggcgta atcatggtca    180
tagctgtttc ctgtgtgaaa ttgttatccg ctcacaattc cacacaacat acgagccgga   240
agcataaagt gtaaagcctg gggtgcctaa tgagtgagct aactcacatt aattgcgttg   300
cgctcactgc ccgctttcca gtcgggaaac ctgtcgtgcc agctgcatta atgaatcggc   360
caacgcgcgg ggagaggcgg tttgcgtatt gggcgctctt ccgcttcctc gctcactgac   420
tcgctgcgct cggtcgttcg gctgcggcga gcggtatcag ctcactcaaa ggcggtaata   480
cggttatcca cagaatcagg ggataacgca ggaaagaaca tgtgagcaaa aggccagcaa   540
aaggccagga accgtaaaaa ggccgcgttg ctggcgtttt tccataggct ccgcccccct   600
gacgagcatc acaaaaatcg acgctcaagt cagaggtggc gaaacccgac aggactataa   660
agataccagg cgtttccccc tggaagctcc ctcgtgcgct ctcctgttcc gaccctgccg   720
cttaccggat acctgtccgc ctttctccct tcgggaagcg tggcgctttc tcaatgctca   780
cgctgtaggt atctcagttc ggtgtaggtc gttcgctcca agctgggctg tgtgcacgaa   840
ccccccgttc agcccgaccg ctgcgcctta tccggtaact atcgtcttga gtccaacccg   900
gtaagacacg acttatcgcc actggcagca gccactggta acaggattag cagagcgagg   960
tatgtaggcg gtgctacaga gttcttgaag tggtggccta actacggcta cactagaagg  1020
acagtatttg gtatctgcgc tctgctgaag ccagttacct tcggaaaaag agttggtagc  1080
tcttgatccg gcaaacaaac caccgctggt agcggtggtt ttttgtttg caagcagcag    1140 attacgcgca gaaaaaaagg atctcaagaa gatcctttga tcttttctac ggggtctgac  1200
gctcagtgga acgaaaactc acgttaaggg attttggtca tgagattatc aaaaaggatc  1260
ttcacctaga tccttttaaa ttaaaaatga agttttaaat caatctaaag tatatatgag  1320
taaacttggt ctgacagtta ccaatgctta atcagtgagg cacctatctc agcgatctgt  1380
ctatttcgtt catccatagt tgcctgactc cccgtcgtgt agataactac gatacgggag  1440
ggcttaccat ctggccccag tgctgcaatg ataccgcgag acccacgctc accggctcca  1500
gatttatcag caataaacca gccagccgga agggccgagc gcagaagtgg tcctgcaact  1560
ttatccgcct ccatccagtc tattaattgt tgccgggaag ctagagtaag tagttcgcca  1620
```

```
gttaatagtt tgcgcaacgt tgttgccatt gctacaggca tcgtggtgtc acgctcgtcg    1680
tttggtatgg cttcattcag ctccggttcc caacgatcaa ggcgagttac atgatccccc    1740
atgttgtgca aaaagcggt tagctccttc ggtcctccga tcgttgtcag aagtaagttg     1800
gccgcagtgt tatcactcat ggttatggca gcactgcata attctcttac tgtcatgcca    1860
tccgtaagat gcttttctgt gactggtgag tactcaacca agtcattctg agaatagtgt    1920
atgcggcgac cgagttgctc ttgcccggcg tcaatacggg ataataccgc gccacatagc    1980
agaactttaa aagtgctcat cattggaaaa cgttcttcgg ggcgaaaact ctcaaggatc    2040
ttaccgctgt tgagatccag ttcgatgtaa cccactcgtg cacccaactg atcttcagca    2100
tcttttactt tcaccagcgt ttctgggtga gcaaaaacag gaaggcaaaa tgccgcaaaa    2160
aagggaataa gggcgacacg gaaatgttga atactcatac tcttcctttt tcaatattat    2220
tgaagcattt atcagggtta ttgtctcatg agcggataca tatttgaatg tatttagaaa    2280
aataaacaaa taggggttcc gcgcacattt ccccgaaaag tgccacctga cgtctaagaa    2340
accattatta tcatgacatt aacctataaa aataggcgta tcacgaggcc ctttcgtctc    2400
gcgcgtttcg gtgatgacgg tgaaaacctc tgacacatgc agctcccgga cgggtcaca     2460 gcttgtctgt aagcggatgc cgggagcaga caagcccgtc agggcgcgtc agcgggtgtt    2520
ggcgggtgtc ggggctggct taactatgcg gcatcagagc agattgtact gagagtgcac    2580
catatgcggt gtgaaatacc gcacagatgc gtaaggagaa ataccgcat caggcgccat     2640 tcgccattca ggctgcgcaa ctgttgggaa gggcgatcgg tgcgggcctc ttcgctatta    2700
cgccagctgg cgaaaggggg atgtgctgca aggcgattaa gttgggtaac gccaggg       2757

<210> SEQ ID NO 11
<211> LENGTH: 2995
<212> TYPE: DNA
<213> ORGANISM: Artificial Sequence
<220> FEATURE:
<223> OTHER INFORMATION: p20 plasmid vector

<400> SEQUENCE: 11
ttttcccagt cacgacgttg taaaacgacg gccagtgaat tcaattaacc ctcactaaag      60
ggagacttgt tccaaatgtg ttaggcgcgc cgcatgcgtc gacggatcct gagaacttca    120
ggctcctggg caacgtgctg gttattgtgc tgtctcatca ttttggcaaa gaattcactc    180
ctcaggtgca ggctgcctat cagaaggtgg tggctggtgt ggccaatgcc ctggctcaca    240 ataccactg agatcttttt ccctctgcca aaaattatgg ggacatcatg aagccccttg     300
agcatctgac ttctggctaa taaggaaat ttatttcat tgcaaaaaaa aaaagcggcc      360
gctcttctat agtgtcacct aaatggccca gcggccgagc ttggcgtaat catggtcata    420
gctgtttcct gtgtgaaatt gttatccgct cacaattcca cacaacatac gagccggaag    480
cataaagtgt aaagcctggg gtgcctaatg agtgagctaa ctcacattaa ttgcgttgcg    540
ctcactgccc gctttccagt cgggaaacct gtcgtgccag ctgcattaat gaatcggcca    600
acgcgcgggg agaggcggtt tgcgtattgg gcgctcttcc gcttcctcgc tcactgactc    660
gctgcgctcg gtcgttcggc tgcggcgagc ggtatcagct cactcaaagg cggtaatacg    720
gttatccaca gaatcagggg ataacgcagg aaagaacatg tgagcaaaag gccagcaaaa    780
ggccaggaac cgtaaaaagg ccgcgttgct ggcgtttttc cataggctcc gcccccctga    840
cgagcatcac aaaaatcgac gctcaagtca gaggtggcga aacccgacag gactataaag    900
ataccaggcg tttccccctg gaagctccct cgtgcgctct cctgttccga ccctgccgct    960
```

| | |
|---|---|
| taccggatac ctgtccgcct ttctcccttc gggaagcgtg gcgctttctc aaagctcacg | 1020 |
| ctgtaggtat ctcagttcgg tgtaggtcgt tcgctccaag ctgggctgtg tgcacgaacc | 1080 |
| ccccgttcag cccgaccgct gcgccttatc cggtaactat cgtcttgagt ccaacccggt | 1140 |
| aagacacgac ttatcgccac tggcagcagc cactggtaac aggattagca gagcgaggta | 1200 |
| tgtaggcggt gctacagagt tcttgaagtg gtggcctaac tacggctaca ctagaagaac | 1260 |
| agtatttggt atctgcgctc tgctgaagcc agttaccttc ggaaaaagag ttggtagctc | 1320 |
| ttgatccggc aaacaaacca ccgctggtag cggtggtttt tttgtttgca agcagcagat | 1380 |
| tacgcgcaga aaaaaaggat ctcaagaaga tcctttgatc ttttctacgg ggtctgacgc | 1440 |
| tcagtggaac gaaaactcac gttaagggat tttggtcatg agattatcaa aaaggatctt | 1500 |
| cacctagatc cttttaaatt aaaaatgaag ttttaaatca atctaaagta tatatgagta | 1560 |
| aacttggtct gacagttacc aatgcttaat cagtgaggca cctatctcag cgatctgtct | 1620 |
| atttcgttca tccatagttg cctgactccc cgtcgtgtag ataactacga tacgggaggg | 1680 |
| cttaccatct ggccccagtg ctgcaatgat accgcgagac ccacgctcac cggctccaga | 1740 |
| tttatcagca ataaaccagc cagccggaag ggccgagcgc agaagtggtc ctgcaacttt | 1800 |
| atccgcctcc atccagtcta ttaattgttg ccgggaagct agagtaagta gttcgccagt | 1860 |
| taatagtttg cgcaacgttg ttgccattgc tacaggcatc gtggtgtcac gctcgtcgtt | 1920 |
| tggtatggct tcattcagct ccggttccca acgatcaagg cgagttacat gatcccccat | 1980 |
| gttgtgcaaa aaagcggtta gctccttcgg tcctccgatc gttgtcagaa gtaagttggc | 2040 |
| cgcagtgtta tcactcatgg ttatggcagc actgcataat tctcttactg tcatgccatc | 2100 |
| cgtaagatgc ttttctgtga ctggtgagta ctcaaccaag tcattctgag aatagtgtat | 2160 |
| gcggcgaccg agttgctctt gcccggcgtc aatacgggat aataccgcgc cacatagcag | 2220 |
| aactttaaaa gtgctcatca ttggaaaacg ttcttcgggg cgaaaactct caaggatctt | 2280 |
| accgctgttg agatccagtt cgatgtaacc cactcgtgca cccaactgat cttcagcatc | 2340 |
| ttttactttc accagcgttt ctgggtgagc aaaaacagga aggcaaaatg ccgcaaaaaa | 2400 |
| gggaataagg gcgacacgga aatgttgaat actcatactc ttcctttttc aatattattg | 2460 |
| aagcatttat cagggttatt gtctcatgag cggatacata tttgaatgta tttagaaaaa | 2520 |
| taaacaaata ggggttccgc gcacatttcc ccgaaaagtg ccacctgacg tctaagaaac | 2580 |
| cattattatc atgacattaa cctataaaaa taggcgtatc acgaggccct ttcgtctcgc | 2640 |
| gcgtttcggt gatgacggtg aaaacctctg acacatgcag ctcccggaga cggtcacagc | 2700 |
| ttgtctgtaa gcggatgccg ggagcagaca agcccgtcag ggcgcgtcag cgggtgttgg | 2760 |
| cgggtgtcgg gctggctta actatgcggc atcagagcag attgtactga gagtgcacca | 2820 |
| tatgcggtgt gaaataccgc acagatgcgt aaggagaaaa taccgcatca ggcgccattc | 2880 |
| gccattcagg ctgcgcaact gttgggaagg gcgatcggtg cgggcctctt cgctattacg | 2940 |
| ccagctggcg aaagggggat gtgctgcaag gcgattaagt tgggtaacgc caggg | 2995 |

<210> SEQ ID NO 12
<211> LENGTH: 19
<212> TYPE: DNA
<213> ORGANISM: Artificial Sequence
<220> FEATURE:
<223> OTHER INFORMATION: shRNA sequence

<400> SEQUENCE: 12
caggcccagg agtccaatt                                              19

```
<210> SEQ ID NO 13
<211> LENGTH: 19
<212> TYPE: DNA
<213> ORGANISM: Artificial Sequence
<220> FEATURE:
<223> OTHER INFORMATION: shRNA sequence

<400> SEQUENCE: 13
gcgccgcgga tcgtcaaca                                                  19

<210> SEQ ID NO 14
<211> LENGTH: 19
<212> TYPE: DNA
<213> ORGANISM: Artificial Sequence
<220> FEATURE:
<223> OTHER INFORMATION: shRNA sequence

<400> SEQUENCE: 14
acacgtgcac ggcggccaa                                                  19

<210> SEQ ID NO 15
<211> LENGTH: 4002
<212> TYPE: DNA
<213> ORGANISM: Artificial Sequence
<220> FEATURE:
<223> OTHER INFORMATION: expression vector pd2

<400> SEQUENCE: 15
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta caactccgcc ccattgacgc aaatgggcg gtaggcgtgt    540 acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg ggccgcgact ctagatcata atcagccata ccacatttgt agaggtttta    720
cttgctttaa aaaacctccc acacctcccc ctgaacctga acataaaat gaatgcaatt    780 gttgttgtta acttgtttat tgcagcttat aatggttaca ataaagcaa tagcatcaca    840 aatttcacaa ataaagcatt ttttcactg cattctagtt gtggtttgtc caaactcatc    900
aatgtatctt aaggcgtaaa ttgtaagcgt taatattttg ttaaaattcg cgttaaattt    960
ttgttaaatc agctcatttt ttaaccaata ggccgaaatc ggcaaaatcc cttataaatc   1020
aaaagaatag accgagatag ggttgagtgt tgttccagtt tggaacaaga gtccactatt   1080
aaagaacgtg gactccaacg tcaaagggcg aaaaaccgtc tatcagggcg atggcccact   1140
acgtgaacca tcaccctaat caagtttttt gggtcgagg tgccgtaaag cactaaatcg   1200
gaaccctaaa gggagccccc gatttagagc ttgacgggga agccggcga acgtggcgag   1260 aaaggaaggg aagaaagcga aaggagcggg cgctagggcg ctggcaagtg tagcggtcac   1320
gctgcgcgta accaccacac ccgccgcgct taatgcgccg ctacagggcg cgtcaggtgg   1380
```

```
cacttttcgg ggaaatgtgc gcggaacccc tatttgttta tttttctaaa tacattcaaa    1440
tatgtatccg ctcatgagac aataaccctg ataaatgctt caataatatt gaaaaaggaa    1500
gagtcctgag gcggaaagaa ccagctgtgg aatgtgtgtc agttagggtg tggaaagtcc    1560
ccaggctccc cagcaggcag aagtatgcaa agcatgcatc tcaattagtc agcaaccagg    1620
tgtggaaagt ccccaggctc cccagcaggc agaagtatgc aaagcatgca tctcaattag    1680
tcagcaacca tagtcccgcc cctaactccg cccatcccgc ccctaactcc gcccagttcc    1740
gcccattctc cgccccatgg ctgactaatt ttttttattt atgcagaggc cgaggccgcc    1800
tcggcctctg agctattcca gaagtagtga ggaggctttt ttggaggcct aggcttttgc    1860
aaagatcgat caagagacag gatgaggatc gtttcgcatg attgaacaag atggattgca    1920
cgcaggttct ccggccgctt gggtggagag gctattcggc tatgactggg cacaacagac    1980
aatcggctgc tctgatgccg ccgtgttccg gctgtcagcg caggggcgcc cggttctttt    2040
tgtcaagacc gacctgtccg gtgccctgaa tgaactgcaa gacgaggcag cgcggctatc    2100
gtggctggcc acgacgggcg ttccttgcgc agctgtgctc gacgttgtca ctgaagcggg    2160
aagggactgg ctgctattgg gcgaagtgcc ggggcaggat ctcctgtcat ctcaccttgc    2220
tcctgccgag aaagtatcca tcatggctga tgcaatgcgg cggctgcata cgcttgatcc    2280
ggctacctgc ccattcgacc accaagcgaa acatcgcatc gagcgagcac gtactcggat    2340
ggaagccggt cttgtcgatc aggatgatct ggacgaagag catcaggggc tcgcgccagc    2400
cgaactgttc gccaggctca aggcgagcat gcccgacggc gaggatctcg tcgtgaccca    2460
tggcgatgcc tgcttgccga atatcatggt ggaaaatggc cgcttttctg gattcatcga    2520
ctgtggccgg ctgggtgtgg cggaccgcta tcaggacata gcgttggcta cccgtgatat    2580
tgctgaagag cttggcggcg aatgggctga ccgcttcctc gtgctttacg gtatcgccgc    2640
tcccgattcg cagcgcatcg ccttctatcg ccttcttgac gagttcttct gagcgggact    2700
ctggggttcg aaatgaccga ccaagcgacg cccaacctgc catcacgaga tttcgattcc    2760
accgccgcct tctatgaaag gttgggcttc ggaatcgttt tccgggacgc cggctggatg    2820
atcctccagc gcggggatct catgctggag ttcttcgccc accctagggg gaggctaact    2880
gaaacacgga aggagacaat accggaagga acccgcgcta tgacggcaat aaaaagacag    2940
aataaaacgc acggtgttgg gtcgtttgtt cataaacgcg gggttcggtc ccagggctgg    3000
cactctgtcg ataccccacc gagaccccat tggggccaat acgcccgcgt tcttcctttt    3060
tcccaccccc acccccaag ttcgggtgaa ggcccagggc tcgcagccaa cgtcggggcg    3120
gcaggccctg ccatagcctc aggttactca tatatacttt agattgattt aaaacttcat    3180
ttttaattta aaaggatcta ggtgaagatc ctttttgata atctcatgac caaaatccct    3240
taacgtgagt tttcgttcca ctgagcgtca gaccccgtag aaaagatcaa aggatcttct    3300
tgagatcctt ttttctgcg cgtaatctgc tgcttgcaaa caaaaaaacc accgctacca    3360
gcggtggttt gtttgccgga tcaagagcta ccaactcttt ttccgaaggt aactggcttc    3420
agcagagcgc agataccaaa tactgtcctt ctagtgtagc cgtagttagg ccaccacttc    3480
aagaactctg tagcaccgcc tacatacctc gctctgctaa tcctgttacc agtggctgct    3540
gccagtggcg ataagtcgtg tcttaccggg ttggactcaa gacgatagtt accggataag    3600
gcgcagcggt cgggctgaac ggggggttcg tgcacacagc ccagcttgga gcgaacgacc    3660
tacaccgaac tgagatacct acagcgtgag ctatgagaaa gcgccacgct tcccgaaggg    3720
agaaaggcgg acaggtatcc ggtaagcggc agggtcggaa caggagagcg cacgagggag    3780
```

```
cttccagggg gaaacgcctg gtatctttat agtcctgtcg ggtttcgcca cctctgactt    3840
gagcgtcgat ttttgtgatg ctcgtcaggg gggcggagcc tatggaaaaa cgccagcaac    3900
gcggcctttt tacggttcct ggccttttgc tggccttttg ctcacatgtt ctttcctgcg    3960
ttatcccctg attctgtgga taaccgtatt accgccatgc at                       4002
```

<210> SEQ ID NO 16
<211> LENGTH: 242
<212> TYPE: PRT
<213> ORGANISM: Artificial Sequence
<220> FEATURE:
<223> OTHER INFORMATION: Siglec-15 fragment

<400> SEQUENCE: 16

```
Val Arg Thr Lys Ile Asp Thr Thr Glu Asn Leu Leu Asn Thr Glu Val
1               5                   10                  15

His Ser Ser Pro Ala Gln Arg Trp Ser Met Gln Val Pro Pro Glu Val
            20                  25                  30

Ser Ala Glu Ala Gly Asp Ala Ala Val Leu Pro Cys Thr Phe Thr His
        35                  40                  45

Pro His Arg His Tyr Asp Gly Pro Leu Thr Ala Ile Trp Arg Ala Gly
    50                  55                  60

Glu Pro Tyr Ala Gly Pro Gln Val Phe Arg Cys Ala Ala Ala Arg Gly
65                  70                  75                  80

Ser Glu Leu Cys Gln Thr Ala Leu Ser Leu His Gly Arg Phe Arg Leu
                85                  90                  95

Leu Gly Asn Pro Arg Arg Asn Asp Leu Ser Leu Arg Val Glu Arg Leu
            100                 105                 110

Ala Leu Ala Asp Asp Arg Arg Tyr Phe Cys Arg Val Glu Phe Ala Gly
        115                 120                 125

Asp Val His Asp Arg Tyr Glu Ser Arg His Gly Val Arg Leu His Val
    130                 135                 140

Thr Ala Ala Pro Arg Ile Val Asn Ile Ser Val Leu Pro Ser Pro Ala
145                 150                 155                 160

His Ala Phe Arg Ala Leu Cys Thr Ala Glu Gly Glu Pro Pro Pro Ala
                165                 170                 175

Leu Ala Trp Ser Gly Pro Ala Leu Gly Asn Ser Leu Ala Ala Val Arg
            180                 185                 190

Ser Pro Arg Glu Gly His Gly His Leu Val Thr Ala Glu Leu Pro Ala
        195                 200                 205

Leu Thr His Asp Gly Arg Tyr Thr Cys Thr Ala Ala Asn Ser Leu Gly
    210                 215                 220

Arg Ser Glu Ala Ser Val Tyr Leu Phe Arg Phe His Gly Ala Ser Gly
225                 230                 235                 240

Ala Ser
```

<210> SEQ ID NO 17
<211> LENGTH: 34
<212> TYPE: DNA
<213> ORGANISM: Artificial Sequence
<220> FEATURE:
<223> OTHER INFORMATION: forward primer incorporating a BamHI
      restriction site

<400> SEQUENCE: 17

```
gtaagcggat ccgtgagaac taaaatagat acta                                34
```

<210> SEQ ID NO 18

```
<211> LENGTH: 41
<212> TYPE: DNA
<213> ORGANISM: Artificial Sequence
<220> FEATURE:
<223> OTHER INFORMATION: reverse primer incorporating a NotI restriction
      site

<400> SEQUENCE: 18
gtaagcgcgg ccgcgctggc gccatggaag cggaacaggt a                 41

<210> SEQ ID NO 19
<211> LENGTH: 5138
<212> TYPE: DNA
<213> ORGANISM: Artificial Sequence
<220> FEATURE:
<223> OTHER INFORMATION: expression vector pYD5

<400> SEQUENCE: 19
gtacatttat attggctcat gtccaatatg accgccatgt tgacattgat tattgactag      60
ttattaatag taatcaatta cggggtcatt agttcatagc ccatatatgg agttccgcgt     120
tacataactt acggtaaatg ccccgcctgg ctgaccgccc aacgaccccc gcccattgac     180
gtcaataatg acgtatgttc ccatagtaac gccaataggg actttccatt gacgtcaatg     240
ggtggagtat ttacggtaaa ctgcccactt ggcagtacat caagtgtatc atatgccaag     300 tccgcccct attgacgtca atgacggtaa atggcccgcc tggcattatg cccagtacat     360
gaccttacgg gactttccta cttggcagta catctacgta ttagtcatcg ctattaccat     420
ggtgatgcgg ttttggcagt acaccaatgg gcgtggatag cggtttgact cacggggatt     480
tccaagtctc cacccattg acgtcaatgg gagtttgttt tggcaccaaa atcaacggga     540
ctttccaaaa tgtcgtaata accccgcccc gttgacgcaa atgggcggta ggcgtgtacg     600
gtgggaggtc tatataagca gagctcgttt agtgaaccgt cagatcctca ctctcttccg     660
catcgctgtc tgcgagggcc agctgttggg ctcgcggttg aggacaaact cttcgcggtc     720
tttccagtac tcttggatcg gaaacccgtc ggcctccgaa cggtactccg ccaccgaggg     780
acctgagcca gtccgcatcg accggatcgg aaaacctctc gagaaaggcg tctaaccagt     840
cacagtcgca aggtaggctg agcaccgtgg cgggcggcag cgggtggcgg tcggggttgt     900
ttctggcgga ggtgctgctg atgatgtaat taaagtaggc ggtcttgagc cggcggatgg     960
tcgaggtgag gtgtggcagg cttgagatcc agctgttggg gtgagtactc cctctcaaaa    1020
gcgggcatga cttctgcgct aagattgtca gtttccaaaa acgaggagga tttgatattc    1080
acctggcccg atctggccat acacttgagt gacaatgaca tccactttgc ctttctctcc    1140
acaggtgtcc actcccaggt ccaagtttgc cgccaccatg gagacagaca cactcctgct    1200
atgggtactg ctgctctggg ttccaggttc cactggcgcc ggatcaactc acacatgccc    1260
accgtgccca gcacctgaac tcctgggggg accgtcagtc ttcctcttcc cccaaaaacc    1320
caaggacacc ctcatgatct cccggacccc tgaggtcaca tgcgtggtgg tggacgtgag    1380
ccacgaagac cctgaggtca agttcaactg gtacgtggac ggcgtggagg tgcataatgc    1440
caagacaaag ccgcgggagg agcagtacaa cagcacgtac cgtgtggtca gcgtcctcac    1500
cgtcctgcac caggactggc tgaatggcaa ggagtacaag tgcaaggtct ccaacaaagc    1560
cctcccagcc cccatcgaga aaccatctc caaagccaaa gggcagcccc gagaaccaca    1620
ggtgtacacc ctgcccccat cccgggatga gctgaccaag aaccaggtca gcctgacctg    1680
cctggtcaaa ggcttctatc ccagcgacat cgccgtggag tgggagagca atgggcagcc    1740
ggagaacaac tacaagacca cgcctcccgt gttggactcc gacggctcct tcttcctcta    1800
```

```
cagcaagctc accgtggaca agagcaggtg gcagcagggg aacgtcttct catgctccgt   1860
gatgcatgag gctctgcaca accactacac gcagaagagc ctctccctgt ctcccgggaa   1920
agctagcgga gccggaagca caaccgaaaa cctgtatttt cagggcggat ccgaattcaa   1980
gcttgatatc tgatccccg acctcgacct ctggctaata aggaaattt attttcattg     2040 caatagtgtg ttggaatttt ttgtgtctct cactcggaag gacatatggg agggcaaatc   2100
atttggtcga gatccctcgg agatctctag ctagagcccc gccgccggac gaactaaacc   2160
tgactacggc atctctgccc cttcttcgcg gggcagtgca tgtaatccct tcagttggtt   2220
ggtacaactt gccaactgaa ccctaaacgg gtagcatatg cttcccgggt agtagtatat   2280
actatccaga ctaaccctaa ttcaatagca tatgttaccc aacgggaagc atatgctatc   2340
gaattagggt tagtaaaagg gtcctaagga acagcgatgt aggtgggcgg gccaagatag   2400
gggcgcgatt gctgcgatct ggaggacaaa ttacacacac ttgcgcctga gcgccaagca   2460
cagggttgtt ggtcctcata ttcacgaggt cgctgagagc acggtgggct aatgttgcca   2520
tgggtagcat atactaccca aatatctgga tagcatatgc tatcctaatc tatatctggg   2580
tagcataggc tatcctaatc tatatctggg tagcatatgc tatcctaatc tatatctggg   2640
tagtatatgc tatcctaatt tatatctggg tagcataggc tatcctaatc tatatctggg   2700
tagcatatgc tatcctaatc tatatctggg tagtatatgc tatcctaatc tgtatccggg   2760
tagcatatgc tatcctaata gagattaggg tagtatatgc tatcctaatt tatatctggg   2820
tagcatatac tacccaaata tctggatagc atatgctatc ctaatctata tctgggtagc   2880
atatgctatc ctaatctata tcgggtagc ataggctatc caatctata tctgggtagc    2940 atatgctatc ctaatctata tctgggtagt atatgctatc ctaatttata tctgggtagc   3000
ataggctatc ctaatctata tctgggtagc atatgctatc ctaatctata tctgggtagt   3060
atatgctatc ctaatctgta tccgggtagc atatgctatc ctcacgatga taagctgtca   3120
aacatgagaa ttaattcttg aagacgaaag ggcctcgtga tacgcctatt tttataggtt   3180
aatgtcatga taataatggt tccttagacg tcaggtggca cttttcgggg aaatgtgcgc   3240 ggaacccta tttgtttatt tttctaaata cattcaaata tgtatccgct catgagacaa   3300
taaccctgat aaatgcttca ataatattga aaaggaaga gtatgagtat tcaacatttc   3360
cgtgtcgccc ttattccctt ttttgcggca ttttgccttc ctgttttgc tcacccagaa   3420 acgctggtga agtaaaaga tgctgaagat cagttgggtg cacgagtggg ttacatcgaa   3480
ctggatctca acagcggtaa gatccttgag agttttcgcc ccgaagaacg ttttccaatg   3540
atgagcactt ttaaagttct gctatgtggc gcggtattat cccgtgttga cgccgggcaa   3600
gagcaactcg gtcgccgcat acactattct cagaatgact tggttgagta ctcaccagtc   3660
acagaaaagc atcttacgga tggcatgaca gtaagagaat tatgcagtgc tgccataacc   3720
atgagtgata acactgcggc caacttactt ctgacaacga tcggaggacc gaaggagcta   3780
accgcttttt tgcacaacat gggggatcat gtaactcgcc ttgatcgttg ggaaccggag   3840
ctgaatgaag ccataccaaa cgacgagcgt gacaccacga tgcctgcagc aatggcaaca   3900
acgttgcgca aactattaac tggcgaacta cttactctag cttcccggca acaattaata   3960
gactggatgg aggcggataa agttgcagga ccacttctgc gctcggccct tccggctggc   4020
tggtttattg ctgataaatc tggagccggt gagcgtgggt ctcgcggtat cattgcagca   4080
ctggggccag atggtaagcc ctcccgtatc gtagttatct acacgacggg gagtcaggca   4140
actatggatg aacgaaatag acagatcgct gagataggtg cctcactgat taagcattgg   4200
```

```
taactgtcag accaagttta ctcatatata ctttagattg atttaaaact tcatttttaa   4260
tttaaaagga tctaggtgaa gatccttttt gataatctca tgaccaaaat cccttaacgt   4320
gagttttcgt tccactgagc gtcagacccc gtagaaaaga tcaaaggatc ttcttgagat   4380
cctttttttc tgcgcgtaat ctgctgcttg caaacaaaaa aaccaccgct accagcggtg   4440
gtttgtttgc cggatcaaga gctaccaact cttttccga aggtaactgg cttcagcaga    4500
gcgcagatac caaatactgt ccttctagtg tagccgtagt taggccacca cttcaagaac   4560
tctgtagcac cgcctacata cctcgctctg ctaatcctgt taccagtggc tgctgccagt   4620
ggcgataagt cgtgtcttac cgggttggac tcaagacgat agttaccgga taaggcgcag   4680
cggtcgggct gaacggggg ttcgtgcaca cagcccagct tggagcgaac gacctacacc    4740
gaactgagat acctacagcg tgagcattga gaaagcgcca cgcttcccga agggagaaag   4800
gcggacaggt atccggtaag cggcagggtc ggaacaggag agcgcacgag ggagcttcca   4860
gggggaaacg cctggtatct ttatagtcct gtcgggtttc gccacctctg acttgagcgt   4920 cgattttgt gatgctcgtc agggggggcgg agcctatgga aaaacgccag caacgcggcc    4980
tttttacggt tcctggcctt tgctggcct tttgctcaca tgttctttcc tgcgttatcc     5040
cctgattctg tggataaccg tattaccgcc tttgagtgag ctgataccgc tcgccgcagc   5100
cgaacgaccg agcgcagcga gtcagtgagc gaggaagc                            5138

<210> SEQ ID NO 20
<211> LENGTH: 642
<212> TYPE: DNA
<213> ORGANISM: Artificial Sequence
<220> FEATURE:
<223> OTHER INFORMATION: 25A1 light chain sequence

<400> SEQUENCE: 20
gaaaatgtgc tcacccagtc tccagcaatc atgtctgcat ctccagggga gaaggtcacc     60
atatcctgca gtgccagctc aagtgtaagt tacatgtact ggtaccagca gaagccagga    120
tcctccccca aaccctggat ttatcgcaca tccaacctgg cttctggagt ccctgctcgc    180
ttcagtggca gtgggtctgg gacctcttac tctctcacaa tcagcagcat ggaggctgaa    240
gatgctgcca cttattactg ccagcagtgg agtagtaacc cactcacgtt cggtgctggg    300
accaagctgg agctgaaacg ggctgtggct gcaccatctg tcttcatctt cccgccatct    360
gatgagcagt tgaaatctgg aactgcctct gttgtgtgcc tgctgaataa cttctatccc    420
agagaggcca aagtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtt ag                       642

<210> SEQ ID NO 21
<211> LENGTH: 211
<212> TYPE: PRT
<213> ORGANISM: Artificial Sequence
<220> FEATURE:
<223> OTHER INFORMATION: 25A1 light chain sequence

<400> SEQUENCE: 21

Glu Asn Val Leu Thr Gln Ser Pro Ala Ile Met Ser Ala Ser Pro Gly
1               5                   10                  15

Glu Lys Val Thr Ile Ser Cys Ser Ala Ser Ser Val Ser Tyr Met
            20                  25                  30
```

Tyr Trp Tyr Gln Gln Lys Pro Gly Ser Ser Lys Pro Trp Ile Tyr
            35                  40                  45

Arg Thr Ser Asn Leu Ala Ser Gly Val Pro Ala Arg Phe Ser Gly Ser
 50                  55                  60

Gly Ser Gly Thr Ser Tyr Ser Leu Thr Ile Ser Met Glu Ala Glu
 65                  70                  75                  80

Asp Ala Ala Thr Tyr Tyr Cys Gln Gln Trp Ser Ser Asn Pro Leu Thr
                 85                  90                  95

Phe Gly Ala Gly Thr Lys Leu Glu Leu Lys Val Ala Ala Pro Ser Val
                100                 105                 110

Phe Ile Phe Pro Pro Ser Asp Glu Gln Leu Lys Ser Gly Thr Ala Ser
            115                 120                 125

Val Val Cys Leu Leu Asn Asn Phe Tyr Pro Arg Glu Ala Lys Val Gln
        130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 22
<211> LENGTH: 1353
<212> TYPE: DNA
<213> ORGANISM: Artificial Sequence
<220> FEATURE:
<223> OTHER INFORMATION: 25A1 heavy chain sequence

<400> SEQUENCE: 22
gaggtccagc tgcaacaatc tgggactgag ctggtgaggc ctgggtcctc agtgaagatt     60
tcctgcaagg cttctggcta caccttcacc aggtactgga tggactgggt gaagcagagg    120
cctggacaag gccttgagtg gatcggagag attgatcctt ctgatagtta tactaactac    180
aatcaaaagt tcaagggcaa ggccacattg actgtagata aattctccag aacagcctat    240
atggaactca gcagcctgac atctgaggac tctgcggtct attactgtgc aagatcgggg    300
gcctactcta gtgactatag ttacgacggg tttgcttact ggggccaagg gactctggtc    360
actgtctctg cagcctcaac aaagggccca tcggtcttcc ccctggcgcc ctgctccagg    420
agcacctccg agagcacagc cgccctgggc tgcctggtca aggactactt ccccgaaccg    480
gtgacggtgt cgtggaactc aggcgctctg accagcggcg tgcacacctt cccagctgtc    540
ctacagtcct caggactcta ctccctcagc agcgtggtga ccgtgccctc agcaacttc     600 ggcacccaga cctacacctg caacgtagat cacaagccca gcaacaccaa ggtggacaag    660
acagttgagc gcaaatgttg tgtcgagtgc ccaccgtgcc cagcaccacc tgtggcagga    720
ccgtcagtct tcctcttccc cccaaaaccc aaggacaccc gcatgatctc ccggacccct    780
gaggtcacgt gcgtggtggt ggatgtgagc cacgaagacc ccgaggtcca gttcaactgg    840
tacgtggacg gcgtggaggt gcataatgcc aagacaaagc cacgggagga gcagttcaac    900
agcacgttcc gtgtggtcag cgtcctcacc gttgtgcacc aggactggct gaacggcaag    960
gagtacaagt gcaaggtctc caacaaaggc ctcccagccc ccatcgagaa aaccatctcc   1020

```
aaaaccaaag ggcagccccg agaaccacag gtgtacaccc tgcccccatc ccgggaggag    1080
atgaccaaga accaggtcag cctgacctgc ctggtcaaag gcttctaccc cagcgacatc    1140
gccgtggagt gggagagcaa tgggcagccg gagaacaact acaagaccac acctcccatg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353

<210> SEQ ID NO 23
<211> LENGTH: 450
<212> TYPE: PRT
<213> ORGANISM: Artificial Sequence
<220> FEATURE:
<223> OTHER INFORMATION: 25A1 heavy chain sequence

<400> SEQUENCE: 23

Glu Val Gln Leu Gln Gln Ser Gly Thr Glu Leu Val Arg Pro Gly Ser
1               5                   10                  15

Ser Val Lys Ile Ser Cys Lys Ala Ser Gly Tyr Thr Phe Thr Arg Tyr
            20                  25                  30

Trp Met Asp Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ala Thr Leu Thr Val Asp Lys Phe Ser Arg Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Ala Tyr Ser Ser Asp Tyr Ser Tyr Asp Gly Phe Ala
            100                 105                 110

Tyr Trp Gly Gln Gly Thr Leu Val Thr Val Ser Ala Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Asn Phe Gly Thr Gln Thr Tyr Thr Cys Asn
        195                 200                 205

Val Asp His Lys Pro Ser Asn Thr Lys Val Asp Lys Thr Val Glu Arg
    210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300
```

Val Val Ser Val Leu Thr Val His Gln Asp Trp Leu Asn Gly Lys
305                 310                 315                 320

Glu Tyr Lys Cys Lys Val Ser Asn Lys Gly Leu Pro Ala Pro Ile Glu
            325                 330                 335

Lys Thr Ile Ser Lys Thr Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 24
<211> LENGTH: 660
<212> TYPE: DNA
<213> ORGANISM: Artificial Sequence
<220> FEATURE:
<223> OTHER INFORMATION: 25B4 light chain sequence

<400> SEQUENCE: 24
gatattgtga tgacccaggc tgcattctcc aatccagtca ctcttggaac atcagcttcc      60
atctcctgca ggtctagtaa gagtctccta catagtaatg gcatcactta tttgtattgg     120
tatctgcaga agccaggcca gtctcctcag ctccctgattt atcagatgtc caaccttgcc    180
tcaggagtcc cagacaggtt cagtggcagt gggtcaggaa ctgctttcac actgagaatc     240
agtagagtgg aggctgagga tgtgggtgtt tattactgta tgcaacatct agaatatccg     300
tacacgttcg gaggggggac caagctggaa ataaaacggg ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 25
<211> LENGTH: 217
<212> TYPE: PRT
<213> ORGANISM: Artificial Sequence
<220> FEATURE:
<223> OTHER INFORMATION: 25B4 light chain sequence

<400> SEQUENCE: 25

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

```
Pro Gln Leu Leu Ile Tyr Gln Met Ser Asn Leu Ala Ser Gly Val Pro
     50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                 85                  90                  95

Leu Glu Tyr Pro Tyr Thr Phe Gly Gly Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 26
<211> LENGTH: 1335
<212> TYPE: DNA
<213> ORGANISM: Artificial Sequence
<220> FEATURE:
<223> OTHER INFORMATION: 25B4 heavy chain sequence

<400> SEQUENCE: 26
caggtccaag tgcagcagcc tggggctgaa attgtgaggc tggggcttca gtgaagctg      60 tcctgcaagg cttctggcta caccttcacc agctactgga tgcactgggt gaagcagagg    120
cctggacaag gccttgagtg gattggactg attaatccta ccaacggtcg tactaactac    180
aatgagaagt tcaagagcaa ggccacactg actgtagaca atcctccag cacagcctac     240 atgcaactca gcagcctgac atctgaggac tctgcggtct attactgtgc aagagggggg    300 gacgggggact actttgacta ctggggccaa ggcaccactc tcacagtctc ctcagcctca   360
acgaagggcc catcggtctt ccccctggcg ccctgctcca ggagcacctc cgagagcaca    420
gccgccctgg gctgcctggt caaggactac ttccccgaac cggtgacggt gtcgtggaac    480
tcaggcgctc tgaccagcgg cgtgcacacc ttcccagctg tcctacagtc ctcaggactc    540
tactccctca gcagcgtggt gaccgtgccc tccagcaact tcggcaccca gacctacacc    600
tgcaacgtag atcacaagcc cagcaacacc aaggtggaca gacagttga gcgcaaatgt     660 tgtgtcgagt gcccaccgtg cccagcacca cctgtggcag gaccgtcagt cttccgcttc    720
cccccaaaac ccaaggacac cgccatgatc tcccggaccc tgaggtcac gtgcgtggtg     780 gtggatgtga gccacgaaga ccccgaggtc cagttcaact ggtacgtgga cggcgtggag    840
gtgcataatg ccaagacaaa gccacgggag gagcagttca acagcacgtt ccgtgtggtc    900
agcgtcctca ccgttgtgca ccaggactgg ctgaacggca aggagtacaa gtgcaaggtc    960
tccaacaaag gcctcccagc ccccatcgag aaaaccatct ccaaaaccaa agggcagccc   1020
cgagaaccac aggtgtacac cctgccccca tcccgggagg agatgaccaa gaaccaggtc   1080
```

```
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aatga                                                     1335
```

<210> SEQ ID NO 27
<211> LENGTH: 444
<212> TYPE: PRT
<213> ORGANISM: Artificial Sequence
<220> FEATURE:
<223> OTHER INFORMATION: 25B4 heavy chain sequence

<400> SEQUENCE: 27

```
Gln Val Gln Val Gln Gln Pro Gly Ala Glu Ile Val Arg Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320
```

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 28
<211> LENGTH: 660
<212> TYPE: DNA
<213> ORGANISM: Artificial Sequence
<220> FEATURE:
<223> OTHER INFORMATION: 25B8 light chain sequence

<400> SEQUENCE: 28
gatattgtga tgacccaggc tgcaccctct gtacctgtca ctcctggaga gtcagtatcc      60
atctcctgca ggtctactaa gagtctcctg catagtaatg caacacttta cttgtattgg     120
ttcctgcaga ggccaggcca gtctcctcag ctcctgatat atcggatgtc aaccttgcc      180 tcaggagtcc cagacaggtt cagtggcagt gggtcaggaa ctgctttcac actgagaatc    240
agtagagtgg aggctgagga tgtgggtgtt tattactgta tgcaacatct agaatatcct     300
ttcacgttcg gagggggac caagctggaa ataaaacggg ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 29
<211> LENGTH: 217
<212> TYPE: PRT
<213> ORGANISM: Artificial Sequence
<220> FEATURE:
<223> OTHER INFORMATION: 25B8 light chain sequence

<400> SEQUENCE: 29

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

```
Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Val Ala Ala Pro Ser Val Phe Ile Phe Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 30
<211> LENGTH: 1350
<212> TYPE: DNA
<213> ORGANISM: Artificial Sequence
<220> FEATURE:
<223> OTHER INFORMATION: 25B8 heavy chain sequence

<400> SEQUENCE: 30

```
gagatccagc tgcagcagtc tggagttgag ctggtgaggc ctggggcttc agtgacgctg      60
tcctgcaagg cttcgggcta cacatttact gactatgaca tgcactgggt gaagcagaca    120
cctgttcatg gcctggaatg gattggaact attgatcctg aaactggtgg tactgcctac    180
aatcagaagt tcaagggcaa ggccacactg actgcggaca tcctccacac acagcctac    240
atggagctca gcagcctgac atctgaggac tctgccgtct attactgtac aactttctac    300
tatagtcact ataattacga cgtgggggttt gcttactggg gccaagggac tctggtcact    360
gtctctgcag cctcaacgaa gggcccatcg gtcttccccc tggcgccctg ctccaggagc    420
acctccgaga gcacagccgc cctgggctgc ctggtcaagg actacttccc cgaaccggtg    480
acggtgtcgt ggaactcagg cgctctgacc agcggcgtgc acaccttccc agctgtccta    540
cagtcctcag gactctactc cctcagcagc gtggtgaccg tgccctccag caacttcggc    600
acccagacct acacctgcaa cgtagatcac aagcccagca caccaaggt ggacaagaca    660
gttgagcgca atgttgtgt cgagtgccca ccgtgcccag caccacctgt ggcaggaccg    720
tcagtcttcc gcttcccccc aaaacccaag gacaccccgca tgatctcccg gacccctgag    780
gtcacgtgcg tggtggtgga tgtgagccac gaagaccccg aggtccagtt caactggtac    840
gtggacggcg tggaggtgca taatgccaag acaaagccac gggaggagca gttcaacagc    900
acgttccgtg tggtcagcgt cctcaccgtt gtgcaccagg actggctgaa cggcaaggag    960
tacaagtgca aggtctccaa caaaggcctc ccagcccca tcgagaaaac catctccaaa   1020
accaaagggc agccccgaga accacaggtg tacaccctgc ccccatcccg ggaggagatg   1080
accaagaacc aggtcagcct gacctgcctg gtcaaaggct tctaccccag cgacatcgcc   1140
gtggagtggg agagcaatgg gcagccggag aacaactaca agaccacacc tcccatgctg   1200
gactccgacg gctccttctt cctctacagc aagctcaccg tggacaagag caggtggcag   1260
```

```
cagggggaacg tcttctcatg ctccgtgatg catgaggctc tgcacaacca ctacacgcag    1320
aagagcctct ccctgtctcc gggtaaatga                                       1350
```

<210> SEQ ID NO 31
<211> LENGTH: 449
<212> TYPE: PRT
<213> ORGANISM: Artificial Sequence
<220> FEATURE:
<223> OTHER INFORMATION: 25B8 heavy chain sequence

<400> SEQUENCE: 31

```
Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Thr Thr Phe Tyr Tyr Ser His Tyr Asn Tyr Asp Val Gly Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Met Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
Ala Leu His Asn His Tyr Thr Gln Lys Ser Leu Ser Leu Ser Pro Gly
            435                 440                 445
Lys

<210> SEQ ID NO 32
<211> LENGTH: 660
<212> TYPE: DNA
<213> ORGANISM: Artificial Sequence
<220> FEATURE:
<223> OTHER INFORMATION: 25C1 light chain sequence

<400> SEQUENCE: 32
gatattgtga tgacccaggc tgcaccctct gtacctgtca ctcctggaga gtcagtatcc      60
atctcctgca ggtctagtaa gagtctcctg catagtaatg caacacttaa cttgtattgg     120
ttcctgcaga ggccaggcca gtcccctcag ctcctgatat atcggatgtc aaccttgcc    180 tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg gaggggggac caagctggaa ataaaacggg ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 33
<211> LENGTH: 217
<212> TYPE: PRT
<213> ORGANISM: Artificial Sequence
<220> FEATURE:
<223> OTHER INFORMATION: 25C1 light chain sequence

<400> SEQUENCE: 33

Asp Ile Val Met Thr Gln Ala Ala Pro Ser Val Pro Val Thr Pro Gly
1               5                   10                  15
Glu Ser Val Ser Ile Ser Cys Arg Ser Ser Lys Ser Leu Leu His Ser
                20                  25                  30
Asn Gly Asn Thr Tyr Leu Tyr Trp Phe Leu Gln Arg Pro Gly Gln Ser
            35                  40                  45
Pro Gln Leu Leu Ile Tyr Arg Met Ser Asn Leu Ala Ser Gly Val Pro
        50                  55                  60
Asp Arg Phe Ser Gly Ser Gly Ser Gly Thr Ala Phe Thr Leu Arg Ile
65                  70                  75                  80
Ser Arg Val Glu Ala Glu Asp Val Gly Val Tyr Tyr Cys Met Gln His
                85                  90                  95
```

```
Leu Glu Tyr Pro Phe Thr Phe Gly Gly Thr Lys Leu Glu Ile Lys
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 34
<211> LENGTH: 1422
<212> TYPE: DNA
<213> ORGANISM: Artificial Sequence
<220> FEATURE:
<223> OTHER INFORMATION: 25C1 heavy chain sequence

<400> SEQUENCE: 34
gagatccagc tgcagcagtc tggagctgag ctggtgaggc ctggggcttc agtgacgctg      60
tcctgcaagg cttcgggcta cacatttact gactatgaaa tgcactgggt gaagcagaca     120
cctgttcatg gcctggaatg gattggagct attgatcctg aaactggtgg tactgcctac     180
aatcagaagt tcaagggcaa ggccacactg actgcagaca atcctccag cacagcctac      240 atggagctca gcagcctgac atctgaggac tctgccgtct attactgtac aagtttctac     300
tatacttact ataattacga cgtggggttt gcttactggg gccaagggac tctggtcact     360
gtctctgcag cctcaactgg ggcgtcttat tactatgcta tggaccactg ggtcaagga      420 acctcagtca ccgtctcctc agcctcaacg aagggcccat cggtcttccc cctggcgccc     480
tgctccagga gcacctccga gagcacagcc gccctgggct gcctggtcaa ggactacttc     540
cccgaaccgg tgacggtgtc gtggaactca ggcgctctga ccagcggcgt gcacaccttc     600
ccagctgtcc tacagtcctc aggactctac tccctcagca gcgtggtgac cgtgccctcc     660
agcaacttcg gcacccagac ctacacctgc aacgtagatc acaagcccag caacaccaag     720
gtggacaaga cagttgagcg caaatgttgt gtcgagtgcc caccgtgccc agcaccacct     780
gtggcaggac cgtcagtctt ccgcttcccc ccaaaaccca aggacaccgc catgatctcc     840 cggaccctg aggtcacgtg cgtggtggtg gatgtgagcc acgaagaccc cgaggtccag      900
ttcaactggt acgtggacgg cgtggaggtg cataatgcca agacaaagcc acgggaggag     960
cagttcaaca gcacgttccg tgtggtcagc gtcctcaccg ttgtgcacca ggactggctg    1020
aacggcaagg agtacaagtg caaggtctcc aacaaaggcc tcccagcccc catcgagaaa    1080
accatctcca aaaccaaagg gcagccccga gaaccacagg tgtacaccct gcccccatcc    1140
cgggaggaga tgaccaagaa ccaggtcagc ctgacctgcc tggtcaaagg cttctacccc    1200
agcgacatcg ccgtggagtg ggagagcaat gggcagccgg agaacaacta caagaccaca    1260
cctcccatgc tggactccga cggctccttc ttcctctaca gcaagctcac cgtggacaag    1320
agcaggtggc agcaggggaa cgtcttctca tgctccgtga tgcatgaggc tctgcacaac    1380
```
cactacacgc agaagagcct ctccctgtct ccgggtaaat ga        1422

<210> SEQ ID NO 35
<211> LENGTH: 449
<212> TYPE: PRT
<213> ORGANISM: Artificial Sequence
<220> FEATURE:
<223> OTHER INFORMATION: 25C1 heavy chain sequence

<400> SEQUENCE: 35

Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Tyr Asn Tyr Asp Val Gly Phe Ala Tyr
            100                 105                 110

Trp Gly Gln Gly Thr Leu Val Thr Val Ser Ala Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 36
<211> LENGTH: 660
<212> TYPE: DNA
<213> ORGANISM: Artificial Sequence
<220> FEATURE:
<223> OTHER INFORMATION: 25D8 light chain sequence

<400> SEQUENCE: 36
gatattgtga tgacccaggc tgcattctcc aatccagtca ctcttggaac atcagcttcc      60
atctcctgca ggtctagtaa gagtctccta catagtaatg gcatcactta tttgtattgg     120
tatctgcaga agccaggcca gtctcctcag ctcctgattt atcagatgtc caaccttgcc     180
tcaggagtcc cagacaggtt cagtagcagt gggtcaggaa ctgatttcac actgagaatc     240
agcagagtgg aggctgagga tgtgggtgtt tattactgtg ctcaaaatct agaacttccg     300
tacacgttcg gaggggggac caagctggaa ataaaacggg ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 37
<211> LENGTH: 217
<212> TYPE: PRT
<213> ORGANISM: Artificial Sequence
<220> FEATURE:
<223> OTHER INFORMATION: 25D8 light chain sequence

<400> SEQUENCE: 37

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Leu Glu Ile Lys
            100                 105                 110

```
Val Ala Ala Pro Ser Val Phe Ile Phe Pro Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 38
<211> LENGTH: 1335
<212> TYPE: DNA
<213> ORGANISM: Artificial Sequence
<220> FEATURE:
<223> OTHER INFORMATION: 25D8 heavy chain sequence

<400> SEQUENCE: 38
caggtccaag tgcagcagcc tggggctgag cttgtgaagc ctggggcttc ggtgaagctg      60
tcctgcaagg cttctggcta caccttcacc agctactgga tgcactgggt gaagcagagg     120
cctggacaag gccttgagtg gattggactg attaatccta gcaacgctcg tactaactac    180
aatgagaagt tcaataccaa ggccacactg actgtagaca atcctccag cacagcctac      240 atgcaactca gcagcctgac atctgaggac tctgcggtct attactgtgc aagagggggg     300
gacggggact actttgacta ctggggccaa ggcaccactc tcacagtctc ctcagcctca     360
acgaagggcc catcggtctt ccccctggcg ccctgctcca ggagcacctc cgagagcaca     420
gccgccctgg gctgcctggt caaggactac ttccccgaac cggtgacggt gtcgtggaac     480
tcaggcgctc tgaccagcgg cgtgcacacc ttcccagctg tcctacagtc ctcaggactc     540
tactccctca gcagcgtggt gaccgtgccc tccagcaact cggcaccca gacctacacc      600 tgcaacgtag atcacaagcc cagcaacacc aaggtggaca gacagttga gcgcaaatgt      660 tgtgtcgagt gcccaccgtg cccagcacca cctgtggcag gaccgtcagt cttccgcttc     720
cccccaaaac ccaaggacac cgcatgatc tcccggaccc ctgaggtcac gtgcgtggtg      780
gtggatgtga gccacgaaga ccccgaggtc cagttcaact ggtacgtgga cggcgtggag     840
gtgcataatg ccaagacaaa gccacgggag gagcagttca acagcacgtt ccgtgtggtc     900
agcgtcctca ccgttgtgca ccaggactgg ctgaacggca aggagtacaa gtgcaaggtc     960
tccaacaaag gcctcccagc cccatcgag aaaaccatct ccaaaaccaa agggcagccc     1020
cgagaaccac aggtgtacac cctgccccca tcccgggagg agatgaccaa gaaccaggtc    1080
agcctgacct gcctggtcaa aggcttctac cccagcgaca tcgccgtgga gtgggagagc    1140
aatgggcagc cggagaacaa ctacaagacc acacctccca tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aatga                                                     1335

<210> SEQ ID NO 39
```

```
<211> LENGTH: 444
<212> TYPE: PRT
<213> ORGANISM: Artificial Sequence
<220> FEATURE:
<223> OTHER INFORMATION: 25D8 heavy chain sequence

<400> SEQUENCE: 39
```

| Gln | Val | Gln | Val | Gln | Gln | Pro | Gly | Ala | Glu | Leu | Val | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Leu | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Trp | Met | His | Trp | Val | Lys | Gln | Arg | Pro | Gly | Gln | Gly | Leu | Glu | Trp | Ile |
|---|---|---|---|---|---|---|---|---|---|---|---|---|---|---|---|
| | | 35 | | | | | 40 | | | | | 45 | | | |

| Gly | Leu | Ile | Asn | Pro | Ser | Asn | Ala | Arg | Thr | Asn | Tyr | Asn | Glu | Lys | Phe |
|---|---|---|---|---|---|---|---|---|---|---|---|---|---|---|---|
| | 50 | | | | | 55 | | | | | 60 | | | | |

| Asn | Thr | Lys | Ala | Thr | Leu | Thr | Val | Asp | Lys | Ser | Ser | Thr | Ala | Tyr |
|---|---|---|---|---|---|---|---|---|---|---|---|---|---|---|
| 65 | | | | | 70 | | | | | 75 | | | | 80 |

| Met | Gln | Leu | Ser | Ser | Leu | Thr | Ser | Glu | Asp | Ser | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Gly | Asp | Gly | Asp | Tyr | Phe | Asp | Tyr | Trp | Gly | Gln | Gly | Thr |
|---|---|---|---|---|---|---|---|---|---|---|---|---|---|---|---|
| | | | 100 | | | | | 105 | | | | | 110 | | |

| Thr | Leu | Thr | Val | Ser | Ser | Ala | Ser | Thr | Lys | Gly | Pro | Ser | Val | Phe | Pro |
|---|---|---|---|---|---|---|---|---|---|---|---|---|---|---|---|
| | | 115 | | | | | 120 | | | | | 125 | | | |

| Leu | Ala | Pro | Cys | Ser | Arg | Ser | Thr | Ser | Glu | Ser | Thr | Ala | Ala | Leu | Gly |
|---|---|---|---|---|---|---|---|---|---|---|---|---|---|---|---|
| | 130 | | | | | 135 | | | | | 140 | | | | |

| Cys | Leu | Val | Lys | Asp | Tyr | Phe | Pro | Glu | Pro | Val | Thr | Val | Ser | Trp | Asn |
|---|---|---|---|---|---|---|---|---|---|---|---|---|---|---|---|
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
|---|---|---|---|---|---|---|---|---|---|---|---|---|---|---|---|
| | | | | 165 | | | | | 170 | | | | | 175 | |

| Ser | Ser | Gly | Leu | Tyr | Ser | Leu | Ser | Ser | Val | Val | Thr | Val | Pro | Ser | Ser |
|---|---|---|---|---|---|---|---|---|---|---|---|---|---|---|---|
| | | | 180 | | | | | 185 | | | | | 190 | | |

| Asn | Phe | Gly | Thr | Gln | Thr | Tyr | Thr | Cys | Asn | Val | Asp | His | Lys | Pro | Ser |
|---|---|---|---|---|---|---|---|---|---|---|---|---|---|---|---|
| | | 195 | | | | | 200 | | | | | 205 | | | |

| Asn | Thr | Lys | Val | Asp | Lys | Thr | Val | Glu | Arg | Lys | Cys | Cys | Val | Glu | Cys |
|---|---|---|---|---|---|---|---|---|---|---|---|---|---|---|---|
| | 210 | | | | | 215 | | | | | 220 | | | | |

| Pro | Pro | Cys | Pro | Ala | Pro | Pro | Val | Ala | Gly | Pro | Ser | Val | Phe | Leu | Phe |
|---|---|---|---|---|---|---|---|---|---|---|---|---|---|---|---|
| 225 | | | | | 230 | | | | | 235 | | | | | 240 |

| Pro | Pro | Lys | Pro | Lys | Asp | Thr | Leu | Met | Ile | Ser | Arg | Thr | Pro | Glu | Val |
|---|---|---|---|---|---|---|---|---|---|---|---|---|---|---|---|
| | | | | 245 | | | | | 250 | | | | | 255 | |

| Thr | Cys | Val | Val | Val | Asp | Val | Ser | His | Glu | Asp | Pro | Glu | Val | Gln | Phe |
|---|---|---|---|---|---|---|---|---|---|---|---|---|---|---|---|
| | | | 260 | | | | | 265 | | | | | 270 | | |

| Asn | Trp | Tyr | Val | Asp | Gly | Val | Glu | Val | His | Asn | Ala | Lys | Thr | Lys | Pro |
|---|---|---|---|---|---|---|---|---|---|---|---|---|---|---|---|
| | | 275 | | | | | 280 | | | | | 285 | | | |

| Arg | Glu | Glu | Gln | Phe | Asn | Ser | Thr | Phe | Arg | Val | Val | Ser | Val | Leu | Thr |
|---|---|---|---|---|---|---|---|---|---|---|---|---|---|---|---|
| | 290 | | | | | 295 | | | | | 300 | | | | |

| Val | Val | His | Gln | Asp | Trp | Leu | Asn | Gly | Lys | Glu | Tyr | Lys | Cys | Lys | Val |
|---|---|---|---|---|---|---|---|---|---|---|---|---|---|---|---|
| 305 | | | | | 310 | | | | | 315 | | | | | 320 |

| Ser | Asn | Lys | Gly | Leu | Pro | Ala | Pro | Ile | Glu | Lys | Thr | Ile | Ser | Lys | Thr |
|---|---|---|---|---|---|---|---|---|---|---|---|---|---|---|---|
| | | | | 325 | | | | | 330 | | | | | 335 | |

| Lys | Gly | Gln | Pro | Arg | Glu | Pro | Gln | Val | Tyr | Thr | Leu | Pro | Pro | Ser | Arg |
|---|---|---|---|---|---|---|---|---|---|---|---|---|---|---|---|
| | | | 340 | | | | | 345 | | | | | 350 | | |

| Glu | Glu | Met | Thr | Lys | Asn | Gln | Val | Ser | Leu | Thr | Cys | Leu | Val | Lys | Gly |
|---|---|---|---|---|---|---|---|---|---|---|---|---|---|---|---|
| | | 355 | | | | | 360 | | | | | 365 | | | |

| Phe | Tyr | Pro | Ser | Asp | Ile | Ala | Val | Glu | Trp | Glu | Ser | Asn | Gly | Gln | Pro |
|---|---|---|---|---|---|---|---|---|---|---|---|---|---|---|---|
| | 370 | | | | | 375 | | | | | 380 | | | | |

```
Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly Lys
        435                 440

<210> SEQ ID NO 40
<211> LENGTH: 642
<212> TYPE: DNA
<213> ORGANISM: Artificial Sequence
<220> FEATURE:
<223> OTHER INFORMATION: 25E5 light chain sequence

<400> SEQUENCE: 40
caaattgttc tcacccagtc tccaacactc atgtctgcat ctccagggga gaaggtcacc      60
atgacctgca gtgccagctc aagtgtaagt tacatgtact ggtaccagca gaagccaaga     120
tcctccccca aaccctggat ttatcgcaca tccaacctgg tttctggagt ccctgtacgc     180
ttcagtggca gtgggtctgg gacctcttac tctctcacaa tcagcagcat ggaggctgaa     240
gatgctgcca cttattactg ccagcagtgg agtagtaacc cacccacgtt cggtgctggg     300
accaagctgg agctgaaacg ggctgtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgtt ag                       642

<210> SEQ ID NO 41
<211> LENGTH: 211
<212> TYPE: PRT
<213> ORGANISM: Artificial Sequence
<220> FEATURE:
<223> OTHER INFORMATION: 25E5 light chain sequence

<400> SEQUENCE: 41

Gln Ile Val Leu Thr Gln Ser Pro Thr Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Arg Thr Ser Asn Leu Val Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140
```

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
            165                 170                 175

Thr Leu Ser Lys Ala Asp Tyr Glu Lys His Lys Val Tyr Ala Cys Glu
        180                 185                 190

Val Thr His Gln Gly Leu Ser Ser Pro Val Thr Lys Ser Phe Asn Arg
    195                 200                 205

Gly Glu Cys
    210

<210> SEQ ID NO 42
<211> LENGTH: 1341
<212> TYPE: DNA
<213> ORGANISM: Artificial Sequence
<220> FEATURE:
<223> OTHER INFORMATION: 25E5 heavy chain sequence

<400> SEQUENCE: 42

```
gaagtgaagc ttgaggagtc tggaggtggc ctggtgcagc ctggaggatc cctgaaactc    60
tcctgtgcag cctcaggatt cgattttagt aaagactgga tgagttgggt ccggcaggct   120
ccagggaaag gctagaatg gattggagaa attaatccag atagcagtac gataaactat   180
gcaccatctc ttaaggataa attcatcatc tccagagaga cgccaaaaa tacgctgtac   240
ctgcaaatga gcaaagtgag atctgaggac acagcccttt attactgttc aagactagag   300
gactacgaag actggtactt cgatgtctgg ggcgcaggga ccacggtcac cgtctcctca   360
gcctcaacga agggcccatc ggtcttcccc ctggcgccct gctccaggag cacctccgag   420
agcacagccg ccctgggctg cctggtcaag gactacttcc ccgaaccggt gacggtgtcg   480
tggaactcag gcgctctgac cagcggcgtg cacaccttcc cagctgtcct acagtcctca   540
ggactctact ccctcagcag cgtggtgacc gtgccctcca gcaacttcgg cacccagacc   600
tacacctgca acgtagatca caagcccagc aacaccaagg tggacaagac agttgagcgc   660
aaatgttgtg tcgagtgccc accgtgccca gcaccacctg tggcaggacc gtcagtcttc   720
cgcttccccc caaaacccaa ggacacccgc atgatctccc ggacccctga ggtcacgtgc   780
gtggtggtgg atgtgagcca cgaagacccc gaggtccagt tcaactggta cgtggacggc   840
gtggaggtgc ataatgccaa gacaaagcca cgggaggagc agttcaacag cacgttccgt   900
gtggtcagcg tcctcaccgt tgtgcaccag gactggctga acggcaagga gtacaagtgc   960
aaggtctcca acaaaggcct cccagccccc atcgagaaaa ccatctccaa aaccaaaggg  1020
cagccccgag aaccacaggt gtacaccctg cccccatccc gggaggagat gaccaagaac  1080
caggtcagcc tgacctgcct ggtcaaaggc ttctacccca gcgacatcgc cgtggagtgg  1140
gagagcaatg ggcagccgga gaacaactac aagaccacac ctcccatgct ggactccgac  1200
ggctccttct tcctctacag caagctcacc gtggacaaga gcaggtggca gcaggggaac  1260
gtcttctcat gctccgtgat gcatgaggct ctgcacaacc actacacgca gaagagcctc  1320
tccctgtctc cgggtaaatg a                                            1341
```

<210> SEQ ID NO 43
<211> LENGTH: 446
<212> TYPE: PRT
<213> ORGANISM: Artificial Sequence
<220> FEATURE:
<223> OTHER INFORMATION: 25E5 heavy chain sequence

<400> SEQUENCE: 43

```
Glu Val Lys Leu Glu Glu Ser Gly Gly Gly Leu Val Gln Pro Gly Gly
 1               5                  10                  15
Ser Leu Lys Leu Ser Cys Ala Ala Ser Gly Phe Asp Phe Ser Lys Asp
            20                  25                  30
Trp Met Ser Trp Val Arg Gln Ala Pro Gly Lys Gly Leu Glu Trp Ile
        35                  40                  45
Gly Glu Ile Asn Pro Asp Ser Ser Thr Ile Asn Tyr Ala Pro Ser Leu
    50                  55                  60
Lys Asp Lys Phe Ile Ile Ser Arg Glu Asn Ala Lys Asn Thr Leu Tyr
 65                  70                  75                  80
Leu Gln Met Ser Lys Val Arg Ser Glu Asp Thr Ala Leu Tyr Tyr Cys
            85                  90                  95
Ser Arg Leu Glu Asp Tyr Glu Asp Trp Tyr Phe Asp Val Trp Gly Ala
        100                 105                 110
Gly Thr Thr Val Thr Val Ser Ser Ala Ser Thr Lys Gly Pro Ser Val
    115                 120                 125
Phe Pro Leu Ala Pro Cys Ser Arg Ser Thr Ser Glu Ser Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
            165                 170                 175
Leu Gln Ser Ser Gly Leu Tyr Ser Leu Ser Ser Val Val Thr Val Pro
        180                 185                 190
Ser Ser Asn Phe Gly Thr Gln Thr Tyr Thr Cys Asn Val Asp His Lys
    195                 200                 205
Pro Ser Asn Thr Lys Val Asp Lys Thr Val Glu Arg Lys Cys Cys Val
210                 215                 220
Glu Cys Pro Pro Cys Pro Ala Pro Pro Val Ala Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
        260                 265                 270
Gln Phe Asn Trp Tyr Val Asp Gly Val Glu Val His Asn Ala Lys Thr
    275                 280                 285
Lys Pro Arg Glu Glu Gln Phe Asn Ser Thr Phe Arg Val Val Ser Val
290                 295                 300
Leu Thr Val Val His Gln Asp Trp Leu Asn Gly Lys Glu Tyr Lys Cys
305                 310                 315                 320
Lys Val Ser Asn Lys Gly Leu Pro Ala Pro Ile Glu Lys Thr Ile Ser
            325                 330                 335
Lys Thr Lys Gly Gln Pro Arg Glu Pro Gln Val Tyr Thr Leu Pro Pro
        340                 345                 350
Ser Arg Glu Glu Met Thr Lys Asn Gln Val Ser Leu Thr Cys Leu Val
    355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Met Leu Asp Ser Asp
385                 390                 395                 400
Gly Ser Phe Phe Leu Tyr Ser Lys Leu Thr Val Asp Lys Ser Arg Trp
            405                 410                 415
```

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
            435                 440                 445

<210> SEQ ID NO 44
<211> LENGTH: 645
<212> TYPE: DNA
<213> ORGANISM: Artificial Sequence
<220> FEATURE:
<223> OTHER INFORMATION: 25E6 light chain sequence

<400> SEQUENCE: 44

```
agtattgtga tgacccagac tcccaaattc ctgcttgtat cagcaggaga cagggttacc      60
ataacctgca aggccagtca gagtgtgagt aatgctgtag cttggtacca acagaagcca     120
gggcagtctc ctaaactgct gatatactat acatccaatc gctacactgg agtccctgat     180
cgcttcactg gcagtggata tgggacggat ttcactttca ccatcaccac tgtgcaggct     240
gaagacctgg cagtttattt ctgtcagcag gattatacct ctccgtggac gttcggtgga     300
ggcaccaagc tggaaatcaa acgggctgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaacacaaa gtctacgcct gcgaagtcac ccatcagggc     600
ctgagctcgc ccgtcacaaa gagcttcaac aggggagagt gttag                    645
```

<210> SEQ ID NO 45
<211> LENGTH: 212
<212> TYPE: PRT
<213> ORGANISM: Artificial Sequence
<220> FEATURE:
<223> OTHER INFORMATION: 25E6 light chain sequence

<400> SEQUENCE: 45

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Ala
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Thr Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Lys Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
        180                 185                 190

Glu Val Thr His Gln Gly Leu Ser Ser Pro Val Thr Lys Ser Phe Asn
        195                 200                 205

Arg Gly Glu Cys
    210

<210> SEQ ID NO 46
<211> LENGTH: 1317
<212> TYPE: DNA
<213> ORGANISM: Artificial Sequence
<220> FEATURE:
<223> OTHER INFORMATION: 25E6 heavy chain sequence

<400> SEQUENCE: 46
caggtccaac tgcagcagcc tggggctgaa ctggcgaagc ctggggcttc agtgaagttg      60
tcctgcaagg cttctggcta caccttcaac acctataata tgtactggtt gaaacagagg     120
cctgggcaag gccttgagtg gattgggggg attgatccta gcaatggtga tactaaaatc     180
aatgagaagt tcaagaacaa ggccacactg actgttgaca atcctccag tacagcctat      240
atgcaactca gcggcctgac atctgaggac tctgcggtct attactgtac aagccatacg     300
tactggggcc aagggactct ggtcactgtc tctgcagcct caacgaaggg cccatcggtc     360
ttccccctgg cgccctgctc caggagcacc tccgagagca gccgccct gggctgcctg       420
gtcaaggact acttccccga accggtgacg gtgtcgtgga actcaggcgc tctgaccagc     480
ggcgtgcaca ccttcccagc tgtcctacag tcctcaggac tctactccct cagcagcgtg     540
gtgaccgtgc cctccagcaa cttcggcacc cagacctaca cctgcaacgt agatcacaag     600
cccagcaaca ccaaggtgga caagacagtt gagcgcaaat gttgtgtcga gtgcccaccg     660
tgcccagcac cacctgtggc aggaccgtca gtcttccgct tccccccaaa acccaaggac     720
acccgcatga tctcccggac ccctgaggtc acgtgcgtgg tggtggatgt gagccacgaa     780
gaccccgagg tccagttcaa ctggtacgtg gacggcgtgg aggtgcataa tgccaagaca     840
aagccacggg aggagcagtt caacagcacg ttccgtgtgg tcagcgtcct caccgttgtg     900
caccaggact ggctgaacgg caaggagtac aagtgcaagg tctccaacaa aggcctccca     960
gcccccatcg agaaaaccat ctccaaaacc aaagggcagc ccgagaacc acaggtgtac     1020
accctgcccc catcccggga ggagatgacc aagaaccagg tcagcctgac ctgcctggtc    1080
aaaggcttct accccagcga catcgccgtg gagtgggaga gcaatgggca gccggagaac    1140
aactacaaga ccacacctcc catgctggac tccgacggct ccttcttcct ctacagcaag    1200
ctcaccgtgg acaagagcag gtggcagcag gggaacgtct tctcatgctc cgtgatgcat    1260
gaggctctgc acaaccacta cacgcagaag agcctctccc tgtctccggg taaatga       1317

<210> SEQ ID NO 47
<211> LENGTH: 438
<212> TYPE: PRT
<213> ORGANISM: Artificial Sequence
<220> FEATURE:
<223> OTHER INFORMATION: 25E6 heavy chain sequence

<400> SEQUENCE: 47

Gln Val Gln Leu Gln Gln Pro Gly Ala Glu Leu Ala Lys Pro Gly Ala
1               5                   10                  15

Ser Val Lys Leu Ser Cys Lys Ala Ser Gly Tyr Thr Phe Asn Thr Tyr
            20                  25                  30

```
Asn Met Tyr Trp Leu Lys Gln Arg Pro Gly Gln Gly Leu Glu Trp Ile
     35                  40                  45

Gly Gly Ile Asp Pro Ser Asn Gly Asp Thr Lys Ile Asn Glu Lys Phe
 50                  55                  60

Lys Asn Lys Ala Thr Leu Thr Val Asp Lys Ser Ser Thr Ala Tyr
 65                  70                  75                  80

Met Gln Leu Ser Gly Leu Thr Ser Glu Asp Ser Ala Val Tyr Tyr Cys
             85                  90                  95

Thr Ser His Thr Tyr Trp Gly Gln Gly Thr Leu Val Thr Val Ser Ala
                100                 105                 110

Ala Ser Thr Lys Gly Pro Ser Val Phe Pro Leu Ala Pro Cys Ser Arg
            115                 120                 125

Ser Thr Ser Glu Ser Thr Ala Ala Leu Gly Cys Leu Val Lys Asp Tyr
        130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Asn Phe Gly Thr Gln Thr
            180                 185                 190

Tyr Thr Cys Asn Val Asp His Lys Pro Ser Asn Thr Lys Val Asp Lys
        195                 200                 205

Thr Val Glu Arg Lys Cys Cys Val Glu Cys Pro Pro Cys Pro Ala Pro
210                 215                 220

Pro Val Ala Gly Pro Ser Val Phe Leu Phe Pro Pro Lys Pro Lys Asp
225                 230                 235                 240

Thr Leu Met Ile Ser Arg Thr Pro Glu Val Thr Cys Val Val Val Asp
                245                 250                 255

Val Ser His Glu Asp Pro Glu Val Gln Phe Asn Trp Tyr Val Asp Gly
            260                 265                 270

Val Glu Val His Asn Ala Lys Thr Lys Pro Arg Glu Glu Gln Phe Asn
        275                 280                 285

Ser Thr Phe Arg Val Val Ser Val Leu Thr Val His Gln Asp Trp
290                 295                 300

Leu Asn Gly Lys Glu Tyr Lys Cys Lys Val Ser Asn Lys Gly Leu Pro
305                 310                 315                 320

Ala Pro Ile Glu Lys Thr Ile Ser Lys Thr Lys Gly Gln Pro Arg Glu
                325                 330                 335

Pro Gln Val Tyr Thr Leu Pro Pro Ser Arg Glu Glu Met Thr Lys Asn
            340                 345                 350

Gln Val Ser Leu Thr Cys Leu Val Lys Gly Phe Tyr Pro Ser Asp Ile
        355                 360                 365

Ala Val Glu Trp Glu Ser Asn Gly Gln Pro Glu Asn Asn Tyr Lys Thr
    370                 375                 380

Thr Pro Pro Met Leu Asp Ser Asp Gly Ser Phe Phe Leu Tyr Ser Lys
385                 390                 395                 400

Leu Thr Val Asp Lys Ser Arg Trp Gln Gln Gly Asn Val Phe Ser Cys
                405                 410                 415

Ser Val Met His Glu Ala Leu His Asn His Tyr Thr Gln Lys Ser Leu
            420                 425                 430

Ser Leu Ser Pro Gly Lys
            435

<210> SEQ ID NO 48
```

```
<211> LENGTH: 660
<212> TYPE: DNA
<213> ORGANISM: Artificial Sequence
<220> FEATURE:
<223> OTHER INFORMATION: 25E9 light chain sequence

<400> SEQUENCE: 48
gatattgtga tgacccaggc tgcaccctct gtacctgtca ctcctggaga gtcagtatcc    60
atctcctgca ggtctactaa gagtctcctg catagtaatg caacactta cttgtattgg   120 ttcctgcaga ggccaggcca gtctcctcag ctcctgatat atcggatgtc aaccttgcc   180 tcaggagtcc cagacaggtt cagtggcagt gggtcaggaa ctgctttcac actgagaatc   240
agtagagtgg aggctgagga tgtgggtgtt tattactgta tgcaacatct agaatatcct   300
ttcacgttcg gagggggac caagctggaa ataaaacggg ctgtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

<210> SEQ ID NO 49
<211> LENGTH: 217
<212> TYPE: PRT
<213> ORGANISM: Artificial Sequence
<220> FEATURE:
<223> OTHER INFORMATION: 25E9 light chain sequence

<400> SEQUENCE: 49

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
```

<210> SEQ ID NO 50
<211> LENGTH: 1422
<212> TYPE: DNA
<213> ORGANISM: Artificial Sequence
<220> FEATURE:
<223> OTHER INFORMATION: 25E9 heavy chain sequence

<400> SEQUENCE: 50

```
gagatccagc tgcagcagtc tggagttgag ctggtgaggc ctggggcttc agtgacgctg      60
tcctgcaagg cttcgggcta cacatttact gactatgaca tgcactgggt gaagcagaca     120
cctgttcatg gcctggaatg gattggaact attgatcctg aaactggtgg tactgcctac     180
aatcagaagt tcaagggcaa ggccacactg actgcggaca tcctccacac acagcctac     240
atggagctca gcagcctgac atctgaggac tctgccgtct attactgtac aagtttctac     300
tatacttact ctaattacga cgtggggttt gcttactggg gccaagggac tctggtcact     360
gtctctgcag cctcaactgg ggcgtcttat tactatgcta tggaccactg gggtcaagga     420
acctcagtca ccgtctcctc agcctcaacg aagggcccat cggtcttccc cctggcgccc     480
tgctccagga gcacctccga gcacagcc gccctgggct gcctggtcaa ggactacttc      540
cccgaaccgg tgacggtgtc gtggaactca ggcgctctga ccagcggcgt gcacaccttc     600
ccagctgtcc tacagtcctc aggactctac tccctcagca gcgtggtgac cgtgccctcc     660
agcaacttcg gcacccagac ctacacctgc aacgtagatc acaagcccag caacaccaag     720
gtggacaaga cagttgagcg caaatgttgt gtcgagtgcc caccgtgccc agcaccacct     780
gtggcaggac cgtcagtctt ccgcttcccc ccaaaaccca aggacacccg catgatctcc     840
cggacccctg aggtcacgtg cgtggtggtg gatgtgagc acgaagaccc cgaggtccag     900
ttcaactggt acgtggacgg cgtggaggtg cataatgcca agacaaagcc acgggaggag     960
cagttcaaca gcacgttccg tgtggtcagc gtcctcaccg ttgtgcacca ggactggctg    1020
aacggcaagg agtacaagtg caaggtctcc aacaaaggcc tcccagcccc catcgagaaa    1080
accatctcca aaaccaaagg gcagcccga gaaccacagg tgtacaccct gcccccatcc    1140
cgggaggaga tgaccaagaa ccaggtcagc ctgacctgcc tggtcaaagg cttctacccc    1200
agcgacatcg ccgtggagtg ggagagcaat gggcagccgg agaacaacta caagaccaca    1260
cctcccatgc tggactccga cggctccttc ttcctctaca gcaagctcac cgtggacaag    1320
agcaggtggc agcaggggaa cgtcttctca tgctccgtga tgcatgaggc tctgcacaac    1380
cactacacgc agaagagcct ctccctgtct ccgggtaaat ga                       1422
```

<210> SEQ ID NO 51
<211> LENGTH: 449
<212> TYPE: PRT
<213> ORGANISM: Artificial Sequence
<220> FEATURE:
<223> OTHER INFORMATION: 25E9 heavy chain sequence

<400> SEQUENCE: 51

Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe

```
                50                  55                  60
Lys Gly Lys Ala Thr Leu Thr Ala Asp Arg Ser Ser Thr Thr Ala Tyr
 65                  70                  75                  80

Met Glu Leu Ser Ser Leu Thr Ser Glu Asp Ser Ala Val Tyr Tyr Cys
                 85                  90                  95

Thr Ser Phe Tyr Tyr Thr Tyr Ser Asn Tyr Asp Val Gly Phe Ala Tyr
                100                 105                 110

Trp Gly Gln Gly Thr Leu Val Thr Val Ser Ala Ala Ser Thr Lys Gly
                115                 120                 125

Pro Ser Val Phe Pro Leu Ala Pro Cys Ser Arg Ser Thr Ser Glu Ser
130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Asn Phe Gly Thr Gln Thr Tyr Thr Cys Asn Val
                195                 200                 205

Asp His Lys Pro Ser Asn Thr Lys Val Asp Lys Thr Val Glu Arg Lys
                210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Phe Asn Ser Thr Phe Arg Val
                290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
                325                 330                 335

Thr Ile Ser Lys Thr Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 52
<211> LENGTH: 318
<212> TYPE: DNA
```

<213> ORGANISM: Artificial Sequence
<220> FEATURE:
<223> OTHER INFORMATION: 25A1 light chain variable region sequence

<400> SEQUENCE: 52

```
gaaaatgtgc tcacccagtc tccagcaatc atgtctgcat ctccagggga gaaggtcacc    60
atatcctgca gtgccagctc aagtgtaagt tacatgtact ggtaccagca gaagccagga   120
tcctccccca aaccctggat ttatcgcaca tccaacctgg cttctggagt ccctgctcgc   180
ttcagtggca gtgggtctgg gacctcttac tctctcacaa tcagcagcat ggaggctgaa   240
gatgctgcca cttattactg ccagcagtgg agtagtaacc cactcacgtt cggtgctggg   300
accaagctgg agctgaaa                                                 318
```

<210> SEQ ID NO 53
<211> LENGTH: 106
<212> TYPE: PRT
<213> ORGANISM: Artificial Sequence
<220> FEATURE:
<223> OTHER INFORMATION: 25A1 light chain variable region sequence

<400> SEQUENCE: 53

```
Glu Asn Val Leu Thr Gln Ser Pro Ala Ile Met Ser Ala Ser Pro Gly
 1               5                  10                  15
Glu Lys Val Thr Ile Ser Cys Ser Ala Ser Ser Val Ser Tyr Met
            20                  25                  30
Tyr Trp Tyr Gln Gln Lys Pro Gly Ser Ser Pro Lys Pro Trp Ile Tyr
        35                  40                  45
Arg Thr Ser Asn Leu Ala Ser Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Ser Asn Pro Leu Thr
                85                  90                  95
Phe Gly Ala Gly Thr Lys Leu Glu Leu Lys
            100                 105
```

<210> SEQ ID NO 54
<211> LENGTH: 372
<212> TYPE: DNA
<213> ORGANISM: Artificial Sequence
<220> FEATURE:
<223> OTHER INFORMATION: 25A1 heavy chain variable region sequence

<400> SEQUENCE: 54

```
gaggtccagc tgcaacaatc tgggactgag ctggtgaggc ctgggtcctc agtgaagatt    60
tcctgcaagg cttctggcta caccttcacc aggtactgga tggactgggt gaagcagagg   120
cctggacaag gccttgagtg gatcggagag attgatcctt ctgatagtta tactaactac   180
aatcaaaagt tcaagggcaa ggccacattg actgtagata aattctccag aacagcctat   240
atggaactca gcagcctgac atctgaggac tctgcggtct attactgtgc aagatcgggg   300
gcctactcta gtgactatag ttacgacggg tttgcttact ggggccaagg gactctggtc   360
actgtctctg ca                                                       372
```

<210> SEQ ID NO 55
<211> LENGTH: 124
<212> TYPE: PRT
<213> ORGANISM: Artificial Sequence
<220> FEATURE:
<223> OTHER INFORMATION: 25A1 heavy chain variable region sequence

<400> SEQUENCE: 55

Glu Val Gln Leu Gln Gln Ser Gly Thr Glu Leu Val Arg Pro Gly Ser
1               5                   10                  15

Ser Val Lys Ile Ser Cys Lys Ala Ser Gly Tyr Thr Phe Thr Arg Tyr
            20                  25                  30

Trp Met Asp Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
50                  55                  60

Lys Gly Lys Ala Thr Leu Thr Val Asp Lys Phe Ser Arg Thr Ala Tyr
65                  70                  75                  80

Met Glu Leu Ser Ser Leu Thr Ser Glu Asp Ser Ala Val Tyr Tyr Cys
                85                  90                  95

Ala Arg Ser Gly Ala Tyr Ser Ser Asp Tyr Tyr Asp Gly Phe Ala
            100                 105                 110

Tyr Trp Gly Gln Gly Thr Leu Val Thr Val Ser Ala
        115                 120

<210> SEQ ID NO 56
<211> LENGTH: 336
<212> TYPE: DNA
<213> ORGANISM: Artificial Sequence
<220> FEATURE:
<223> OTHER INFORMATION: 25B4 light chain variable region sequence

<400> SEQUENCE: 56
gatattgtga tgacccaggc tgcattctcc aatccagtca ctcttggaac atcagcttcc    60
atctcctgca ggtctagtaa gagtctccta catagtaatg gcatcactta tttgtattgg   120
tatctgcaga agccaggcca gtctcctcag ctcctgattt atcagatgtc caaccttgcc   180
tcaggagtcc cagacaggtt cagtggcagt gggtcaggaa ctgctttcac actgagaatc   240
agtagagtgg aggctgagga tgtgggtgtt tattactgta tgcaacatct agaatatccg   300
tacacgttcg gaggggggac caagctggaa ataaaa                             336

<210> SEQ ID NO 57
<211> LENGTH: 112
<212> TYPE: PRT
<213> ORGANISM: Artificial Sequence
<220> FEATURE:
<223> OTHER INFORMATION: 25B4 light chain variable region sequence

<400> SEQUENCE: 57

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 58
<211> LENGTH: 354
<212> TYPE: DNA
<213> ORGANISM: Artificial Sequence
<220> FEATURE:
<223> OTHER INFORMATION: 25B4 heavy chain variable region sequence

<400> SEQUENCE: 58

```
caggtccaag tgcagcagcc tggggctgaa attgtgaggc ctggggcttc agtgaagctg      60
tcctgcaagg cttctggcta caccttcacc agctactgga tgcactgggt gaagcagagg     120
cctggacaag ccttgagtg gattggactg attaatccta ccaacggtcg tactaactac     180
aatgagaagt tcaagagcaa ggccacactg actgtagaca atcctccag cacagcctac     240 atgcaactca gcagcctgac atctgaggac tctgcggtct attactgtgc aagagggggg     300
gacggggact actttgacta ctggggccaa ggcaccactc tcacagtctc ctca           354
```

<210> SEQ ID NO 59
<211> LENGTH: 118
<212> TYPE: PRT
<213> ORGANISM: Artificial Sequence
<220> FEATURE:
<223> OTHER INFORMATION: 25B4 heavy chain variable region sequence

<400> SEQUENCE: 59

```
Gln Val Gln Val Gln Gln Pro Gly Ala Glu Ile Val Arg Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Thr Asn Gly Arg Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Asp Gly Asp Tyr Phe Asp Tyr Trp Gly Gln Gly Thr
            100                 105                 110

Thr Leu Thr Val Ser Ser
        115
```

<210> SEQ ID NO 60
<211> LENGTH: 336
<212> TYPE: DNA
<213> ORGANISM: Artificial Sequence
<220> FEATURE:
<223> OTHER INFORMATION: 25B8 light chain variable region sequence

<400> SEQUENCE: 60

```
gatattgtga tgacccaggc tgcaccctct gtacctgtca ctcctggaga gtcagtatcc      60
atctcctgca ggtctactaa gagtctcctg catagtaatg caacactta cttgtattgg     120 ttcctgcaga ggccaggcca gtctcctcag ctcctgatat atcggatgtc aaccttgcc     180 tcaggagtcc cagacaggtt cagtggcagt gggtcaggaa ctgctttcac actgagaatc     240
agtagagtgg aggctgagga tgtgggtgtt tattactgta tgcaacatct agaatatcct     300
ttcacgttcg agggggggac caagctggaa ataaaa                              336
```

<210> SEQ ID NO 61

```
<211> LENGTH: 112
<212> TYPE: PRT
<213> ORGANISM: Artificial Sequence
<220> FEATURE:
<223> OTHER INFORMATION: 25B8 light chain variable region sequence

<400> SEQUENCE: 61
```

Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

```
<210> SEQ ID NO 62
<211> LENGTH: 369
<212> TYPE: DNA
<213> ORGANISM: Artificial Sequence
<220> FEATURE:
<223> OTHER INFORMATION: 25B8 heavy chain variable region sequence

<400> SEQUENCE: 62
```

| | |
|---|---|
| gagatccagc tgcagcagtc tggagttgag ctggtgaggc ctggggcttc agtgacgctg | 60 |
| tcctgcaagg cttcgggcta cacatttact gactatgaca tgcactgggt gaagcagaca | 120 |
| cctgttcatg gcctggaatg gattggaact attgatcctg aaactggtgg tactgcctac | 180 |
| aatcagaagt tcaagggcaa ggccacactg actgcggaca tcctccac acagcctac | 240 |
| atggagctca gcagcctgac atctgaggac tctgccgtct attactgtac aactttctac | 300 |
| tatagtcact ataattacga cgtggggttt gcttactggg gccaagggac tctggtcact | 360 |
| gtctctgca | 369 |

```
<210> SEQ ID NO 63
<211> LENGTH: 123
<212> TYPE: PRT
<213> ORGANISM: Artificial Sequence
<220> FEATURE:
<223> OTHER INFORMATION: 25B8 heavy chain variable region sequence

<400> SEQUENCE: 63
```

Glu Ile Gln Leu Gln Gln Ser Gly Val Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
        35                  40                  45

Gly Thr Ile Asp Pro Glu Thr Gly Gly Thr Ala Tyr Asn Gln Lys Phe
    50                  55                  60

Lys Gly Lys Ala Thr Leu Thr Ala Asp Arg Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Thr Thr Phe Tyr Tyr Ser His Tyr Asn Tyr Asp Val Gly Phe Ala Tyr
            100                 105                 110

Trp Gly Gln Gly Thr Leu Val Thr Val Ser Ala
            115                 120

<210> SEQ ID NO 64
<211> LENGTH: 336
<212> TYPE: DNA
<213> ORGANISM: Artificial Sequence
<220> FEATURE:
<223> OTHER INFORMATION: 25C1 light chain variable region sequence

<400> SEQUENCE: 64
gatattgtga tgacccaggc tgcaccctct gtacctgtca ctcctggaga gtcagtatcc      60
atctcctgca ggtctagtaa gagtctcctg catagtaatg caacactta cttgtattgg     120 ttcctgcaga ggccaggcca gtcccctcag ctcctgatat atcggatgtc aaccttgcc     180 tcaggagtcc cagacaggtt cagtggcagt gggtcaggaa ctgctttcac actgagaatc    240
agtagagtgg aggctgagga tgtgggtgtt tattactgta tgcaacatct agaatatcct    300
ttcacgttcg ggggggggac caagctggaa ataaaa                              336

<210> SEQ ID NO 65
<211> LENGTH: 112
<212> TYPE: PRT
<213> ORGANISM: Artificial Sequence
<220> FEATURE:
<223> OTHER INFORMATION: 25C1 light chain variable region sequence

<400> SEQUENCE: 65

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110

<210> SEQ ID NO 66
<211> LENGTH: 369
<212> TYPE: DNA
<213> ORGANISM: Artificial Sequence
<220> FEATURE:
<223> OTHER INFORMATION: 25C1 heavy chain variable region sequence

<400> SEQUENCE: 66
gagatccagc tgcagcagtc tggagctgag ctggtgaggc ctggggcttc agtgacgctg     60
tcctgcaagg cttcgggcta cacatttact gactatgaaa tgcactgggt gaagcagaca    120
cctgttcatg gcctggaatg gattggagct attgatcctg aaactggtgg tactgcctac    180
aatcagaagt tcaagggcaa ggccacactg actgcagaca atcctccag cacagcctac    240 atggagctca gcagcctgac atctgaggac tctgccgtct attactgtac aagtttctac    300

```
tatacttact ataattacga cgtggggttt gcttactggg gccaagggac tctggtcact    360
gtctctgca                                                            369
```

<210> SEQ ID NO 67
<211> LENGTH: 123
<212> TYPE: PRT
<213> ORGANISM: Artificial Sequence
<220> FEATURE:
<223> OTHER INFORMATION: 25C1 heavy chain variable region sequence

<400> SEQUENCE: 67

```
Glu Ile Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Thr Leu Thr Ala Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Tyr Asn Tyr Asp Val Gly Phe Ala Tyr
            100                 105                 110

Trp Gly Gln Gly Thr Leu Val Thr Val Ser Ala
        115                 120
```

<210> SEQ ID NO 68
<211> LENGTH: 336
<212> TYPE: DNA
<213> ORGANISM: Artificial Sequence
<220> FEATURE:
<223> OTHER INFORMATION: 25D8 light chain variable region sequence

<400> SEQUENCE: 68

```
gatattgtga tgacccaggc tgcattctcc aatccagtca ctcttggaac atcagcttcc     60
atctcctgca ggtctagtaa gagtctccta catagtaatg gcatcactta tttgtattgg    120
tatctgcaga agccaggcca gtctcctcag ctcctgattt atcagatgtc caaccttgcc    180
tcaggagtcc cagacaggtt cagtagcagt gggtcaggaa ctgatttcac actgagaatc    240
agcagagtgg aggctgagga tgtgggtgtt tattactgtg ctcaaaatct agaacttccg    300
tacacgttcg gaggggggac caagctggaa ataaaa                              336
```

<210> SEQ ID NO 69
<211> LENGTH: 112
<212> TYPE: PRT
<213> ORGANISM: Artificial Sequence
<220> FEATURE:
<223> OTHER INFORMATION: 25D8 light chain variable region sequence

<400> SEQUENCE: 69

```
Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
```

```
                50                  55                  60
Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Tyr Thr Phe Gly Gly Gly Thr Lys Leu Glu Ile Lys
            100                 105                 110

<210> SEQ ID NO 70
<211> LENGTH: 354
<212> TYPE: DNA
<213> ORGANISM: Artificial Sequence
<220> FEATURE:
<223> OTHER INFORMATION: 25D8 heavy chain variable region sequence

<400> SEQUENCE: 70
caggtccaag tgcagcagcc tggggctgag cttgtgaagc ctggggcttc ggtgaagctg      60
tcctgcaagg cttctggcta caccttcacc agctactgga tgcactgggt gaagcagagg     120
cctggacaag gccttgagtg gattggactg attaatccta gcaacgctcg tactaactac     180
aatgagaagt tcaataccaa ggccacactg actgtagaca atcctccag cacagcctac      240 atgcaactca gcagcctgac atctgaggac tctgcggtct attactgtgc aagaggggggg    300 gacgggggact actttgacta ctggggccaa ggcaccactc tcacagtctc ctca          354

<210> SEQ ID NO 71
<211> LENGTH: 118
<212> TYPE: PRT
<213> ORGANISM: Artificial Sequence
<220> FEATURE:
<223> OTHER INFORMATION: 25D8 heavy chain variable region sequence

<400> SEQUENCE: 71

Gln Val Gln Val Gln Gln Pro Gly Ala Glu Leu Val Lys Pro Gly Ala
 1               5                  10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Leu Ile Asn Pro Ser Asn Ala Arg Thr Asn Tyr Asn Glu Lys Phe
    50                  55                  60

Asn Thr Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Gly Gly Asp Gly Asp Tyr Phe Asp Tyr Trp Gly Gln Gly Thr
            100                 105                 110

Thr Leu Thr Val Ser Ser
        115

<210> SEQ ID NO 72
<211> LENGTH: 318
<212> TYPE: DNA
<213> ORGANISM: Artificial Sequence
<220> FEATURE:
<223> OTHER INFORMATION: 25E5 light chain variable region sequence

<400> SEQUENCE: 72
caaattgttc tcacccagtc tccaacactc atgtctgcat ctccagggga gaaggtcacc      60
atgacctgca gtgccagctc aagtgtaagt tacatgtact ggtaccagca gaagccaaga    120
```

```
tcctcccca aaccctggat ttatcgcaca tccaacctgg tttctggagt ccctgtacgc    180
ttcagtggca gtgggtctgg gacctcttac tctctcacaa tcagcagcat ggaggctgaa    240
gatgctgcca cttattactg ccagcagtgg agtagtaacc cacccacgtt cggtgctggg    300
accaagctgg agctgaaa                                                   318
```

<210> SEQ ID NO 73
<211> LENGTH: 106
<212> TYPE: PRT
<213> ORGANISM: Artificial Sequence
<220> FEATURE:
<223> OTHER INFORMATION: 25E5 light chain variable region sequence

<400> SEQUENCE: 73

```
Gln Ile Val Leu Thr Gln Ser Pro Thr Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Arg Thr Ser Asn Leu Val Ser Gly Val Pro Val Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ala Gly Thr Lys Leu Glu Leu Lys
            100                 105
```

<210> SEQ ID NO 74
<211> LENGTH: 360
<212> TYPE: DNA
<213> ORGANISM: Artificial Sequence
<220> FEATURE:
<223> OTHER INFORMATION: 25E5 heavy chain variable region sequence

<400> SEQUENCE: 74

```
gaagtgaagc ttgaggagtc tggaggtggc ctggtgcagc ctggaggatc cctgaaactc    60
tcctgtgcag cctcaggatt cgattttagt aaagactgga tgagttgggt ccggcaggct    120
ccagggaaag gctagaatg gattggagaa attaatccag atagcagtac gataaactat    180
gcaccatctc ttaaggataa attcatcatc tccagagaga cgccaaaaa tacgctgtac    240 ctgcaaatga gcaaagtgag atctgaggac acagcccttt attactgttc aagactagag    300
gactacgaag actggtactt cgatgtctgg ggcgcaggga ccacggtcac cgtctcctca    360
```

<210> SEQ ID NO 75
<211> LENGTH: 120
<212> TYPE: PRT
<213> ORGANISM: Artificial Sequence
<220> FEATURE:
<223> OTHER INFORMATION: 25E5 heavy chain variable region sequence

<400> SEQUENCE: 75

```
Glu Val Lys Leu Glu Glu Ser Gly Gly Gly Leu Val Gln Pro Gly Gly
1               5                   10                  15

Ser Leu Lys Leu Ser Cys Ala Ala Ser Gly Phe Asp Phe Ser Lys Asp
            20                  25                  30

Trp Met Ser Trp Val Arg Gln Ala Pro Gly Lys Gly Leu Glu Trp Ile
        35                  40                  45
```

Gly Glu Ile Asn Pro Asp Ser Ser Thr Ile Asn Tyr Ala Pro Ser Leu
            50                  55                  60

Lys Asp Lys Phe Ile Ile Ser Arg Glu Asn Ala Lys Asn Thr Leu Tyr
 65                  70                  75                  80

Leu Gln Met Ser Lys Val Arg Ser Glu Asp Thr Ala Leu Tyr Tyr Cys
                85                  90                  95

Ser Arg Leu Glu Asp Tyr Glu Asp Trp Tyr Phe Asp Val Trp Gly Ala
            100                 105                 110

Gly Thr Thr Val Thr Val Ser Ser
            115                 120

<210> SEQ ID NO 76
<211> LENGTH: 321
<212> TYPE: DNA
<213> ORGANISM: Artificial Sequence
<220> FEATURE:
<223> OTHER INFORMATION: 25E6 light chain variable region sequence

<400> SEQUENCE: 76
agtattgtga tgacccagac tcccaaattc ctgcttgtat cagcaggaga cagggttacc      60
ataacctgca aggccagtca gagtgtgagt aatgctgtag cttggtacca acagaagcca     120
gggcagtctc ctaaactgct gatatactat acatccaatc gctacactgg agtccctgat     180
cgcttcactg gcagtggata tgggacggat ttcactttca ccatcaccac tgtgcaggct     240
gaagacctgg cagtttattt ctgtcagcag gattatacct ctccgtggac gttcggtgga     300
ggcaccaagc tggaaatcaa a                                               321

<210> SEQ ID NO 77
<211> LENGTH: 107
<212> TYPE: PRT
<213> ORGANISM: Artificial Sequence
<220> FEATURE:
<223> OTHER INFORMATION: 25E6 light chain variable region sequence

<400> SEQUENCE: 77

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Ser Asn Ala
            20                  25                  30

Val Ala Trp Tyr Gln Gln Lys Pro Gly Gln Ser Pro Lys Leu Leu Ile
        35                  40                  45

Tyr Tyr Thr Ser Asn Arg Tyr Thr Gly Val Pro Asp Arg Phe Thr Gly
    50                  55                  60

Ser Gly Tyr Gly Thr Asp Phe Thr Phe Thr Ile Thr Thr Val Gln Ala
 65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Lys
            100                 105

<210> SEQ ID NO 78
<211> LENGTH: 336
<212> TYPE: DNA
<213> ORGANISM: Artificial Sequence
<220> FEATURE:
<223> OTHER INFORMATION: 25E6 heavy chain variable region sequence

<400> SEQUENCE: 78
caggtccaac tgcagcagcc tggggctgaa ctggcgaagc ctggggcttc agtgaagttg      60

```
tcctgcaagg cttctggcta caccttcaac acctataata tgtactggtt gaaacagagg    120
cctgggcaag gccttgagtg gattgggggg attgatccta gcaatggtga tactaaaatc    180
aatgagaagt tcaagaacaa ggccacactg actgttgaca atcctccag tacagcctat     240 atgcaactca gcggcctgac atctgaggac tctgcggtct attactgtac aagccatacg    300
tactggggcc aagggactct ggtcactgtc tctgca                              336
```

<210> SEQ ID NO 79
<211> LENGTH: 112
<212> TYPE: PRT
<213> ORGANISM: Artificial Sequence
<220> FEATURE:
<223> OTHER INFORMATION: 25E6 heavy chain variable region sequence
<400> SEQUENCE: 79

```
Gln Val Gln Leu Gln Gln Pro Gly Ala Glu Leu Ala Lys Pro Gly Ala
1               5                   10                  15

Ser Val Lys Leu Ser Cys Lys Ala Ser Gly Tyr Thr Phe Asn Thr Tyr
            20                  25                  30

Asn Met Tyr Trp Leu Lys Gln Arg Pro Gly Gln Gly Leu Glu Trp Ile
        35                  40                  45

Gly Gly Ile Asp Pro Ser Asn Gly Asp Thr Lys Ile Asn Glu Lys Phe
    50                  55                  60

Lys Asn Lys Ala Thr Leu Thr Val Asp Lys Ser Ser Thr Ala Tyr
65                  70                  75                  80

Met Gln Leu Ser Gly Leu Thr Ser Glu Asp Ser Ala Val Tyr Tyr Cys
                85                  90                  95

Thr Ser His Thr Tyr Trp Gly Gln Gly Thr Leu Val Thr Val Ser Ala
            100                 105                 110
```

<210> SEQ ID NO 80
<211> LENGTH: 336
<212> TYPE: DNA
<213> ORGANISM: Artificial Sequence
<220> FEATURE:
<223> OTHER INFORMATION: 25E9 light chain variable region sequence
<400> SEQUENCE: 80

```
gatattgtga tgacccaggc tgcaccctct gtacctgtca ctcctggaga gtcagtatcc    60
atctcctgca ggtctactaa gagtctcctg catagtaatg caacactta cttgtattgg   120 ttcctgcaga ggccaggcca gtctcctcag ctcctgatat atcggatgtc caaccttgcc   180
tcaggagtcc cagacaggtt cagtggcagt gggtcaggaa ctgctttcac actgagaatc    240
agtagagtgg aggctgagga tgtgggtgtt tattactgta tgcaacatct agaatatcct   300
ttcacgttcg gaggggggac caagctggaa ataaaa                             336
```

<210> SEQ ID NO 81
<211> LENGTH: 112
<212> TYPE: PRT
<213> ORGANISM: Artificial Sequence
<220> FEATURE:
<223> OTHER INFORMATION: 25E9 light chain variable region sequence
<400> SEQUENCE: 81

```
Asp Ile Val Met Thr Gln Ala Ala Pro Ser Val Pro Val Thr Pro Gly
1               5                   10                  15

Glu Ser Val Ser Ile Ser Cys Arg Ser Thr Lys Ser Leu Leu His Ser
            20                  25                  30
```

```
Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
 50                  55                  60

Asp Arg Phe Ser Gly Ser Gly Ser Gly Thr Ala Phe Thr Leu Arg Ile
 65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Gly Gly Thr Lys Leu Glu Ile Lys
            100                 105                 110
```

<210> SEQ ID NO 82
<211> LENGTH: 369
<212> TYPE: DNA
<213> ORGANISM: Artificial Sequence
<220> FEATURE:
<223> OTHER INFORMATION: 25E9 heavy chain variable region sequence

<400> SEQUENCE: 82

```
gagatccagc tgcagcagtc tggagttgag ctggtgaggc ctggggcttc agtgacgctg      60
tcctgcaagg cttcgggcta cacatttact gactatgaca tgcactgggt gaagcagaca     120
cctgttcatg gcctggaatg gattggaact attgatcctg aaactggtgg tactgcctac     180
aatcagaagt tcaagggcaa ggccacactg actgcggaca tcctccacac acagcctac     240
atggagctca gcagcctgac atctgaggac tctgccgtct attactgtac aagtttctac     300
tatacttact ctaattacga cgtggggttt gcttactggg ccaagggac tctggtcact     360
gtctctgca                                                             369
```

<210> SEQ ID NO 83
<211> LENGTH: 123
<212> TYPE: PRT
<213> ORGANISM: Artificial Sequence
<220> FEATURE:
<223> OTHER INFORMATION: 25E9 heavy chain variable region sequence

<400> SEQUENCE: 83

```
Glu Ile Gln Leu Gln Gln Ser Gly Val Glu Leu Val Arg Pro Gly Ala
 1               5                  10                  15

Ser Val Thr Leu Ser Cys Lys Ala Ser Gly Tyr Thr Phe Thr Asp Tyr
            20                  25                  30

Asp Met His Trp Val Lys Gln Thr Pro Val His Gly Leu Glu Trp Ile
            35                  40                  45

Gly Thr Ile Asp Pro Glu Thr Gly Gly Thr Ala Tyr Asn Gln Lys Phe
 50                  55                  60

Lys Gly Lys Ala Thr Leu Thr Ala Asp Arg Ser Ser Thr Thr Ala Tyr
 65                  70                  75                  80

Met Glu Leu Ser Ser Leu Thr Ser Glu Asp Ser Ala Val Tyr Tyr Cys
                85                  90                  95

Thr Ser Phe Tyr Tyr Thr Tyr Ser Asn Tyr Asp Val Gly Phe Ala Tyr
            100                 105                 110

Trp Gly Gln Gly Thr Leu Val Thr Val Ser Ala
            115                 120
```

<210> SEQ ID NO 84
<211> LENGTH: 50
<212> TYPE: DNA
<213> ORGANISM: Artificial Sequence
<220> FEATURE:
<223> OTHER INFORMATION: primer OGS1773

<400> SEQUENCE: 84
gtaagcgcta gcgcctcaac gaagggccca tctgtctttc ccctggcccc    50

<210> SEQ ID NO 85
<211> LENGTH: 37
<212> TYPE: DNA
<213> ORGANISM: Artificial Sequence
<220> FEATURE:
<223> OTHER INFORMATION: primer OGS1774

<400> SEQUENCE: 85
gtaagcgaat tcacaagatt tgggctcaac tttcttg    37

<210> SEQ ID NO 86
<211> LENGTH: 321
<212> TYPE: DNA
<213> ORGANISM: Homo sapiens

<400> SEQUENCE: 86
gctgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgcccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g    321

<210> SEQ ID NO 87
<211> LENGTH: 106
<212> TYPE: PRT
<213> ORGANISM: Homo sapiens

<400> SEQUENCE: 87

Ala Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 88
<211> LENGTH: 6385
<212> TYPE: DNA
<213> ORGANISM: Artificial Sequence
<220> FEATURE:
<223> OTHER INFORMATION: expression plasmid pTTVK1

<400> SEQUENCE: 88
cttgagccgg cggatggtcg aggtgaggtg tggcaggctt gagatccagc tgttggggtg    60
agtactccct ctcaaaagcg ggcattactt ctgcgctaag attgtcagtt tccaaaaacg   120

```
aggaggattt gatattcacc tggcccgatc tggccataca cttgagtgac aatgacatcc    180
actttgcctt tctctccaca ggtgtccact cccaggtcca agtttaaacg gatctctagc    240
gaattcatga actttctgct gtcttgggtg cattggagcc ttgccttgct gctctacctc    300
caccatgcca agtggtccca ggcttgagac ggagcttaca cgcgctgtgg ctgcaccatct   360 gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc     600 gaagtcaccc atcagggcct gagctcgccc gtcacaaaga gcttcaacag gggagagtgt    660
tagggtaccg cggccgcttc gaatgagatc ccccgacctc gacctctggc taataaagga    720
aatttatttt cattgcaata gtgtgttgga attttttgtg tctctcactc ggaaggacat    780
atgggagggc aaatcatttg gtcgagatcc ctcggagatc tctagctaga gccccgccgc    840
cggacgaact aaacctgact acggcatctc tgccccttct tcgcggggca gtgcatgtaa    900
tcccttcagt tggttggtac aacttgccaa ctgggccctg ttccacatgt gacacggggg    960
gggaccaaac acaaggggt tctctgactg tagttgacat cctatataaat ggatgtgcac    1020 atttgccaac actgagtggc tttcatcctg gagcagactt tgcagtctgt ggactgcaac   1080
acaacattgc ctttatgtgt aactcttggc tgaagctctt acaccaatgc tgggggacat   1140
gtacctccca ggggcccagg aagactacgg gaggctacac caacgtcaat cagaggggcc   1200
tgtgtagcta ccgataagcg gaccctcaag agggcattag caatagtgtt tataaggccc   1260
ccttgttaac cctaaacggg tagcatatgc ttcccgggta gtagtatata ctatccagac   1320
taaccctaat tcaatagcat atgttaccca acgggaagca tatgctatcg aattagggtt   1380
agtaaaaggg tcctaaggaa cagcgatatc tcccacccca tgagctgtca cggttttatt   1440 tacatgggt caggattcca cgagggtagt gaaccatttt agtcacaagg gcagtggctg    1500
aagatcaagg agcgggcagt gaactctcct gaatcttcgc ctgcttcttc attctccttc   1560
gtttagctaa tagaataact gctgagttgt gaacagtaag gtgtatgtga ggtgctcgaa   1620
aacaaggttt caggtgacgc ccccagaata aaatttggac gggggggttca gtggtggcat   1680 tgtgctatga caccaatata accctcacaa acccccttggg caataaatac tagtgtagga   1740
atgaaacatt ctgaatatct ttaacaatag aaatccatgg ggtggggaca agccgtaaag   1800
actggatgtc catctcacac gaatttatgg ctatgggcaa cacataatcc tagtgcaata   1860
tgatactggg gttattaaga gtgtgtcccag gcagggacca agacaggtga accatgttgt   1920
tacactctat ttgtaacaag gggaaagaga gtggacgccg acagcagcgg actccactgg   1980
ttgtctctaa cacccccgaa aattaaacgg ggctccacgc caatgggcc cataaacaaa    2040 gacaagtggc cactctttt tttgaaattg tggagtgggg gcacgcgtca gccccacac    2100 gccgccctgc ggttttggac tgtaaaataa gggtgtaata acttggctga ttgtaacccc   2160
gctaaccact gcggtcaaac cacttgccca caaaaccact aatggcaccc cggggaatac   2220
ctgcataagt aggtgggcgg gccaagatag gggcgcgatt gctgcgatct ggaggacaaa   2280
ttacacacac ttgcgcctga gcgccaagca cagggttgtt ggtcctcata ttcacgaggt   2340
cgctgagagc acggtgggct aatgttgcca tgggtagcat atactaccca aatatctgga   2400
tagcatatgc tatcctaatc tatatctggg tagcataggc tatcctaatc tatatctggg   2460
tagcatatgc tatcctaatc tatatctggg tagtatatgc tatcctaatt tatatctggg   2520
```

```
tagcataggc tatcctaatc tatatctggg tagcatatgc tatcctaatc tatatctggg   2580
tagtatatgc tatcctaatc tgtatccggg tagcatatgc tatcctaata gagattaggg   2640
tagtatatgc tatcctaatt tatatctggg tagcatatac tacccaaata tctggatagc   2700
atatgctatc ctaatctata tctgggtagc atatgctatc ctaatctata tctgggtagc   2760
ataggctatc ctaatctata tctgggtagc atatgctatc ctaatctata tctgggtagt   2820
atatgctatc ctaatttata tctgggtagc ataggctatc ctaatctata tctgggtagc   2880
atatgctatc ctaatctata tctgggtagt atatgctatc ctaatctgta tccgggtagc   2940
atatgctatc ctcacgatga taagctgtca aacatgagaa ttaattcttg aagacgaaag   3000
ggcctcgtga tacgcctatt tttataggtt aatgtcatga taataatggt tcttagacg    3060 tcaggtggca cttttcgggg aaatgtgcgc ggaacccta tttgtttatt tttctaaata    3120
cattcaaata tgtatccgct catgagacaa taaccctgat aaatgcttca ataatattga   3180
aaaaggaaga gtatgagtat tcaacatttc cgtgtcgccc ttattccctt ttttgcggca   3240
ttttgccttc ctgttttttgc tcacccagaa acgctggtga agtaaaaga tgctgaagat   3300 cagttgggtg cacgagtggg ttacatcgaa ctggatctca acagcggtaa gatccttgag   3360
agttttcgcc ccgaagaacg ttttccaatg atgagcactt ttaaagttct gctatgtggc   3420
gcggtattat cccgtgttga cgccgggcaa gagcaactcg gtcgccgcat acactattct   3480
cagaatgact tggttgagta ctcaccagtc acagaaaagc atcttacgga tggcatgaca   3540
gtaagagaat tatgcagtgc tgccataacc atgagtgata acactgcggc caacttactt   3600
ctgacaacga tcggaggacc gaaggagcta accgcttttt tgcacaacat ggggggatcat  3660 gtaactcgcc ttgatcgttg ggaaccggag ctgaatgaag ccataccaaa cgacgagcgt   3720
gacaccacga tgcctgcagc aatggcaaca acgttgcgca aactattaac tggcgaacta   3780
cttactctag cttcccggca acaattaata gactggatgg aggcggataa agttgcagga   3840
ccacttctgc gctcggccct tccggctggc tggtttattg ctgataaatc tggagccggt   3900
gagcgtgggt ctcgcggtat cattgcagca ctggggccag atggtaagcc ctcccgtatc   3960
gtagttatct acacgacggg gagtcaggca actatgatga acgaaatag acagatcgct    4020 gagataggtg cctcactgat taagcattgg taactgtcag accaagttta ctcatatata   4080
ctttagattg atttaaaact tcattttttaa tttaaaagga tctaggtgaa gatcctttt   4140 gataatctca tgaccaaaat cccttaacgt gagttttcgt tccactgagc gtcagacccc   4200
gtagaaaaga tcaaaggatc ttcttgagat cctttttttc tgcgcgtaat ctgctgcttg   4260
caaacaaaaa aaccaccgct accagcggtg gtttgtttgc cggatcaaga gctaccaact   4320 cttttttccga aggtaactgg cttcagcaga gcgcagatac caaatactgt ccttctagtg   4380
tagccgtagt taggccacca cttcaagaac tctgtagcac cgcctacata cctcgctctg   4440
ctaatcctgt taccagtggc tgctgccagt ggcgataagt cgtgtcttac cgggttggac   4500
tcaagacgat agttaccgga taaggcgcag cggtcgggct gaacggggg ttcgtgcaca    4560 cagcccagct tggagcgaac gacctacacc gaactgagat acctacagcg tgagcattga   4620
gaaagcgcca cgcttcccga agggagaaag gcggacaggt atccggtaag cggcagggtc   4680
ggaacaggag agcgcacgag ggagcttcca ggggaaacg cctggtatct ttatagtcct    4740
gtcgggtttc gccacctctg acttgagcgt cgatttttgt gatgctcgtc aggggggcgg   4800
agcctatgga aaaacgccag caacgcggcc ttttacggt tcctggcctt ttgctggcct    4860
tttgctcaca tgttctttcc tgcgttatcc cctgattctg tggataaccg tattaccgcc   4920
```

-continued

```
tttgagtgag ctgataccgc tcgccgcagc cgaacgaccg agcgcagcga gtcagtgagc    4980
gaggaagcgg aagagcgccc aatacgcaaa ccgcctctcc ccgcgcgttg gccgattcat    5040
taatgcagct ggcacgacag gtttcccgac tggaaagcgg gcagtgagcg caacgcaatt    5100
aatgtgagtt agctcactca ttaggcaccc caggctttac actttatgct tccggctcgt    5160
atgttgtgtg gaattgtgag cggataacaa tttcacacag gaaacagcta tgaccatgat    5220
tacgccaagc tctagctaga ggtcgaccaa ttctcatgtt tgacagctta tcatcgcaga    5280
tccgggcaac gttgttgcat tgctgcaggc gcagaactgg taggtatggc agatctatac    5340
attgaatcaa tattggcaat tagccatatt agtcattggt tatatagcat aaatcaatat    5400
tggctattgg ccattgcata cgttgtatct atatcataat atgtacattt atattggctc    5460
atgtccaata tgaccgccat gttgacattg attattgact agttattaat agtaatcaat    5520
tacggggtca ttagttcata gcccatatat ggagttccgc gttacataac ttacggtaaa    5580
tggcccgcct ggctgaccgc ccaacgaccc cgcccattg acgtcaataa tgacgtatgt     5640
tcccatagta acgccaatag ggactttcca ttgacgtcaa tgggtggagt atttacggta    5700
aactgcccac ttggcagtac atcaagtgta tcatatgcca agtccgcccc ctattgacgt    5760
caatgacggt aaatggcccg cctggcatta tgcccagtac atgaccttac gggactttcc    5820
tacttggcag tacatctacg tattagtcat cgctattacc atggtgatgc ggttttggca    5880
gtacaccaat gggcgtggat agcggtttga ctcacgggga tttccaagtc tccaccccat    5940
tgacgtcaat gggagtttgt tttggcacca aaatcaacgg gactttccaa aatgtcgtaa    6000
taaccccgcc ccgttgacgc aaatgggcgg taggcgtgta cggtgggagg tctatataag    6060
cagagctcgt ttagtgaacc gtcagatcct cactctcttc cgcatcgctg tctgcgaggg    6120
ccagctgttg ggctcgcggt tgaggacaaa ctcttcgcgg tctttccagt actcttggat    6180
cggaaacccg tcggcctccg aacggtactc cgccaccgag ggacctgagc gagtccgcat    6240
cgaccggatc ggaaaacctc tcgagaaagg cgtctaacca gtcacagtcg caaggtaggc    6300
tgagcaccgt ggcgggcggc agcgggtggc ggtcggggtt gtttctggcg gaggtgctgc    6360
tgatgatgta attaaagtag gcggt                                          6385
```

```
<210> SEQ ID NO 89
<211> LENGTH: 43
<212> TYPE: DNA
<213> ORGANISM: Artificial Sequence
<220> FEATURE:
<223> OTHER INFORMATION: primer to introduce a VEGF A signal peptide in
      the 25A1 light chain

<400> SEQUENCE: 89
atgccaagtg gtcccaggct gaaaatgtgc tcacccagtc tcc                       43

<210> SEQ ID NO 90
<211> LENGTH: 43
<212> TYPE: DNA
<213> ORGANISM: Artificial Sequence
<220> FEATURE:
<223> OTHER INFORMATION: primer to introduce a VEGF A signal peptide in
      the 25B4, 25B8, 25C1, 25D8, and 25E9 light chains

<400> SEQUENCE: 90
atgccaagtg gtcccaggct gatattgtga tgacccaggc tgc                       43

<210> SEQ ID NO 91
<211> LENGTH: 43
<212> TYPE: DNA
```

<210> SEQ ID NO 91
<211> LENGTH: 43
<212> TYPE: DNA
<213> ORGANISM: Artificial Sequence
<220> FEATURE:
<223> OTHER INFORMATION: primer to introduce a VEGF A signal peptide in the 25E5 light chain

<400> SEQUENCE: 91

```
atgccaagtg gtcccaggct caaattgttc tcacccagtc tcc                43
```

<210> SEQ ID NO 92
<211> LENGTH: 43
<212> TYPE: DNA
<213> ORGANISM: Artificial Sequence
<220> FEATURE:
<223> OTHER INFORMATION: primer to introduce a VEGF A signal peptide in the 25E6 light chain

<400> SEQUENCE: 92

```
atgccaagtg gtcccaggct agtattgtga tgacccagac tcc                43
```

<210> SEQ ID NO 93
<211> LENGTH: 32
<212> TYPE: DNA
<213> ORGANISM: Artificial Sequence
<220> FEATURE:
<223> OTHER INFORMATION: reverse primer to amplify light chain variable regions

<400> SEQUENCE: 93

```
gggaagatga agacagatgg tgcagccaca gc                            32
```

<210> SEQ ID NO 94
<211> LENGTH: 50
<212> TYPE: DNA
<213> ORGANISM: Artificial Sequence
<220> FEATURE:
<223> OTHER INFORMATION: PCR primer OGS1769

<400> SEQUENCE: 94

```
gtaagcgcta gcgcctcaac gaagggccca tctgtctttc ccctggcccc         50
```

<210> SEQ ID NO 95
<211> LENGTH: 37
<212> TYPE: DNA
<213> ORGANISM: Artificial Sequence
<220> FEATURE:
<223> OTHER INFORMATION: PCR primer OGS1770

<400> SEQUENCE: 95

```
gtaagcgaat tcacaagatt tgggctcaac tttcttg                       37
```

<210> SEQ ID NO 96
<211> LENGTH: 309
<212> TYPE: DNA
<213> ORGANISM: Homo sapiens

<400> SEQUENCE: 96

```
gcctccacca agggcccatc ggtcttcccc ctggcaccct cctccaagag cacctctggg    60
ggcacagcag ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgt                                                           309
```

<210> SEQ ID NO 97
<211> LENGTH: 103
<212> TYPE: PRT
<213> ORGANISM: Homo sapiens

<400> SEQUENCE: 97

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

<210> SEQ ID NO 98
<211> LENGTH: 5367
<212> TYPE: DNA
<213> ORGANISM: Artificial Sequence
<220> FEATURE:
<223> OTHER INFORMATION: plasmid pYD19

<400> SEQUENCE: 98

| | | | | | |
|---|---|---|---|---|---|
| cttgagccgg | cggatggtcg | aggtgaggtg | tggcaggctt | gagatccagc | tgttggggtg | 60 |
| agtactccct | ctcaaaagcg | ggcattactt | ctgcgctaag | attgtcagtt | tccaaaaacg | 120 |
| aggaggattt | gatattcacc | tggcccgatc | tggccataca | cttgagtgac | aatgacatcc | 180 |
| actttgcctt | tctctccaca | ggtgtccact | cccaggtcca | agtttgccgc | caccatggag | 240 |
| acagacacac | tcctgctatg | ggtactgctg | ctctgggttc | caggttccac | tggcggagac | 300 |
| ggagcttacg | ggcccatcgg | tcttccccct | ggcgccctgc | tccaggagca | cctccgagag | 360 |
| cacagcggcc | ctgggctgcc | tggtcaagga | ctacttcccc | gaaccggtga | cggtgtcgtg | 420 |
| gaactcaggc | gctctgacca | gcggcgtgca | caccttccca | gctgtcctac | agtcctcagg | 480 |
| actctactcc | ctcagcagcg | tggtgaccgt | gccctccagc | aacttcggca | cccagaccta | 540 |
| cacctgcaac | gtagatcaca | agcccagcaa | caccaaggtg | gacaagacag | ttgagcgcaa | 600 |
| atgttgtgtc | gagtgcccac | cgtgcccagc | accacctgtg | gcaggaccgt | cagtcttcct | 660 |
| cttccccca | aaacccaagg | acaccctcat | gatctcccgg | acccctgagg | tcacgtgcgt | 720 |
| ggtggtggac | gtgagccacg | aagaccccga | ggtccagttc | aactggtacg | tggacggcgt | 780 |
| ggaggtgcat | aatgccaaga | caaagccacg | ggaggagcag | ttcaacagca | cgttccgtgt | 840 |
| ggtcagcgtc | ctcaccgttg | tgcaccagga | ctggctgaac | ggcaaggagt | acaagtgcaa | 900 |
| ggtctccaac | aaaggcctcc | cagccccat | cgagaaaacc | atctccaaaa | ccaaagggca | 960 |
| gccccgagaa | ccacaggtgt | acaccctgcc | cccatcccgg | gaggagatga | ccaagaacca | 1020 |
| ggtcagcctg | acctgcctgg | tcaaaggctt | ctaccccagc | gacatcgccg | tggagtggga | 1080 |
| gagcaatggg | cagccggaga | acaactacaa | gaccacacct | cccatgctgg | actccgacgg | 1140 |
| ctccttcttc | ctctacagca | agctcaccgt | ggacaagagc | aggtggcagc | aggggaacgt | 1200 |
| cttctcatgc | tccgtgatgc | atgaggctct | gcacaaccac | tacacgcaga | agagcctctc | 1260 |

```
cctgtctccc gggaaatgat cccccgacct cgacctctgg ctaataaagg aaatttattt    1320
tcattgcaat agtgtgttgg aattttttgt gtctctcact cggaaggaca tatgggaggg    1380
caaatcattt ggtcgagatc cctcggagat ctctagctag agccccgccg ccggacgaac    1440
taaacctgac tacggcatct ctgccccttc ttcgcgggc agtgcatgta atcccttcag    1500
ttggttggta caacttgcca actgaaccct aaacgggtag catatgcttc ccgggtagta    1560
gtatatacta tccagactaa ccctaattca atagcatatg ttacccaacg ggaagcatat    1620
gctatcgaat tagggttagt aaaagggtcc taaggaacag cgatgtaggt gggcgggcca    1680
agataggggc gcgattgctg cgatctggag gacaaattac acacacttgc gcctgagcgc    1740
caagcacagg gttgttggtc ctcatattca cgaggtcgct gagagcacgg tgggctaatg    1800
ttgccatggg tagcatatac tacccaaata tctggatagc atatgctatc ctaatctata    1860
tctgggtagc ataggctatc ctaatctata tctgggtagc atatgctatc ctaatctata    1920
tctgggtagt atatgctatc ctaatttata tctgggtagc ataggctatc ctaatctata    1980
tctgggtagc atatgctatc ctaatctata tctgggtagt atatgctatc ctaatctgta    2040
tccgggtagc atatgctatc ctaatagaga ttagggtagt atatgctatc ctaatttata    2100
tctgggtagc atatactacc caaatatctg gatagcatat gctatcctaa tctatatctg    2160
ggtagcatat gctatcctaa tctatatctg ggtagcatag gctatcctaa tctatatctg    2220
ggtagcatat gctatcctaa tctatatctg ggtagtatat gctatcctaa tttatatctg    2280
ggtagcatag gctatcctaa tctatatctg ggtagcatat gctatcctaa tctatatctg    2340
ggtagtatat gctatcctaa tctgtatccg ggtagcatat gctatcctca cgatgataag    2400
ctgtcaaaca tgagaattaa ttcttgaaga cgaaagggcc tcgtgatacg cctattttta    2460
taggttaatg tcatgataat aatggtttct tagacgtcag gtggcacttt tcggggaaat    2520
gtgcgcggaa cccctatttg tttattttc taaatacatt caaatatgta tccgctcatg    2580
agacaataac cctgataaat gcttcaataa tattgaaaaa ggaagagtat gagtattcaa    2640
catttccgtg tcgcccttat tcccttttt gcggcatttt gccttcctgt ttttgctcac    2700
ccagaaacgc tggtgaaagt aaaagatgct gaagatcagt tgggtgcacg agtgggttac    2760
atcgaactgg atctcaacag cggtaagatc cttgagagtt ttcgccccga gaacgttttt    2820
ccaatgatga gcacttttaa agttctgcta tgtggcgcgg tattatcccg tgttgacgcc    2880
gggcaagagc aactcggtcg ccgcatacac tattctcaga atgacttggt tgagtactca    2940
ccagtcacag aaaagcatct tacgatggc atgacagtaa agaattatg cagtgctgcc    3000 ataaccatga gtgataacac tgcggccaac ttacttctga caacgatcgg aggaccgaag    3060
gagctaaccg cttttttgca caacatgggg gatcatgtaa ctcgccttga tcgttgggaa    3120
ccggagctga atgaagccat accaaacgac gagcgtgaca ccacgatgcc tgcagcaatg    3180
gcaacaacgt tgcgcaaact attaactggc gaactactta ctctagcttc ccggcaacaa    3240
ttaatagact ggatggaggc ggataaagtt gcaggaccac ttctgcgctc ggcccttccg    3300
gctggctggt ttattgctga taaatctgga gccggtgagc gtgggtctcg cggtatcatt    3360
gcagcactgg ggccagatgg taagccctcc cgtatcgtag ttatctacac gacggggagt    3420
caggcaacta tggatgaacg aaatagacag atcgctgaga taggtgcctc actgattaag    3480
cattggtaac tgtcagacca gtttactca tatatacttt agattgattt aaaacttcat    3540
ttttaattta aaaggatcta ggtgaagatc ctttttgata atctcatgac caaaatccct    3600
taacgtgagt tttcgttcca ctgagcgtca gaccccgtag aaaagatcaa aggatcttct    3660
```

```
tgagatcctt tttttctgcg cgtaatctgc tgcttgcaaa caaaaaaacc accgctacca   3720
gcggtggttt gtttgccgga tcaagagcta ccaactcttt ttccgaaggt aactggcttc   3780
agcagagcgc agataccaaa tactgtcctt ctagtgtagc cgtagttagg ccaccacttc   3840
aagaactctg tagcaccgcc tacatacctc gctctgctaa tcctgttacc agtggctgct   3900
gccagtggcg ataagtcgtg tcttaccggg ttggactcaa gacgatagtt accggataag   3960
gcgcagcggt cgggctgaac gggggttcg tgcacacagc ccagcttgga gcgaacgacc     4020
tacaccgaac tgagatacct acagcgtgag cattgagaaa gcgccacgct tcccgaaggg   4080
agaaaggcgg acaggtatcc ggtaagcgg agggtcggaa caggagagcg cacgagggag    4140
cttccagggg gaaacgcctg gtatctttat agtcctgtcg ggtttcgcca cctctgactt   4200
gagcgtcgat ttttgtgatg ctcgtcaggg gggcggagcc tatggaaaaa cgccagcaac   4260
gcggcctttt tacggttcct ggccttttgc tggccttttg ctcacatgtt ctttcctgcg   4320
ttatcccctg attctgtgga taaccgtatt accgcctttg agtgagctga taccgctcgc   4380
cgcagccgaa cgaccgagcg cagcgagtca gtgagcgagg aagcgtacat ttatattggc   4440
tcatgtccaa tatgaccgcc atgttgacat tgattattga ctagttatta atagtaatca   4500 attacgggt cattagttca tagcccatat atggagttcc gcgttacata acttacggta     4560
aatggcccgc ctggctgacc gcccaacgac ccccgcccat tgacgtcaat aatgacgtat   4620
gttcccatag taacgccaat agggactttc cattgacgtc aatgggtgga gtatttacgg   4680
taaactgccc acttggcagt acatcaagtg tatcatatgc caagtccgcc cctattgac    4740 gtcaatgacg gtaaatggcc cgcctggcat tatgcccagt acatgacctt acgggacttt   4800
cctacttggc agtacatcta cgtattagtc atcgctatta ccatggtgat gcggttttgg   4860
cagtacacca atgggcgtgg atagcggttt gactcacggg gatttccaag tctccacccc   4920
attgacgtca atgggagttt gttttggcac caaaatcaac gggactttcc aaaatgtcgt   4980
aataaccccg ccccgttgac gcaaatgggc ggtaggcgtg tacggtggga ggtctatata   5040
agcagagctc gtttagtgaa ccgtcagatc ctcactctct tccgcatcgc tgtctgcgag   5100
ggccagctgt gggctcgcg gttgaggaca aactcttcgc ggtctttcca gtactcttgg    5160
atcggaaacc cgtcggcctc cgaacggtac tccgccaccg agggacctga gcgagtccgc   5220
atcgaccgga tcgaaaaacc tctcgagaaa ggcgtctaac cagtcacagt cgcaaggtag   5280
gctgagcacc gtggcgggcg gcagcgggtg gcggtcgggg ttgtttctgg cggaggtgct   5340
gctgatgatg taattaaagt aggcggt                                        5367
```

<210> SEQ ID NO 99
<211> LENGTH: 43
<212> TYPE: DNA
<213> ORGANISM: Artificial Sequence
<220> FEATURE:
<223> OTHER INFORMATION: primer to introduce IgGK signal peptide in the heavy chain variable region of 25A1

<400> SEQUENCE: 99

```
gggttccagg ttccactggc gaggtccagc tgcaacaatc tgg                           43
```

<210> SEQ ID NO 100
<211> LENGTH: 43
<212> TYPE: DNA
<213> ORGANISM: Artificial Sequence
<220> FEATURE:
<223> OTHER INFORMATION: primer to introduce IgGK signal peptide in the heavy chain variable regions of 24B4 and 25D8

```
<400> SEQUENCE: 100
gggttccagg ttccactggc caggtccaag tgcagcagcc tgg                    43

<210> SEQ ID NO 101
<211> LENGTH: 43
<212> TYPE: DNA
<213> ORGANISM: Artificial Sequence
<220> FEATURE:
<223> OTHER INFORMATION: primer to introduce IgGK signal peptide in the
      heavy chain variable regions of 25B8, 25C1 and 25E9

<400> SEQUENCE: 101
gggttccagg ttccactggc gagatccagc tgcagcagtc tgg                    43

<210> SEQ ID NO 102
<211> LENGTH: 43
<212> TYPE: DNA
<213> ORGANISM: Artificial Sequence
<220> FEATURE:
<223> OTHER INFORMATION: primer to introduce IgGK signal peptide in the
      heavy chain variable region of 25E5

<400> SEQUENCE: 102
gggttccagg ttccactggc gaagtgaagc ttgaggagtc tgg                    43

<210> SEQ ID NO 103
<211> LENGTH: 43
<212> TYPE: DNA
<213> ORGANISM: Artificial Sequence
<220> FEATURE:
<223> OTHER INFORMATION: primer to introduce IgGK signal peptide in the
      heavy chain variable region of 25E6

<400> SEQUENCE: 103
gggttccagg ttccactggc caggtccaac tgcagcagcc tgg                    43

<210> SEQ ID NO 104
<211> LENGTH: 38
<212> TYPE: DNA
<213> ORGANISM: Artificial Sequence
<220> FEATURE:
<223> OTHER INFORMATION: reverse primer to amplify heavy chain variable
      regions

<400> SEQUENCE: 104
ggggccaggg gaaagacaga tgggcccttc gttgaggc                          38

<210> SEQ ID NO 105
<211> LENGTH: 35
<212> TYPE: DNA
<213> ORGANISM: Artificial Sequence
<220> FEATURE:
<223> OTHER INFORMATION: primer to amplify a fragment of murine Siglec
      15 sequence

<400> SEQUENCE: 105
gtaagcgaat tcatggtgaa aactagaaga gacgc                             35

<210> SEQ ID NO 106
<211> LENGTH: 34
<212> TYPE: DNA
<213> ORGANISM: Artificial Sequence
<220> FEATURE:
<223> OTHER INFORMATION: primer to amplify a fragment of murine Siglec
      15 sequence

<400> SEQUENCE: 106
```

-continued

```
gtaagcaagc ttttagccgt ggaagcggaa cagg                                    34
```

<210> SEQ ID NO 107
<211> LENGTH: 981
<212> TYPE: DNA
<213> ORGANISM: Artificial Sequence
<220> FEATURE:
<223> OTHER INFORMATION: murine Siglec-15 (SEQ ID NO.:2 variant)

<400> SEQUENCE: 107

```
atggaggggt ccctccaact cctggcctgc ttggcctgtg tgctccagat gggatccctt       60
gtgaaaacta agagagacgc ttcgggggat ctgctcaaca cagaggcgca cagtgccccg      120
gcgcagcgct ggtccatgca ggtgcccgcg gaggtgaacg cggaggctgg cgacgcggcg      180
gtgctgccct gcaccttcac gcacccgcac cgccactacg acgggccgct gacggccatc      240
tggcgctcgg gcgagccgta cgcgggcccg caggtgttcc gctgcaccgc ggcgccgggc      300
agcgagctgt gccagacggc gctgagcctg cacggccgct ccgcctgct gggcaacccg       360
cgccgcaacg acctgtccct gcgcgtcgag cgcctcgccc tggcggacag cggccgctac      420
ttctgccgcg tggagttcac cggcgacgcc acgatcgct atgagagtcg ccatggggtc       480
cgtctgcgcg tgactgctgc gccgcggatc gtcaacatct cggtgctgcc gggccccgcg      540
cacgccttcc gcgcgctctg caccgccgag ggggagcccc cgcccgccct cgcctggtcg      600
ggtcccgccc aggcaacag ctccgctgcc ctgcagggcc agggtcacgg ctaccaggtg       660
accgccgagt gcccgcgct gaccgcgac ggccgctaca cgtgcacggc ggccaatagc        720
ctgggccgcg ccgaggccag cgtctacctg ttccgcttcc acggcgcccc cggaacctcg      780
accctagcgc tcctgctggg cgcgctgggc ctcaaggcct tgctgctgct tggcattctg      840
ggagcgcgtg ccacccgacg ccgactagat cacctggtcc cccaggacac ccctccacgt      900
gcggaccagg acacttcacc tatctggggc tcagctgaag aaatagaaga tctgaaagac      960
ctgcataaac tccaacgcta g                                               981
```

<210> SEQ ID NO 108
<211> LENGTH: 326
<212> TYPE: PRT
<213> ORGANISM: Artificial Sequence
<220> FEATURE:
<223> OTHER INFORMATION: murine Siglec-15 (SEQ ID NO.:2 variant)

<400> SEQUENCE: 108

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
            20                  25                  30

Asn Thr Glu Ala His Ser Ala Pro Ala Gln Arg Trp Ser Met Gln Val
        35                  40                  45

Pro Ala Glu Val Asn Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110

Arg Phe Arg Leu Leu Gly Asn Pro Arg Arg Asn Asp Leu Ser Leu Arg
        115                 120                 125
```

-continued

```
Val Glu Arg Leu Ala Leu Ala Asp Ser Gly Arg Tyr Phe Cys Arg Val
    130                 135                 140

Glu Phe Thr Gly Asp Ala His Asp Arg Tyr Glu Ser Arg His Gly Val
145                 150                 155                 160

Arg Leu Arg Val Thr Ala Ala Pro Arg Ile Val Asn Ile Ser Val Leu
                165                 170                 175

Pro Gly Pro Ala His Ala Phe Arg Ala Leu Cys Thr Ala Glu Gly Glu
            180                 185                 190

Pro Pro Pro Ala Leu Ala Trp Ser Gly Pro Ala Pro Gly Asn Ser Ser
        195                 200                 205

Ala Ala Leu Gln Gly Gln Gly His Gly Tyr Gln Val Thr Ala Glu Leu
    210                 215                 220

Pro Ala Leu Thr Arg Asp Gly Arg Tyr Thr Cys Thr Ala Ala Asn Ser
225                 230                 235                 240

Leu Gly Arg Ala Glu Ala Ser Val Tyr Leu Phe Arg Phe His Gly Ala
                245                 250                 255

Pro Gly Thr Ser Thr Leu Ala Leu Leu Leu Gly Ala Leu Gly Leu Lys
            260                 265                 270

Ala Leu Leu Leu Leu Gly Ile Leu Gly Ala Arg Ala Thr Arg Arg Arg
    275                 280                 285

Leu Asp His Leu Val Pro Gln Asp Thr Pro Pro Arg Ala Asp Gln Asp
    290                 295                 300

Thr Ser Pro Ile Trp Gly Ser Ala Glu Glu Ile Glu Asp Leu Lys Asp
305                 310                 315                 320

Leu His Lys Leu Gln Arg
                325
```